(12) United States Patent
DeLange et al.

(10) Patent No.: US 6,297,356 B1
(45) Date of Patent: Oct. 2, 2001

(54) TELOMERE REPEAT BINDING FACTORS AND DIAGNOSTIC AND THERAPEUTIC USE THEREOF

(75) Inventors: Titia DeLange; Dominique Broccoli; Agata Smogorzenska, all of New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/018,635

(22) Filed: Feb. 4, 1998

Related U.S. Application Data

(63) Continuation-in-part of application No. 08/938,052, filed on Sep. 26, 1997, now abandoned, which is a continuation-in-part of application No. 08/519,103, filed on Aug. 25, 1995, now Pat. No. 5,733,730.

(51) Int. Cl.[7] .......................... C07K 13/00; C07K 15/28; C12Q 1/68
(52) U.S. Cl. ................................ 530/350; 435/6; 530/386
(58) Field of Search ................................ 435/6; 530/350, 530/386

(56) References Cited

U.S. PATENT DOCUMENTS 5,733,730 * 3/1998 De Lange .................................. 435/6

OTHER PUBLICATIONS

Bilaud et al, Nicleic Acid Res 24;1294–1303, 1996.*
Brigati et al, Mol. Cell. Biol. 13:1306–1314, 1993.*
Allshire et al (1998) Nature 332:656–659.
Blackburn et al. (1984) Cell 36: 447–458.
Broccoli et al. (1995) Proc. Natl. Acad. Sci. USA 92:9082–6.
Brown (1986) Nature 338:774–776; Cross et al (1989) Nature 338: 771–774.
Cardenas et al in 1993 (Genes and Devel. 7:883–894).
Chong et al. (1995) Science 270, 1663–1667.
Cross et al (1989) Nature 338:771–774.
DePalma, A. (1995) Genet. Engin. News 15(16): 1,13.
Hanish et al (1994) Proc. Natl. Acad. Sci. USA 91:8861–8865.
Ishikawa et al (1993) Mol. Cell Biol. 13:4301–4310.
de Lange, T. (1995) In Telomeres, Cold Spring Harbor Monograph, E. H. Blackburn and C. W. Greider, Eds.
de Lange Proc. Natl. Acad. Sci. USA 91:2882–2885, 1994.
de Lange (1992) EMBO J. 11:717–724.
de Lange et al (Mol. Cell. Biol. 10:518–527, 1990.
Lundblad et al (1989) Cell 83:633–643.
McKay et al (1992) Nucl. Acids Res. 20:6461–6464.
McKay et al. (1992) Nucl. Acids. Res. 20:1387–1391.
Moyzis et al (1988) Proc. Natl. Acad. Sci. USA 85:6622–6626.
Van der Ploeg et al (1984) Cell 36:459–468.
Saltman et al (1993) Chromosoma 102:121–128.
Szostak et al (1982) Cell 36:459–568.
Tommerup et al (1994) Mol. Cell. Biol. 14:5777–5785.
Zakian, V.A. (1995) Science 270:1601–7.
Zhong et al (1992) Mol. Cell. Biol. 13:4834–4943.
Bilaud et al. (1996) Nuc. Acids Res. 24:1294–303.
Brigati et al. (1993) Mol. Cell. Biol. 13:1306–14.
Chong et al. (1995) Science 270:1663–7.
De Lange, T. (1996) Seminar Cell Dev. Biol. 7:23–9.
Sheng et al. (1995) Mol. Cell. Biol. 15:1144–53.
Uhlen et al. (1989) Nature 340:733–4.

* cited by examiner

Primary Examiner—Eggerton A. Campbell
(74) Attorney, Agent, or Firm—Klauber & Jackson

(57) ABSTRACT

The present invention relates to a novel nucleotide sequence encoding a telomeric protein which binds a repeat region of telomeric sequences, and to the protein encoded thereby. Also included within the invention are expression vectors for the production of the telomeric protein and host cells transformed with the nucleotide sequence. In addition, antibodies, probes and antagonists specific for the telomeric protein are contemplated. Methods of identifying antagonists of the telomeric protein, diagnostic methods of identifying the telomeric protein in a sample, and therapeutic uses of the telomeric protein, particularly in the treatment of aging and cancer, are also contemplated.

38 Claims, 27 Drawing Sheets

FIG. 1A

T7:      E A E E V F E . . .                                      (SEQ ID NO:1)
                t $m/z=1009.2$
               assuming Glu @ 4 and Arg @ C-t: [MH$^+$]=1009.06
               $\Delta=0.14$ dalton T8:      T L D A (Q) F E N (d) E . . .                         (SEQ ID NO:2)

$m/z=1337.9$
               assuming sequence as written and Arg @ C-t: [MH$^+$]=1338.38
               $\Delta=0.48$ dalton T10:     T I T (S) Q D K P x x N x V x M . . .    ($m/z=2676$)     (SEQ ID NO:3)

T11:     I L L x Y K ‖           (no-mass)                 (SEW(SEQ ID NO:4)

T12:     N (q) A I A V . . .      ($m/z=1659$)             (SEQ ID NO:5)

T13:     I F (G) D P N . . .       ($m/z=1409$)             (SEQ ID NO:6)

T14:     N L F L . . .            (no mass)              (SEQ ID NO:7)

T20:     x Y V N Y V L x E K ‖                             (SEQ ID NO:8)

FIG. 1B

*m/z*=1156.6, 1172.9, 1201.4 (three signals)
Assuming (x, x) = (Gly, Ala) : [MH$^+$]=1156.33
Assuming (x, x) = (Gly, Ser) : [MH$^+$]=1172.33
Assuming (x, x) = (Ser, Ser) : [MH$^+$]=1202.35

The "Ala" scenario is somewhat unlikely as this residue is easily detectable whereas Gly and Ser are not (at the femtomole level).

T26:         Q A x L x E E D K ‖                                  (SEQ ID NO:9)

no conclusive mass result was obtained
        the peptide contains Trp ($A_{297/277}$ = 25%)

T29:         T I Y I C Q F L T . . .                              (SEQ ID NO:10)

*m/z*=1363.0
        assuming Arg @ C-t: [MH$^+$]=1363.53
        Δ=0.53 dalton

Symbols:   1) x : no residue could be identified at this position
           (AMINO ACID) : identification with lower degree of confidence
           (amino acid) : residue present but at very low levels 2) ‖ indicates C-terminus of peptide
           . . . : no more interpretable signals, but unlikely to be C-terminus 3) [M+H$^+$] : sum of the average isotopic masses of all identified (positively
             and tentatively) residues plus one proton [H$^+$]
           *m/z* : experimental mass (by laser-desorption mass spectrometry)

FIG. 2A

```
ATGGAGCCAT TTAACATGGC GGAGGATGTT TCCTCAGGGC CCCCGAGCCC GCGGCGGTGT GCGGATGGTA GGGATGCCGA CCCTACTGAG GACCAGATGG
 I  E  P  F  N  M  A  E  D  V  S  S  G  P  P  S  P  R  R  C  A  D  G  R  D  A  D  P  T  E  E  Q  M
                  50                                                                  100

CAGAAACAGA GAGAAACGAC GAGGAGACAGT TCGAATGCCA GGAACTGCTC GAGTGCCAGG TGCAGGTGGG GGCCCCCGAG GAGGAGGAGG AGGAGGAGGA
 A  E  T  E  R  N  D  E  E  Q  F  E  C  Q  E  L  L  E  C  Q  V  Q  V  G  A  P  E  E  E  E  E  E  E
            150                                                               200

GGACGCGGGC CTGGTGGCCG AGGCCGAGGC CGTGGCTGCC GGCTGGATGC TGATTCCT CTGCCCTCT CTTTGCCGAG CGGCCGCTCC
 D  A  G  L  V  A  E  A  E  A  V  A  A  G  W  M  L  D  P  L  C  L  S  L  C  R  A  F  R  D  G  R  S
                  250                                                                 300

GAGGACTTCC GCGAGGACCCG CAACAGAGCGCA GAGGCTATTA CATGATGACT ATCCAGTCTA ACAGCTTGCC AGTTGAGAAC GATATACATA TGTCAGTTTT
 E  D  F  R  R  T  R  N  S  A  E  A  I  H  G  L  S  S  L  T  A  C  Q  L  R  T  I  Y  I  C  Q  F
            350                                                               400

TGACAGAGAA TGCAGCAGAA AAAACCCTTG ATGAAGAAAT TGAAAATGAT GAAGAATTA CACCCTTGA ATCAGCCCTG ATGATTTGG GTTCAATTGA
 L  T  R  I  A  A  G  K  T  L  D  A  Q  F  E  N  D  E  R  I  T  P  L  E  S  A  L  M  I  W  G  S  I  E
                  450                                                                 500

AAAGGAACAT GACAAACTTC ATGAAGAAAT ACAGAATTTA ATTAAATC AGCTATAGC CAAATTGCTT ATGATAAATC CTCAGAAAGA AGCAGAAGAA
 K  E  H  D  K  L  H  E  E  I  Q  N  L  I  K  I  Q  A  I  A  V  C  M  E  N  G  N  P  K  E  A  E  E
            550                                                               600

GTCTTTGAAA GAATATTGGG TGATCCAAAT TCTCATATGC CTTTCAAAAG CAAATTGCTT ATGATAAATC CTCAGAAAGA AGCAGAAGAA
 V  F  E  R  I  F  G  D  P  N  S  H  M  P  F  K  S  K  L  L  M  I  I  S  Q  K  D  T  F  H  S  P  F
                  650                                                                 700

AACACTTCAG GAATATTGAA AAATTAAGAG TTATGTGTAA TATGTGCTAA GTGAAAAATC ATCAACTTT CTAATGAAGG CACGGGCAAA
 Q  H  F  S  Y  N  H  M  M  E  K  I  K  S  Y  V  N  Y  V  L  S  E  K  S  S  T  P  L  M  K  A  A  A  K
            750                                                               800
```

FIG. 2B

```
                    850                               900
AGTAGTAGAA AGCAAAAGGA CAAGAACAAT AACTTCTCAA GATAAACCTA GTGGTAATGA TGTTGAAATG GAAACTGAAG CTAATTTGGA TACAAGAAAA
  V V E    S K R R    T R T I    T S Q D K P    S G N D V E M    E T E A N L D    T R K>
                    950                               1000
AGTGTTAGTG ACAAACAGTC TGCGGTAACT GAATCCTCAG AGGGTACAGT ATCCTTATTG AGTCTCCACA AGAATCTTTT CTTATCTAAG TTGCAACATG
  S V S    D K Q S    A V T    E S S    E G T V    S L L    R S H    K N L F    L S K    L Q H>
                    1050                              1100
GAACCCAGCA ACAAGACCTT AATAAGAAAG AAAGAACAGT AGGAACTCCT CAAAGTACAA AAAAGAAAA AGAAAGCAGA AGAGCCACTG AAAGCAGAAT
  G T Q Q    D L N K K    E R R V    G T P    Q S T    K K K K    E S R R    A T E S R L>
                    1150                              1200
ACCTGTTTCA AAGAGTCAGC CGGTAACTCC TGAAAAACAT CGAGCTAGAA AAGACAGGA ATGGCTTTGG GAAGAAGACA AGAATTTGAG ATCTGGCGTG
  P V S    K S Q    P V T P    E K H    R A R    K R Q A    W L W    E E D    K N L R    S G V>
                    1250                              1300
AGGAAATATG GAGAGGGAAA CTGGTCTAAA ATTATAAATT CAACAACCGG ACAAGTGTCA TGTTAAAAGA CAGATGGAGG ACCATGAAGA
  R K Y    G E G N    W S K    I L L    H Y K P    N N R    T S V    M L K D    R W R    T M K>
                    1350                              1400
AACTAAAAACT GATTCCTCA GACACGGAAG ACTGATTGTG TTTAAAGCAT GTATTTGAT CTTGATGAAA GGACAGTTAA GTATTTTGAT CACTGCATTT TGTTTGAAAC
  K L K L    I S S    D S E D    * L C    L * K    H Y S I    F L *    P S I N    E G L    C Y Q S    * I>
                    1450                              1500
CTTGATGATT GATTAATTAT CCCAAATCCT GTTCCAATGA
  L D E    R T V K    Y F P D    H C I    L F E T>
                    1550                              1600
TTGTGTCATT GATGAATTTA AAAACTTTTG TTTAAAGCAT TACAGTATTT TTTCTGTGACC ATCAATTAT GAGGGTTTGT GCTACCAGAG TTAAAGCATA
  C V I    D V I *    N F C    L K H    Y S I    F L *    P S I N    E G L    C Y Q S    * I>
TGCTAATCAT GTATTCTTA AGAACCTTAT TTTGATAAAA TGTAAATTTG CCACATTTAG TATCCCACC CCCAAATCCT GTCCAATGA
  C Y H    C I L *    E P Y    F D K M    * I C    * T L    P H L    V S P P    P N P    V P M>

AAAAATTAAA ACCTGATACG AAAAAAAA
  K K L K    P D T    K K K>
```

FIG. 3

MAEDVSSAAPSPRRCADGRDADPTEEQMAETERN*DEEQFECQELLECQVQVG*

*APEEEEEEEED*AGLVAEAEAVAAGWMLDFLCLSLCRAFRDGRSEDFRRTRNS

AEAIIHGLSSLTACQL<u>RTIYICQFLTR</u>IAAGK<u>TLDAQFENDER</u>ITPLESALM

IWGSIEKEHDKLHEEIQNLIK<u>IQAIAV</u>CMENGNFK<u>EAEEVFERIFGDPN</u>SHM

PFKSKLLMIISQKDTFHSFFQHFSYNHMMEKIKS<u>YVNYVLSEK</u>SSTFLMKAA

AKVVESKRT<u>RTITSQDKPSGNDVEM</u>ETEANLDTRKSVSDKQSAVTESSEGTV

SLLRSHK<u>NLFL</u>SKLQHGTQQQDLNKKERRVGTPQSTKKKKESRRATESRIPV

SKSQPVTPEKHRARKRQAWLWEEDKNLRSGVRKYGEGNWSK<u>ILLHYK</u>F

NNRTSVMLKDRWRTMKKLKLISSDSED

FIG. 4

```
Hu amyb   R2   LIKGPWTKEEDQRVIELVQKYGPKRWSLIAKHLKG..RIGKQCRERWHNHLNPE
Mu cmyb   R2   LIKGPWTKEEDQRVIKLVQKYGPKRWSVIAKHLKG..RIGKQCRERWHNHLNPE
Hu TRF         RKRQAWLWEEDKNLRSGVRKYGEGNWSKILLHYKFNNRTSVMLKDRWR.TMKKL
Hu amyb   R3   VKKSSWTEEEDRIIYEAHKRLG..NRWAEIAKLLPG..RTDNSIKNHWNSTMRRK
Hu bmyb   R3   VKKSCWTEEEDRIICEAHKVLG..NRWAEIAKMLPG..RTDNAVKNHWNSTIKRK
Mu cmyb   R3   VKKTSWTEEEDRIIYQAHKRLG..NRWAEIAKLLPG..RTDNAIKNHWNSTMRRK
Dro myb   R3   IKKTAWTEKEDEIIYQAHLELG..NQWAKIAKRLPG..RTDNAIKNHWNSTMRRK
```

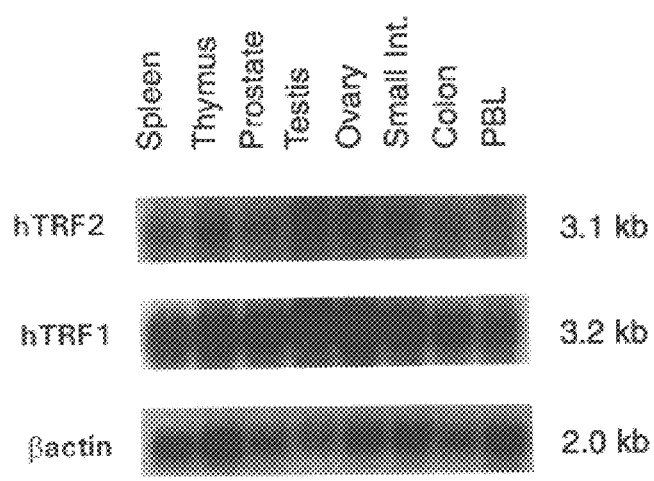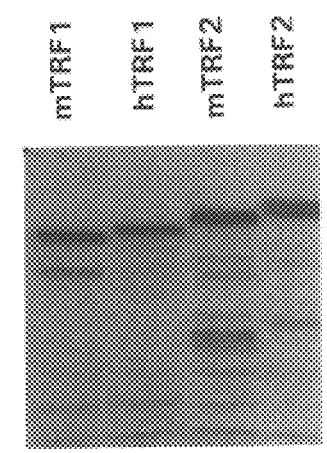

FIG. 9A

| | | | |
|---|---|---|---|
| mTRF2 | 1 | MAGGGGSSDSS------GRAAASRRASRSGGRAR----------RGRHEPGLGGAAERGAGE----- | 45 |
| hTRF2 | 1 | MAGGGGSSDGS------GRAAAGRRASRSSGGRAR----------RGRHEPGLGGPAERGAGE----- | 45 |
| mTRF1 | 1 | MAETVSSAA-------RDAPSREGWTDSDSPEQEEVGDDAELLQCLQLGTPREMENAE----LV | 54 |
| hTRF1 | 1 | MAEDVSSAAPSPRRCADGRDADPTEEQMAETERNDEEQFECQELLECQVQVGAPEEEEEEEDAGLV | 67 |

| | | | |
|---|---|---|---|
| mTRF2 | 46 | ARLEEAVNRWVLKFYFHEALRAFSSRYRDFRQIRDIMQALLVRPLGKEHTVSRLLRVMQCLSRIEE | 112 |
| hTRF2 | 46 | ARLEEAVNRWVLKFYFHEALRAFRGSRYGDFRQIRDIMQALLVRPLGKEHTVSRLLRVMQCLSRIEE | 112 |
| mTRF1 | 55 | AEVEAVAAGWMLDFLCLSLCRAFRDGRSEDFRRTRDSAEAIIHGLHRLTAYQLKTVYICQFLTRVAS | 121 |
| hTRF1 | 68 | AEAEAVWPGWMLDFLCLSLCRAFRDGRSEDFRRTRNSAEAIIHGLSSLTACQLRTIYICQFLTRIAA | 134 |

| | | | |
|---|---|---|---|
| mTRF2 | 113 | GENLDCSFDMEAELTPLESAINVLEMIKTEFTLTDSMVESSRKLVKEAAVIICIKNKEFEKASKILK | 179 |
| hTRF2 | 113 | GENLDCSFDMEAELTPLESAINVLEMIKTEFTLTEAVVESSRKLVKEAAVIICIKNKEFEKASKILK | 179 |
| mTRF1 | 122 | GKALDAQFEVDERITPLESALMIWNSIEKEHDKLHDEIKN---LIKIQAVAVCMEIGSFKEAEEVFE | 185 |
| hTRF1 | 135 | GKTLDAQFENDERITPLESALMIWGSIEKEHDKLHEEIQN---LIKIQAIAVCMENGNFKEAEEVFE | 198 |

| | | | |
|---|---|---|---|
| mTRF2 | 180 | KYMSKDP-TTQKLRTDLLNIIREKNLAHPVIQNFSYEVFQQKMLRFLESHLDDTEPYLLTMAKKALK | 245 |
| hTRF2 | 180 | KHMSKDP-TTQKLRNDLLNIIREKNLAHPVIQNFSYETFQQKMLRFLESHLDDAEPYLLTMAKKALK | 245 |
| mTRF1 | 186 | RIFG-DPEFYTPLERKLLKIISQKDVFHSLFQHFSYSCMMEKIQSYVGDVLSEKSSTFLMKAATKVV | 251 |
| hTRF1 | 199 | RIFG-DPNSHMPFKSKLLMIISQKDTFHSFFQHFSYNHMMEKIKSYVNYVLSEKSSTFLMKAAAKVV | 264 |

FIG. 9A-1

```
246 SESAASSTMREEK--HPEPVEKPLREPPRPQNPPATIGIRTLKAAFKALSTAQDSEAAFAKLDQKD 310
246 SESAASSTGKEDKQPAPGPVEKPPREPARQLRNPPTTIGMTLKAAFKTLSGAQDSEAAFAKLDQKD 312
252 ENEKARTQASKDR----------------------PDATNTGMDTEVGLNKEKSVNGQQSTETEPLVD- 297
265 ESKRTRTITSQDK-----------------------PSGNDVEMETEANLDTRKSVSDKQSAVTESSEG- 310

311 LVLANLASPSSPAHKHKRPRKDEHESAAPAEGEGGSSRQPRNSPMTISRLLEEDSQSTEPSPGLNS 377
313 LVLPTQALPASPALNKRPRKDENESSAPADGEGGSELQPKNKRMTISRLVLEEDSQSTEPSAGLNS 379
298 -TVSSIRSHKN-ALSQLKHRRA-------------------PSDFSRNEARTGTLQCETTMERNRRTSG 345
311 -TVSLLRSHKNLFLSKLQHGTQ---------------------QQDLNKKERRVGTPQSTKKKKESR-RAT 358

378 SHEAMSAS--KPRALNQPHPGEKKPKASKDKWNSPNGLEEKEVWLEEDQLFEVQAP-GEDRSSSLTR 441
380 SQEAASAPPSKPTVLNQPLPGEKNPKVPKGKWNSSNGVEEKETWVEEDELFQVQAAPDEDSTTNITK 446
346 RNRLCVSE------NQPDTDDKSGRR-------------------------------K 366
359 ESRIPVSK------SQPVTPEKHRAR-------------------------------K 379

442 KQKWTIEESEWVKDGVRKYGEGNWAAISKSYPFVNRTAVMIKDRWRTMKKLGMN----- 495
447 KQKWTVEESEWVKAGVQKYGEGNWAAISKNYPFVNRTAVMIKDRWRTMKRLGMN----- 500
367 RQTWLWEEDRILKCGVKKYGEGNWAKILSHYKFNNRTSVMLKDRWRTMKRLKLIS---- 421
380 RQAWLWEEDKNLRSGVRKYGEGNWSKILLHYKFNNRTSVMLKFNNRTSVMLKKLISSDSED 439
```

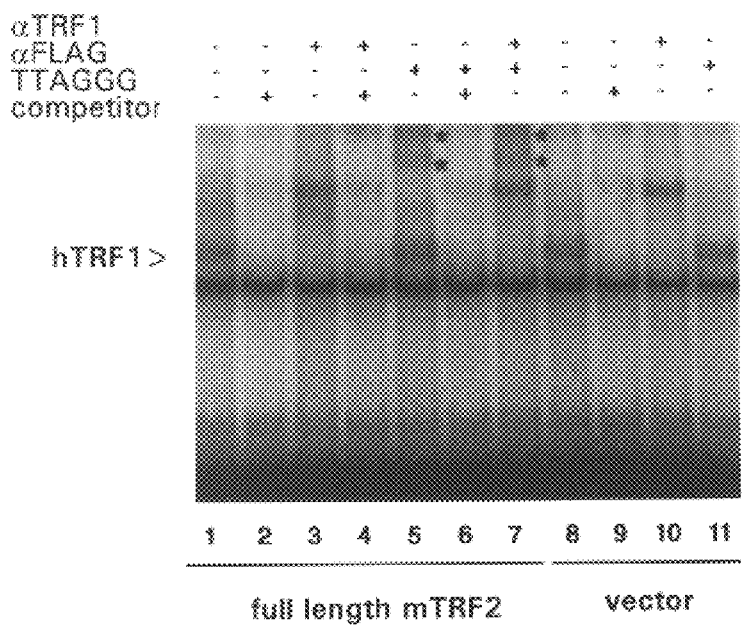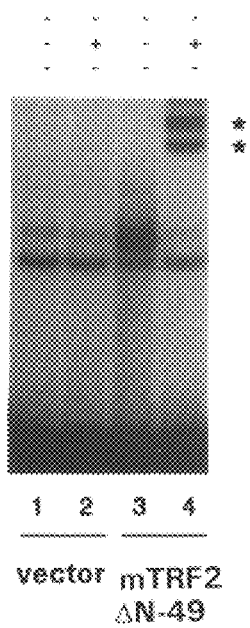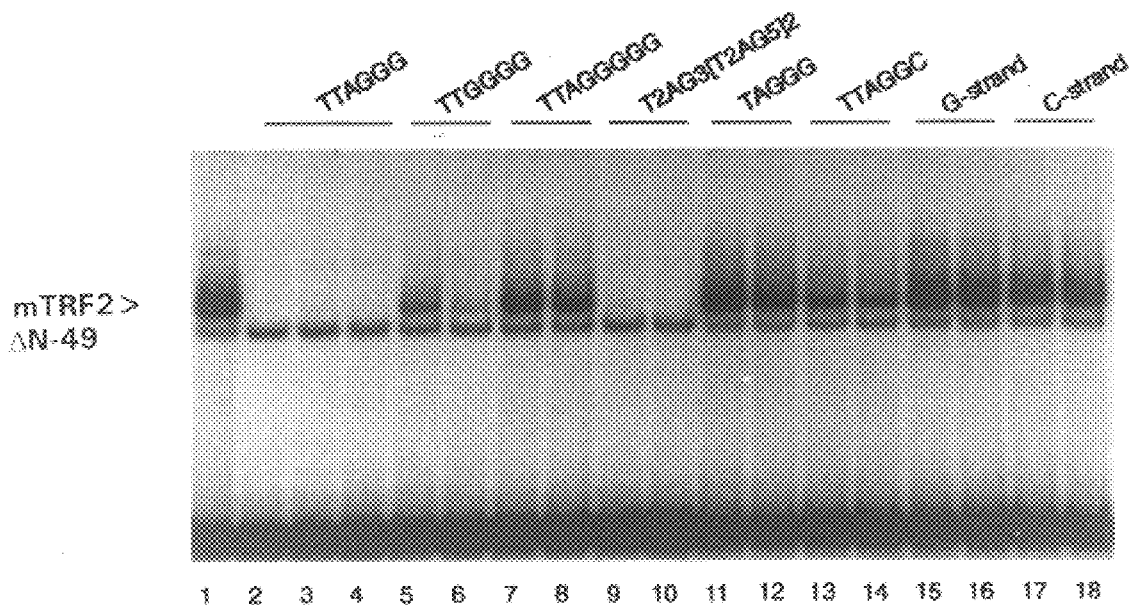

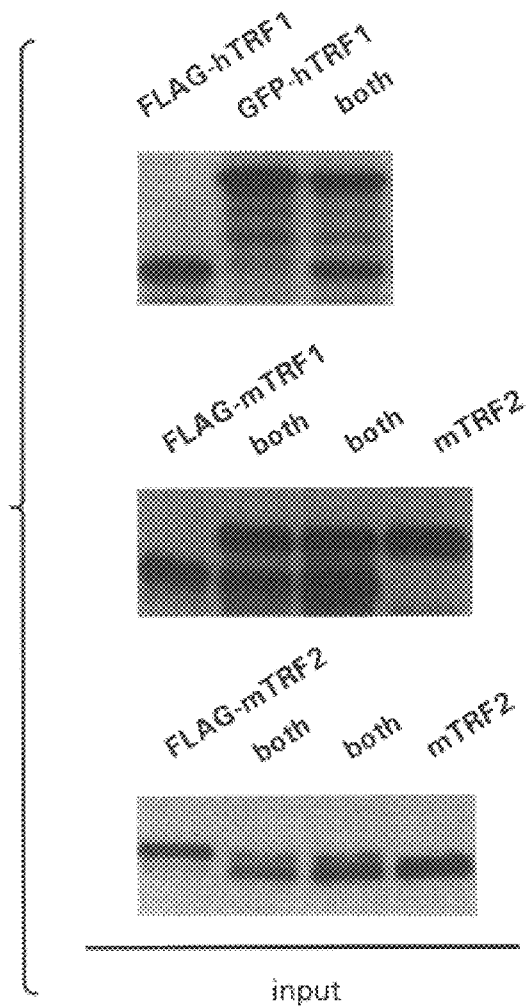
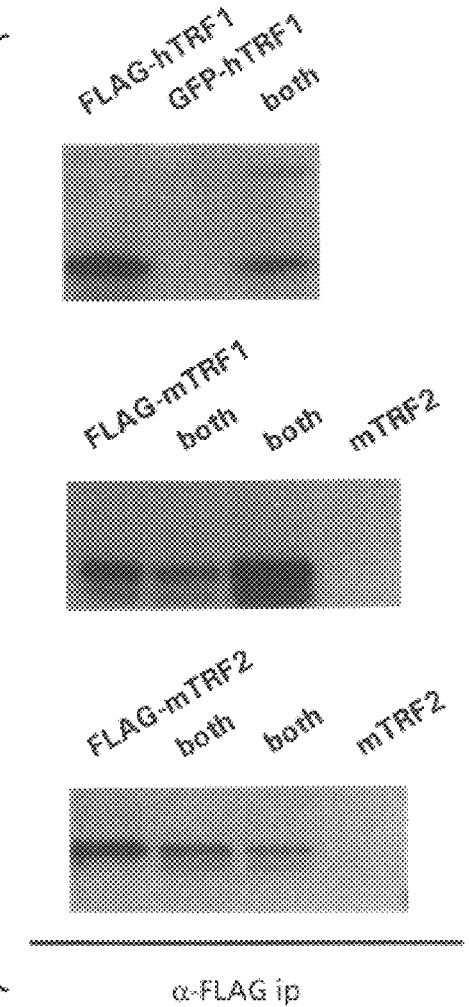
FIG.12B
FIG.12C

FIG.14A FIG.14B FIG.14C FIG.14D
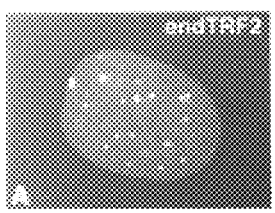 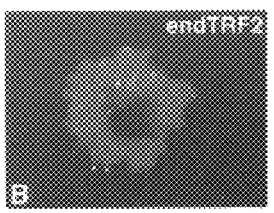 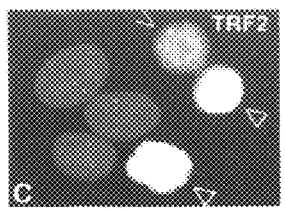 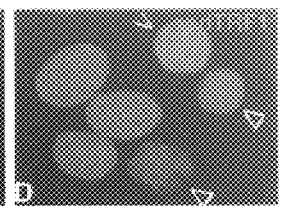
FIG.14E FIG.14F FIG.14G FIG.14H
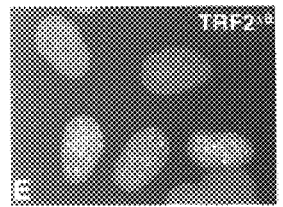 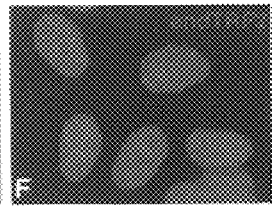 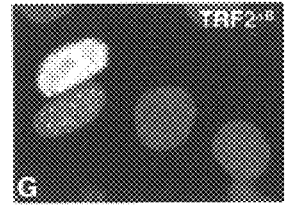 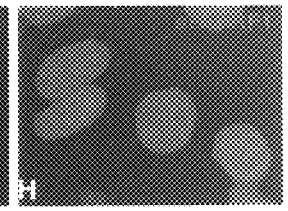
FIG.14I FIG.14J FIG.14K FIG.14L
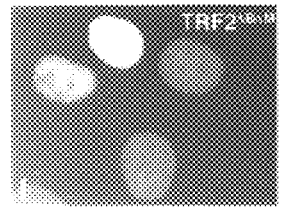 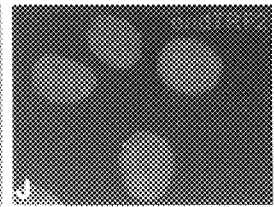 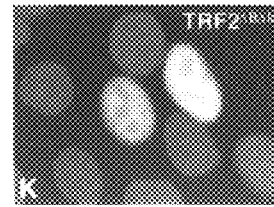 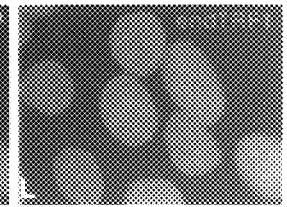

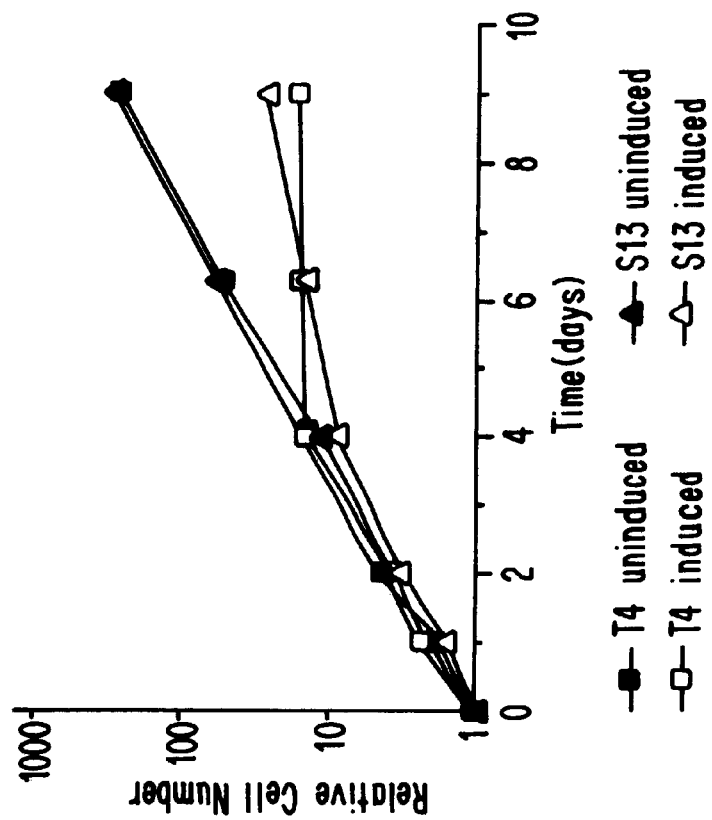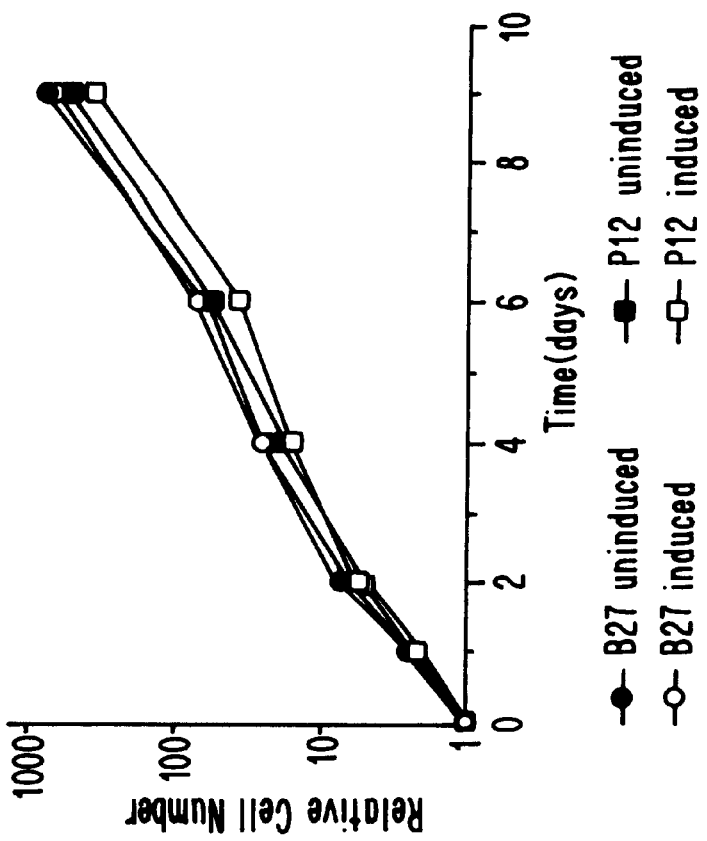

T4 ind. day 9 DNA
digested with Bal31
0 10 20 30 40 60 80 min

T19 ind. day 9 DNA
digested with Bal31

T4 ind. day 9 DNA
37 60 70 80 85 90 100 °C

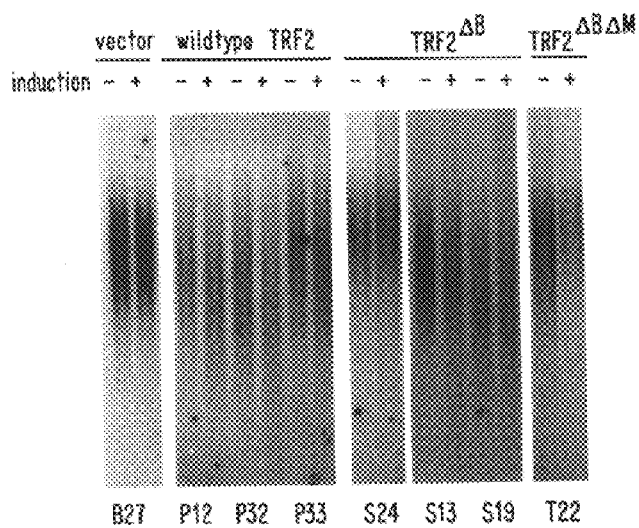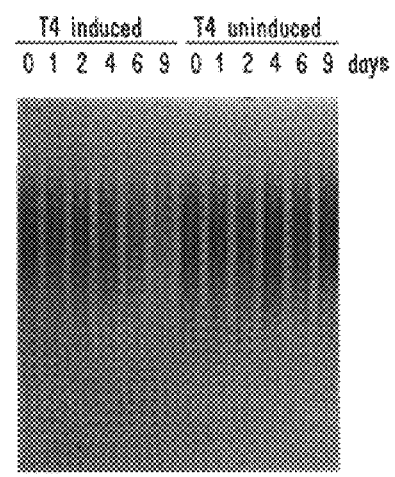

SEQUENCE LISTING (1) GENERAL INFORMATION:

(iii) NUMBER OF SEQUENCES: 52

(2) INFORMATION FOR SEQ ID NO:1:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

Glu Ala Glu Glu Val Phe Glu
1             5

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

Thr Leu Asp Ala Gln Phe Glu Asn Asp Glu
1             5                  10

(2) INFORMATION FOR SEQ ID NO:3:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:3:

Thr Ile Thr Ser Gln Asp Lys Pro Xaa Xaa Asn Xaa Val Xaa Met
1               5                  10                  15

(2) INFORMATION FOR SEQ ID NO:4:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:4:

Ile Leu Leu Xaa Tyr Lys
1               5

(2) INFORMATION FOR SEQ ID NO:5:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:5:

Asn Gln Ala Ile Ala Val
1               5

(2) INFORMATION FOR SEQ ID NO:6:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:6:

Ile Phe Gly Asp Pro Asn
1               5

(2) INFORMATION FOR SEQ ID NO:7:

(i) SEQUENCE CHARACTERISTICS:
         (A) LENGTH: 4 amino acids
         (B) TYPE: amino acid
         (C) STRANDEDNESS: single
         (D) TOPOLOGY: linear (ii) MOLECULE TYPE: peptide (xi) SEQUENCE DESCRIPTION: SEQ ID NO:7:

Asn Leu Phe Leu
1

(2) INFORMATION FOR SEQ ID NO:8:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: DNA (genomic)

(xi) SEQUENCE DESCRIPTION: SEQ ID NO:8:

Xaa Tyr Val Asn Tyr Val Leu Xaa Glu Lys
1               5                   10

(2) INFORMATION FOR SEQ ID NO:9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

Gln Ala Xaa Leu Xaa Glu Glu Asp Lys
1               5

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

Thr Ile Tyr Ile Cys Gln Phe Leu Thr
1               5

(2) INFORMATION FOR SEQ ID NO:11:

(i) SEQUENCE CHARACTERISTICS:
        (A) LENGTH: 1629 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

| | | | | |
|---|---|---|---|---|
| ATCGAGCCAT | TTAACATGGC | GGAGGATGTT | TCCTCAGCGG | CCCCGAGCCC | GCGGCGGTGT | 60 |
| GCGGATGGTA | GGGATGCCGA | CCCTACTGAG | GAGCAGATGG | CAGAAACAGA | GAGAAACGAC | 120 |
| GAGGAGCAGT | TCGAATGCCA | GGAACTGCTC | GAGTGCCAGG | TGCAGGTGGG | GGCCCCCGAG | 180 |
| GAGGAGGAGG | AGGAGGAGGA | GGACGCGGGC | CTGGTGGCCG | AGGCCGAGGC | CGTGTGGCCG | 240 |
| GGCTGGATGC | TCGATTTCCT | CTGCCTCTCT | CTTTGCCGAG | CTTTCCGCGA | CGGCCGCTCC | 300 |
| GAGGACTTCC | GCAGGACCCG | CAACAGCGCA | GAGGCTATTA | TTCATGGACT | ATCCAGTCTA | 360 |
| ACAGCTTGCC | AGTTGAGAAC | GATATACATA | TGTCAGTTTT | TGACAAGAAT | TGCAGCAGGA | 420 |
| AAAACCCTTG | ATGCACAGTT | TGAAAATGAT | GAACGAATTA | CACCCTTGGA | ATCAGCCCTG | 480 |
| ATGATTTGGG | GTTCAATTGA | AAAGGAACAT | GACAAACTTC | ATGAAGAAAT | ACAGAATTTA | 540 |
| ATTAAAATTC | AGGCTATAGC | TGTTTGTATG | GAAAATGGCA | ACTTTAAAGA | AGCAGAAGAA | 600 |
| GTCTTTGAAA | GAATATTTGG | TGATCCAAAT | TCTCATATGC | CTTTCAAAAG | CAAATTGCTT | 660 |
| ATGATAATCT | CTCAGAAAGA | TACATTTCAT | TCCTTTTTTC | AACACTTCAG | CTACAACCAC | 720 |
| ATGATGGAGA | AAATTAAGAG | TTATGTGAAT | TATGTGCTAA | GTGAAAAATC | ATCAACCTTT | 780 |
| CTAATGAAGG | CAGCGGCAAA | AGTAGTAGAA | AGCAAAAGGA | CAAGAACAAT | AACTTCTCAA | 840 |
| GATAAACCTA | GTGGTAATGA | TGTTGAAATG | GAAACTGAAG | CTAATTTGGA | TACAAGAAAA | 900 |

```
AGTGTTAGTG ACAAACAGTC TGCGGTAACT GAATCCTCAG AGGGTACAGT ATCCTTATTG     960

AGGTCTCACA AGAATCTTTT CTTATCTAAG TTGCAACATG GAACCCAGCA ACAAGACCTT    1020

AATAAGAAAG AAAGAAGAGT AGGAACTCCT CAAAGTACAA AAAAGAAAAA AGAAAGCAGA    1080

AGAGCCACTG AAAGCAGAAT ACCTGTTTCA AGAGTCAGC CGGTAACTCC TGAAAAACAT    1140

CGAGCTAGAA AAAGACAGGC ATGGCTTTGG GAAGAAGACA AGAATTTGAG ATCTGGCGTG    1200

AGGAAATATG GAGAGGGAAA CTGGTCTAAA ATACTGTTGC ATTATAAATT CAACAACCGG    1260

ACAAGTGTCA TGTTAAAAGA CAGATGGAGG ACCATGAAGA AACTAAAACT GATTTCCTCA    1320

GACAGCGAAG ACTGATTGTG TTTGTAAAAG CTTGATGAAA GGACAGTTAA GTATTTGAT    1380

CACTGCATTT TGTTTGAAAC TTGTGTCATT GATGTAATTT AAAACTTTTG TTTAAAGCAT    1440

TACAGTATTT TTCTGTGACC ATCAATTAAT GAGGGTTTGT GCTACCAGAG TTAAAGCATA    1500

TGCTATCATT GTATTCTTTA AGAACCTTAT TTTGATAAAA TGTAAATTTG TTGAACCCTC    1560

CACATTTAGT ATCCCCACCC CCAAATCCTG TTCCAATGAA AAAATTAAAA CCTGATACGA    1620

AAAAAAAG                                                            1629
```

(2) INFORMATION FOR SEQ ID NO:12:

(i) SEQUENCE CHARACTERISTICS:
        (A) LENGTH: 439 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:12:

```
Met Ala Glu Asp Val Ser Ser Ala Pro Ser Pro Arg Arg Cys Ala
1               5                   10                  15

Asp Gly Arg Asp Ala Asp Pro Thr Glu Glu Gln Met Ala Glu Thr Glu
                20                  25                  30

Arg Asn Asp Glu Glu Gln Phe Glu Cys Gln Glu Leu Leu Glu Cys Gln
            35                  40                  45

Val Gln Val Gly Ala Pro Glu Glu Glu Glu Glu Glu Glu Asp Ala
    50                  55                  60

Gly Leu Val Ala Glu Ala Glu Ala Val Ala Ala Gly Trp Met Leu Asp
65                  70                  75                  80

Phe Leu Cys Leu Ser Leu Cys Arg Ala Phe Arg Asp Gly Arg Ser Glu
                85                  90                  95

Asp Phe Arg Arg Thr Arg Asn Ser Ala Glu Ala Ile Ile His Gly Leu
            100                 105                 110

Ser Ser Leu Thr Ala Cys Gln Leu Arg Thr Ile Tyr Ile Cys Gln Phe
        115                 120                 125

Leu Thr Arg Ile Ala Ala Gly Lys Thr Leu Asp Ala Gln Phe Glu Asn
    130                 135                 140

Asp Glu Arg Ile Thr Pro Leu Glu Ser Ala Leu Met Ile Trp Gly Ser
145                 150                 155                 160

Ile Glu Lys Glu His Asp Lys Leu His Glu Glu Ile Gln Asn Leu Ile
                165                 170                 175

Lys Ile Gln Ala Ile Ala Val Cys Met Glu Asn Gly Asn Phe Lys Glu
            180                 185                 190

Ala Glu Glu Val Phe Glu Arg Ile Phe Gly Asp Pro Asn Ser His Met
        195                 200                 205
```

```
Pro Phe Lys Ser Lys Leu Leu Met Ile Ile Ser Gln Lys Asp Thr Phe
    210                 215                 220
His Ser Phe Phe Gln His Phe Ser Tyr Asn His Met Glu Lys Ile
225                 230                 235                 240
Lys Ser Tyr Val Asn Tyr Val Leu Ser Glu Lys Ser Ser Thr Phe Leu
                245                 250                 255
Met Lys Ala Ala Ala Lys Val Val Glu Ser Lys Arg Thr Arg Thr Ile
            260                 265                 270
Thr Ser Gln Asp Lys Pro Ser Gly Asn Asp Val Glu Met Glu Thr Glu
        275                 280                 285
Ala Asn Leu Asp Thr Arg Lys Ser Val Ser Asp Lys Gln Ser Ala Val
    290                 295                 300
Thr Glu Ser Ser Glu Gly Thr Val Ser Leu Leu Arg Ser His Lys Asn
305                 310                 315                 320
Leu Phe Leu Ser Lys Leu Gln His Gly Thr Gln Gln Gln Asp Leu Asn
                325                 330                 335
Lys Lys Glu Arg Arg Val Gly Thr Pro Gln Ser Thr Lys Lys Lys Lys
            340                 345                 350
Glu Ser Arg Arg Ala Thr Glu Ser Arg Ile Pro Val Ser Lys Ser Gln
        355                 360                 365
Pro Val Thr Pro Glu Lys His Arg Ala Arg Lys Arg Gln Ala Trp Leu
    370                 375                 380
Trp Glu Glu Asp Lys Asn Leu Arg Ser Gly Val Arg Lys Tyr Gly Glu
385                 390                 395                 400
Gly Asn Trp Ser Lys Ile Leu Leu His Tyr Lys Phe Asn Asn Arg Thr
                405                 410                 415
Ser Val Met Leu Lys Asp Arg Trp Arg Thr Met Lys Lys Leu Lys Leu
            420                 425                 430
Ile Ser Ser Asp Ser Glu Asp
        435

(2) INFORMATION FOR SEQ ID NO:13:

(i) SEQUENCE CHARACTERISTICS:
        (A) LENGTH: 52 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

Leu Ile Lys Gly Pro Trp Thr Lys Glu Glu Asp Gln Arg Val Ile Glu
1               5                   10                  15
Leu Val Gln Lys Tyr Gly Pro Lys Arg Trp Ser Leu Ile Ala Lys His
            20                  25                  30
Leu Lys Gly Arg Ile Gly Lys Gln Cys Arg Glu Arg Trp His Asn His
        35                  40                  45
Leu Asn Pro Glu
    50

(2) INFORMATION FOR SEQ ID NO:14:

(i) SEQUENCE CHARACTERISTICS:
        (A) LENGTH: 52 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:14:

Leu Ile Lys Gly Pro Trp Thr Lys Glu Glu Asp Gln Arg Val Ile Lys
1               5                   10                  15

Leu Val Gln Lys Tyr Gly Pro Lys Arg Trp Ser Val Ile Ala Lys His
                20                  25                  30

Leu Lys Gly Arg Ile Gly Lys Gln Cys Arg Glu Arg Trp His Asn His
            35                  40                  45

Leu Asn Pro Glu
        50

(2) INFORMATION FOR SEQ ID NO:15:

(i) SEQUENCE CHARACTERISTICS:
        (A) LENGTH: 53 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

Arg Lys Arg Gln Ala Trp Leu Trp Glu Glu Asp Lys Asn Leu Arg Ser
1               5                   10                  15

Gly Val Arg Lys Tyr Gly Glu Gly Asn Trp Ser Lys Ile Leu Leu His
                20                  25                  30

Tyr Lys Phe Asn Asn Arg Thr Ser Val Met Leu Lys Asp Arg Trp Arg
            35                  40                  45

Thr Met Lys Lys Leu
        50

(2) INFORMATION FOR SEQ ID NO:16:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Val Lys Lys Ser Ser Trp Thr Glu Glu Glu Asp Arg Ile Ile Tyr Glu
1               5                   10                  15

Ala His Lys Arg Leu Gly Asn Arg Trp Ala Glu Ile Ala Lys Leu Leu
                20                  25                  30

Pro Gly Arg Thr Asp Asn Ser Ile Lys Asn His Trp Asn Ser Thr Met
            35                  40                  45

Arg Arg Lys
        50

(2) INFORMATION FOR SEQ ID NO:17:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Val Lys Lys Ser Cys Trp Thr Glu Glu Asp Arg Ile Ile Cys Glu
1               5                   10                  15

Ala His Lys Val Leu Gly Asn Arg Trp Ala Glu Ile Ala Lys Met Leu
            20                  25                  30

Pro Gly Arg Thr Asp Asn Ala Val Lys Asn His Trp Asn Ser Thr Ile
            35                  40                  45

Lys Arg Lys
        50

(2) INFORMATION FOR SEQ ID NO:18:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Val Lys Lys Thr Ser Trp Thr Glu Glu Asp Arg Ile Ile Tyr Gln
1               5                   10                  15

Ala His Lys Arg Leu Gly Asn Arg Trp Ala Glu Ile Ala Lys Leu Leu
            20                  25                  30

Pro Gly Arg Thr Asp Asn Ala Ile Lys Asn His Trp Asn Ser Thr Met
            35                  40                  45

Arg Arg Lys
        50

(2) INFORMATION FOR SEQ ID NO:19:

(i) SEQUENCE CHARACTERISTICS:
        (A) LENGTH: 51 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:19:

Ile Lys Lys Thr Ala Trp Thr Glu Lys Glu Asp Glu Ile Ile Tyr Gln
1               5                   10                  15

Ala His Leu Glu Leu Gly Asn Gln Trp Ala Lys Ile Ala Lys Arg Leu
            20                  25                  30

Pro Gly Arg Thr Asp Asn Ala Ile Lys Asn His Trp Asn Ser Thr Met
            35                  40                  45

Arg Arg Lys
        50

(2) INFORMATION FOR SEQ ID NO:20:

(i) SEQUENCE CHARACTERISTICS:
        (A) LENGTH: 148 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

GTACCCGGGG ATCGTGACTC TAGAGGGGCC CTAACCCTAA CCCTAACCCT AACCCTAACC    60

| | |
|---|---|
| CTAACCCTAA CCCTAACCCT AACCCTAACC CTAACCCTAA CCCTAACCCG GGTCGAATTC | 120 |
| GATCTCTAGA GTCGACCTGC AGGCATGC | 148 |

(2) INFORMATION FOR SEQ ID NO:21:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

| | |
|---|---|
| GTCAAAAACT GACATATGTA TATCGTTCTC AAC | 33 |

(2) INFORMATION FOR SEQ ID NO:22:

(i) SEQUENCE CHARACTERISTICS:
        (A) LENGTH: 1641 base pairs
        (B) TYPE: nucleic acid
        (C) STRANDEDNESS: double
        (D) TOPOLOGY: linear (ii) MOLECULE TYPE: cDNA
        (A) DESCRIPTION: TRF1

(iii) HYPOTHETICAL: NO (vi) ORIGINAL SOURCE:
        (A) ORGANISM: mouse (xi) SEQUENCE DESCRIPTION: SEQ ID NO:22:

| | |
|---|---|
| TTTCGGTTTA ACATGGCGGA GACGGTCTCC TCAGCGGCCC GGGACGCGCC GAGCCGTGAG | 60 |
| GGCTGGACAG ATTCGGATTC TCCAGAGCAG GAGGAGGTGG GAGACGACGC GGAGCTGCTC | 120 |
| CAGTGCCAGC TTCAGCTGGG GACCCCGAGA GAGATGGAGA ACGCGGAGCT TGTGGCTGAG | 180 |
| GTGGAGGCCG TGGCTGCGGG CTGGATGCTC GACTTCCTCT GCCTGTCTCT GTGCCGAGCC | 240 |
| TTCCGCGACG GCCGCTCCGA GGACTTTCGT CGTACTCGTG ACAGCGCCGA GGCTATTATT | 300 |
| CATGGACTAC ACAGACTTAC AGCTTACCAA TTGAAAACTG TGTATATATG TCAGTTTTTG | 360 |
| ACAAGAGTTG CATCTGGAAA GGCCCTTGAT GCACAGTTTG AAGTTGATGA GCGTATTACA | 420 |
| CCCTTGGAAT CAGCCCTGAT GATTTGGAAC TCAATTGAAA AGGAACATGA CAAACTGCAT | 480 |
| GACGAAATAA AGAATTTAAT TAAAATTCAG GCTGTAGCTG TTTGTATGGA AATTGGCAGC | 540 |
| TTTAAGGAAG CAGAAGAAGT ATTTGAAAGA ATATTTGGTG ATCCAGAATT TTACACGCCT | 600 |
| TTAGAAAGGA AGTTACTTAA GATAATCTCT CAGAAGGATG TGTTCCACTC CCTTTTCCAA | 660 |
| CACTTCAGCT ATAGCTGCAT GATGGAGAAA ATTCAGAGTT ATGTGGGTGA TGTGTTAAGT | 720 |
| GAAAAATCAT CAACTTTTCT AATGAAGGCA GCAACAAAAG TAGTGGAAAA TGAGAAAGCG | 780 |
| AGGACACAAG CGTCTAAGGA TAGGCCAGAT GCCACCAACA CTGGAATGGA CACTGAAGTT | 840 |
| GGTTTGAATA AAGAGAAAAG TGTTAATGGC CAGCAGTCTA CAGAAACTGA ACCCTTAGTG | 900 |
| GATACAGTAT CCTCAATAAG GTCTCACAAG AACGCCTTAT CGCAGTTAAA ACACAGACGT | 960 |
| GCTCCATCAG ATTTCAGTAG GAACGAAGCA AGAACAGGAA CTCTTCAGTG TGAAACAACG | 1020 |
| ATGGAAAGGA ACCGAAGAAC CAGTGGAAGG AATAGATTGT GTGTCTCAGA GAATCAGCCA | 1080 |
| GACACTGATG ACAAAAGTGG ACGCAGGAAA AGACAGACAT GGCTTTGGGA AGAAGACAGA | 1140 |
| ATTTTGAAGT GTGGTGTAAA GAAATATGGA GAGGGAAATT GGGCTAAAAT ACTATCCCAT | 1200 |
| TATAAGTTCA ACAACCGAAC AAGTGTCATG TTAAAAGATA GATGGAGAAC AATGAAGAGA | 1260 |

```
CTGAAACTGA TTAGCTGAGA CACTGGAGGC TGGATGGGTT TGATTCANCT TAATACAAGG    1320

ATAAATACTT GGATCACTAC ACTTTGTTTA CAATTTCCTG GTCAGTAATG ATAAAGCATT    1380

ATGGTGGTGG TGGGGCANTT GAGGAGGGGG AAAGAAAAAA GAAATTTTT TGTTTTTTTG     1440

GTTTTTGTTT GTTTGTTTGT TGTTTGTTT TTTAGANGAN ATTTGTTGCT TTAAATCTAT     1500

GTTCATCCAT TATTTTCCTG AATCCTTTAT TTTTGTTAAA ATATAATATG TTTGAACCCT    1560

ACCCAATTCC ATACCCCACC CCATATCCTG TTTTTTAATN CCAAAAATCC AATAAAATT     1620

AAATGAATAT NTGACTATTT A                                              1641
```

(2) INFORMATION FOR SEQ ID NO:23:

(i) SEQUENCE CHARACTERISTICS:
        (A) LENGTH: 421 amino acids
        (B) TYPE: amino acid
        (C) STRANDEDNESS: single
        (D) TOPOLOGY: linear (ii) MOLECULE TYPE: protein
        (A) DESCRIPTION: TRF1

(iii) HYPOTHETICAL: NO (vi) ORIGINAL SOURCE:
        (A) ORGANISM: mouse (xi) SEQUENCE DESCRIPTION: SEQ ID NO:23:

```
Met Ala Glu Thr Val Ser Ser Ala Ala Arg Asp Ala Pro Ser Arg Glu
1               5                   10                  15

Gly Trp Thr Asp Ser Asp Ser Pro Glu Gln Glu Val Gly Asp Asp
            20                  25                  30

Ala Glu Leu Leu Gln Cys Gln Leu Gln Leu Gly Thr Pro Arg Glu Met
        35                  40                  45

Glu Asn Ala Glu Leu Val Ala Glu Val Glu Ala Val Ala Ala Gly Trp
    50                  55                  60

Met Leu Asp Phe Leu Cys Leu Ser Leu Cys Arg Ala Phe Arg Asp Gly
65                  70                  75                  80

Arg Ser Glu Asp Phe Arg Arg Thr Arg Asp Ser Ala Glu Ala Ile Ile
                85                  90                  95

His Gly Leu His Arg Leu Thr Ala Tyr Gln Leu Lys Thr Val Tyr Ile
            100                 105                 110

Cys Gln Phe Leu Thr Arg Val Ala Ser Gly Lys Ala Leu Asp Ala Gln
        115                 120                 125

Phe Glu Val Asp Glu Arg Ile Thr Pro Leu Glu Ser Ala Leu Met Ile
    130                 135                 140

Trp Asn Ser Ile Glu Lys Glu His Asp Lys Leu His Asp Glu Ile Lys
145                 150                 155                 160

Asn Leu Ile Lys Ile Gln Ala Val Ala Val Cys Met Glu Ile Gly Ser
                165                 170                 175

Phe Lys Glu Ala Glu Glu Val Phe Glu Arg Ile Phe Gly Asp Pro Glu
            180                 185                 190

Phe Tyr Thr Pro Leu Glu Arg Lys Leu Leu Lys Ile Ser Gln Lys
        195                 200                 205

Asp Val Phe His Ser Leu Phe Gln His Phe Ser Tyr Ser Cys Met Met
    210                 215                 220

Glu Lys Ile Gln Ser Tyr Val Gly Asp Val Leu Ser Glu Lys Ser Ser
225                 230                 235                 240
```

```
Thr Phe Leu Met Lys Ala Ala Thr Lys Val Val Glu Asn Glu Lys Ala
                245                 250                 255
Arg Thr Gln Ala Ser Lys Asp Arg Pro Asp Ala Thr Asn Thr Gly Met
                260                 265                 270
Asp Thr Glu Val Gly Leu Asn Lys Glu Lys Ser Val Asn Gly Gln Gln
                275                 280                 285
Ser Thr Glu Thr Glu Pro Leu Val Asp Thr Val Ser Ser Ile Arg Ser
                290                 295                 300
His Lys Asn Ala Leu Ser Gln Leu Lys His Arg Arg Ala Pro Ser Asp
305                 310                 315                 320
Phe Ser Arg Asn Glu Ala Arg Thr Gly Thr Leu Gln Cys Glu Thr Thr
                325                 330                 335
Met Glu Arg Asn Arg Arg Thr Ser Gly Arg Asn Arg Leu Cys Val Ser
                340                 345                 350
Glu Asn Gln Pro Asp Thr Asp Asp Lys Ser Gly Arg Arg Lys Arg Gln
                355                 360                 365
Thr Trp Leu Trp Glu Glu Asp Arg Ile Leu Lys Cys Gly Val Lys Lys
                370                 375                 380
Tyr Gly Glu Gly Asn Trp Ala Lys Ile Leu Ser His Tyr Lys Phe Asn
385                 390                 395                 400
Asn Arg Thr Ser Val Met Leu Lys Asp Arg Trp Arg Thr Met Lys Arg
                405                 410                 415
Leu Lys Leu Ile Ser
                420

(2) INFORMATION FOR SEQ ID NO:24:

(i) SEQUENCE CHARACTERISTICS:
        (A) LENGTH: 1324 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
         (A) ORGANISM: chicken (xi) SEQUENCE DESCRIPTION: SEQ ID NO:24:

GAATTCAAGC GGCAGGTGGC GCCAGATTGA AAATGTCGGA AGCGGGGAGG GAGCGGGAGG      60

GGGGTTTGGT TCCGTTCTTG CCTTCAGCGT TGGCAGAAGC TGTGGCCGCG GACTGGGTGC     120

TGGAATTCAG CTGCTGCTGT CTGTGCCGGT ATTTCGTGGA GGAGTGTGAG GCCGAGTTCA     180

GGCGGTGGAG GGACGTGGCG CACGCTGTTT CTAATGGCTT CTCCAAAGTA ACAACGCATC     240

AGAAAAAAAT GGTGTACCTC TGTCAGCTTT TGATAAGAAT TGCAGAAGGA AAAAGACTTG     300

AATGCCACTT TGAAAACAAT ACAACAATTT CGCCTTTGGA GTCTGCTCTG TCTTTTTGGA     360

CTTTACTTGA AAGGGAAGAA AGTAAACTAA ATACACTTCA TGAAGAAATC CGTCGCTTGA     420

TTCAAATTCA GGTTGTAGCA GTCTATATGG AAAAAGGATA TTATAAGGAG GCTGCTGAAG     480

TTCTTGAAAG CTATTCACA GACTCAGAAT CACATAAGCC TTTAAGGATG AAGCTGGCAG      540

CCATAGTCAA AAGCAAGGAT CCATATGTTC CCCTTCTCCA GAGCTTCAGT TACAGTCTTT     600

TGTTAAGTAA AGTCAAGTCT TACGTCAAAC TTTTCCTGAA AGAAAACAGA ACCAACTTCT     660

TACTACAGGC AGCTACAAAA CAAGTGGAGT CTGAAGGAGG GGAAGTNAGA GTGTTGCAAA     720

ACAAAACCTT GAATGTCNAA GAAGAGAGAG AAAATAATTT GGAAGCNAAA CAAAGACCTG     780
```

```
CAGAAGAGCT GCGGAGTACT ACAGATTGGT TAACTGGAGA CATATCATCC AGAGTAAGGC      840

CTCCTTCAAA AAAGGGATGC AGAACAAGCA GCGTTCAGAG GCTGAAAGAC TTGAAAAATG      900

TGGAAGAACG TGGAGATGAT TTGCCTTGTA CCGAAGAAGA CAGCCGTGGA CTTATGAAGA      960

AGATAAGAAA CTGAAATCNG GAGTAAGGGA GTTTGGAGTG GGCACTGGAC TAAAATTCTG     1020

ATCCATGGTG ACTTCCACAA CCGAACCACG TCNTGTTGAA AGATCGGTGG ANAACCTGTG     1080

CCAGATCCAA TAAGGATATG TGAACCTACN TTNAATATTT TTGTGCTTTC CCCACATAAG     1140

GACTATCTAA CTGCNCNAAA GATNATTTNT ATCNCCANAT TNCCCAAACN TGTCCNNNAA     1200

CATGANAAGT GTTTCCATGA CTTAATTTNG CCTCCNTCGC CTCCANAGTT GTTAATTTTT     1260

CCATNTTAAA TCTAGGTGNT TTTTAANAGA TCTTAATTGC NCTTTTACCT NTAATCCCTA     1320

ATCN                                                                  1324
```

(2) INFORMATION FOR SEQ ID NO:25:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (iii) HYPOTHETICAL: NO (v) FRAGMENT TYPE: C-terminal (vi) ORIGINAL SOURCE:
        (A) ORGANISM: chicken (xi) SEQUENCE DESCRIPTION: SEQ ID NO:25:

```
Ala Leu Ser Phe Trp Thr Leu Leu Glu Arg Glu Ser Lys Leu Asn
 1               5                  10                  15

Thr Leu His Glu Glu Ile Arg Arg Leu Ile Gln Ile Gln Val Val Ala
            20                  25                  30

Val Tyr Met Glu Lys Gly Tyr Tyr Lys Glu Ala Ala Glu Val Leu Glu
        35                  40                  45

Arg Leu Phe Thr Asp Ser Glu Ser His Lys Pro Leu Arg Met Lys Leu
    50                  55                  60

Ala Ala Ile Val Lys Ser Lys Asp Pro Tyr Val Pro Leu Leu Gln Ser
65                  70                  75                  80

Phe Ser Tyr Ser Leu Leu Leu Ser Lys Val Lys Ser Tyr Val Lys Leu
                85                  90                  95

Phe Leu Lys Glu Asn Arg Thr Asn Phe Leu Leu Gln Ala Ala Thr Lys
               100                 105                 110

Gln Val Glu Ser
        115
```

(2) INFORMATION FOR SEQ ID NO:26:

(i) SEQUENCE CHARACTERISTICS:
        (A) LENGTH: 2907 base pairs
        (B) TYPE: nucleic acid
        (C) STRANDEDNESS: double
        (D) TOPOLOGY: linear (ii) MOLECULE TYPE: cDNA
        (A) DESCRIPTION: TRF2

(iii) HYPOTHETICAL: NO (vi) ORIGINAL SOURCE:
    (A) ORGANISM: Homo sapiens (xi) SEQUENCE DESCRIPTION: SEQ ID NO:26:

```
GGAATTCGGC ACGAGGGACG GCGGGCCCCG CTTCCGGCCC GGGCGTCGTG CGTGACCCAG     60
CGGCGTCACA GCCGAGGAAG CGGCCCGGCC GGGAGGGCGG GGAGGCGCGC GGCGATCGGA    120
CACGATGGCG GGAGGAGGCG GGAGTAGCGA CGGCAGCGGG CGGGCAGCTG GCAGGCGGGC    180
GTCCCGCAGT AGCGGGCGGG CCCGGCGGGG GCGCCACGAG CCGGGGCTGG GGGGCCCGGC    240
GGAGCGCGGC GCGGGGAGG CACGGCTGGA AGAGGCAGTC AATCGCTGGG TGCTCAAGTT    300
CTACTTCCAC GAGGCGCTGC GGGCCTTTCG GGGTAGCCGG TACGGGGACT TCAGACAGAT    360
CCGGGACATC ATGCAGGCTT TGCTTGTCAG GCCCTTGGGG AAGGAGCACA CCGTGTCCCG    420
ATTGCTGCGG GTTATGCAGT GTCTGTCGCG GATTGAAGAA GGGGAAAATT TAGACTGTTC    480
CTTTGATATG GAGGCTGAGC TCACACCACT GGAATCAGCT ATCAATGTGC TGGAGATGAT    540
TAAAACGGAA TTTACACTGA CAGAAGCAGT GGTCGAATCC AGTAGAAAAC TGGTCAAGGA    600
AGCTGCTGTC ATTATTTGTA TCAAAAACAA AGAATTTGAA AAGGCTTCAA AAATTTTGAA    660
AAAACATATG TCCAAGGACC CCACAACTCA GAAGCTGAGA ATGATCTCC TGAATATTAT    720
TCGAGAAAAG AACTTGGCCC ATCCTGTTAT CCAGAACTTT TCATATGAGA CCTTCCAGCA    780
GAAGATGCTG CGCTTCCTGG AGAGCCACCT GGATGACGCC GAGCCCTACC TCCTCACGAT    840
GGCCAAAAAG GCTTTGAAAT CTGAGTCCGC TGCCTCAAGT ACAGGGAAGG AAGATAAACA    900
GCCAGCACCA GGGCCTGTGG AAAAGCCACC CAGAGAACCC GCAAGGCAGC TACGGAATCC    960
TCCAACCACC ATTGGAATGA TGACTCTGAA AGCAGCTTTC AAGACTCTGT CTGGTGCACA   1020
GGATTCTGAG GCAGCCTTTG CAAAACTGGA CCAGAAGGAT CTGGTTCTTC CTACTCAAGC   1080
TCTCCCAGCA TCACCAGCCC TCAAAAACAA GAGACCCAGA AAAGATGAAA ACGAAAGTTC   1140
AGCCCCGGCT GACGGTGAGG GTGGCTCGGA ACTGCAGCCC AAGAACAAGC GCATGACAAT   1200
AAGCAGATTG GTCTTGGAGG AGGACAGCCA GAGTACTGAG CCCAGCGCAG GCCTCAACTC   1260
CTCCCAGGAG GCCGCTTCAG CGCCACCATC CAAGCCCACC GTTCTCAACC AACCCCTCCC   1320
TGGAGAGAAG AATCCCAAAG TACCCAAAGG CAAGTGGAAC AGCTCTAATG GGGTTGAAGA   1380
AAAGGAGACT TGGGTGGAAG AGGATGAACT GTTTCAAGTT CAGGCAGCAC CAGATGAAGA   1440
CAGTACAACC AATATAACAA AAAGCAGAA GTGGACTGTA GAAGAAAGCG AGTGGGTCAA   1500
GGCTGGAGTG CAGAAATATG GGAAGGAAA CTGGGCTGCC ATTTCTAAAA ATTACCCATT   1560
TGTTAACCGA ACAGCTGTGA TGATTAAGGA TCGCTGGCGG ACCATGAAAA GACTTGGCAT   1620
GAACTGAAAC AGGCTTTCAT TTCCACAGAA TTCACAGGAG CATGGTTCCT AATAATAGCC   1680
CCTGATAGTC TGCTCTTTCT TTCTTTTTCT TTTTTTTTT TTTTGAGAC AGAGTCTCGC   1740
TCTGTCACCC AGGCTGGAGT GCAGTGGCGT GATCTCGGCT CACTGCGACC TCCGTCTCCC   1800
GGGCTCACGC CATTCTCCTG CCTCAGCCTC CGAGTAGCTG GGACTACAGG CGCCCGCCAT   1860
CACGCCCGGC TAATGTTTTG TATTTTTAGT AAANACGGGG TTTCACCGTG TTGGCCAGGA   1920
TGGTCTCGAT CTCCTGACCT CGTGATCCAC CCAACTCGGC CTCCCAAAGT GCTGGGATTA   1980
CAGGCATGAN CCACCGCGCC TGGCATCTGC TGTTTCTTTC AGAAGCTGGG CTGGGATGAG   2040
AATTTTGGGC AACCTCCTTC GACGTGGGGG AGGTCCCATT TCCACTTCAT CACTGTTGGA   2100
GATCATGGAG CTAAGAAGCA GAGCCAAGTC CACCCATGTC CTTGGCAGAG ATGACGGCAC   2160
ACAGCTTGTG CAGTGCCAGA ATATCATTAG CGTTTCCCTT CTTTAGTGGT TTGCTTAAAT   2220
```

```
TTAAATCCCT GGTAATCTGT AGAACCTTCT CCTAGGAAAT GGTGAAGTCT ATTAGGAGCC    2280

ACTTGTGACT CCATGACCTG TTAAAACCAG CAATGTGAGT ATTATTTGGA GTAAATTTGT    2340

TCCACGTCAA GTTCTGGCCT TCTGATGCAA ATGCAAAGGA ACTTAGTNTG TTATGAACCC    2400

AGGTTGATGA CAGACCAGTC CTTGTGGAAT AAGATTCCCT TTAAAAACTC TTTAGCCAGT    2460

CGTGACATCA ACCCTAGACC TGTCTGCCTT GGCATTTGCT GTCAANATNT GCTGGGCTAT    2520

GTAGGCAGGT TAATCCTCCA CTTCTCATGT GGTTGAACCA GTGTGTTTTT TGGTAAAATG    2580

GTGATTGTAG ATAAGATTAG TTCCCTGATC CCCTGCCCCC TGTCCCCTGC CTCTTTTCCC    2640

AATTCCCTTC CTTATGCTGG ACTTTAAAG CTTAAAAAAA ATCCGATTGA ATATAAATGC     2700

CTAATTTCAT TCTTTTGTGA AATGGTTGCT TCCTCCTGAT TCCCTAATTG TGCTGTGTTC    2760

GTGTCTTGCA CTGGAATTCA ACATTCCCTT CTCCTTTTGT ACTGTGTTGT GCTTGCTGTC    2820

TCTCCCGGAC ACCCTAAAG ACTGTCTTTT TAGCAAAAAA TTTCAGTAAA GTGTTTTCTG     2880

TAATCTTTTT TTAAAAAAAA AAAAAA                                        2907
```

(2) INFORMATION FOR SEQ ID NO:27:

(i) SEQUENCE CHARACTERISTICS:
        (A) LENGTH: 500 amino acids
        (B) TYPE: amino acid
        (C) STRANDEDNESS: single
        (D) TOPOLOGY: linear (ii) MOLECULE TYPE: protein
        (A) DESCRIPTION: TRF2

(iii) HYPOTHETICAL: NO (vi) ORIGINAL SOURCE:
        (A) ORGANISM: Homo sapiens (xi) SEQUENCE DESCRIPTION: SEQ ID NO:27:

```
Met Ala Gly Gly Gly Ser Ser Asp Gly Ser Gly Arg Ala Ala Gly
 1               5                  10                  15

Arg Arg Ala Ser Arg Ser Ser Gly Arg Ala Arg Arg Gly Arg His Glu
                20                  25                  30

Pro Gly Leu Gly Gly Pro Ala Glu Arg Gly Ala Gly Glu Ala Arg Leu
            35                  40                  45

Glu Glu Ala Val Asn Arg Trp Val Leu Lys Phe Tyr Phe His Glu Ala
 50                  55                  60

Leu Arg Ala Phe Arg Gly Ser Arg Tyr Gly Asp Phe Arg Gln Ile Arg
 65                  70                  75                  80

Asp Ile Met Gln Ala Leu Leu Val Arg Pro Leu Gly Lys Glu His Thr
                85                  90                  95

Val Ser Arg Leu Leu Arg Val Met Gln Cys Leu Ser Arg Ile Glu Glu
            100                 105                 110

Gly Glu Asn Leu Asp Cys Ser Phe Asp Met Glu Ala Glu Leu Thr Pro
        115                 120                 125

Leu Glu Ser Ala Ile Asn Val Leu Glu Met Ile Lys Thr Glu Phe Thr
    130                 135                 140

Leu Thr Glu Ala Val Val Glu Ser Ser Arg Lys Leu Val Lys Glu Ala
145                 150                 155                 160

Ala Val Ile Ile Cys Ile Lys Asn Lys Glu Phe Glu Lys Ala Ser Lys
                165                 170                 175

Ile Leu Lys Lys His Met Ser Lys Asp Pro Thr Thr Gln Lys Leu Arg
            180                 185                 190
```

```
Asn Asp Leu Leu Asn Ile Ile Arg Glu Lys Asn Leu Ala His Pro Val
        195                 200                 205

Ile Gln Asn Phe Ser Tyr Glu Thr Phe Gln Gln Lys Met Leu Arg Phe
    210                 215                 220

Leu Glu Ser His Leu Asp Asp Ala Glu Pro Tyr Leu Leu Thr Met Ala
225                 230                 235                 240

Lys Lys Ala Leu Lys Ser Glu Ser Ala Ala Ser Ser Thr Gly Lys Glu
                245                 250                 255

Asp Lys Gln Pro Ala Pro Gly Pro Val Glu Lys Pro Pro Arg Glu Pro
                260                 265                 270

Ala Arg Gln Leu Arg Asn Pro Pro Thr Thr Ile Gly Met Met Thr Leu
            275                 280                 285

Lys Ala Ala Phe Lys Thr Leu Ser Gly Ala Gln Asp Ser Glu Ala Ala
        290                 295                 300

Phe Ala Lys Leu Asp Gln Lys Asp Leu Val Leu Pro Thr Gln Ala Leu
305                 310                 315                 320

Pro Ala Ser Pro Ala Leu Lys Asn Lys Arg Pro Arg Lys Asp Glu Asn
                325                 330                 335

Glu Ser Ser Ala Pro Ala Asp Gly Glu Gly Gly Ser Glu Leu Gln Pro
                340                 345                 350

Lys Asn Lys Arg Met Thr Ile Ser Arg Leu Val Leu Glu Glu Asp Ser
            355                 360                 365

Gln Ser Thr Glu Pro Ser Ala Gly Leu Asn Ser Ser Gln Glu Ala Ala
        370                 375                 380

Ser Ala Pro Pro Ser Lys Pro Thr Val Leu Asn Gln Pro Leu Pro Gly
385                 390                 395                 400

Glu Lys Asn Pro Lys Val Pro Lys Gly Lys Trp Asn Ser Ser Asn Gly
                405                 410                 415

Val Glu Glu Lys Glu Thr Trp Val Glu Glu Asp Glu Leu Phe Gln Val
            420                 425                 430

Gln Ala Ala Pro Asp Glu Asp Ser Thr Thr Asn Ile Thr Lys Lys Gln
        435                 440                 445

Lys Trp Thr Val Glu Glu Ser Glu Trp Val Lys Ala Gly Val Gln Lys
    450                 455                 460

Tyr Gly Glu Gly Asn Trp Ala Ala Ile Ser Lys Asn Tyr Pro Phe Val
465                 470                 475                 480

Asn Arg Thr Ala Val Met Ile Lys Asp Arg Trp Arg Thr Met Lys Arg
                485                 490                 495

Leu Gly Met Asn
            500

(2) INFORMATION FOR SEQ ID NO:28:

(i) SEQUENCE CHARACTERISTICS:
        (A) LENGTH: 2119 base pairs
        (B) TYPE: nucleic acid
        (C) STRANDEDNESS: double
        (D) TOPOLOGY: linear (ii) MOLECULE TYPE: cDNA
        (A) DESCRIPTION: TRF2

(iii) HYPOTHETICAL: NO (vi) ORIGINAL SOURCE:
        (A) ORGANISM: mouse
```

-continued (xi) SEQUENCE DESCRIPTION: SEQ ID NO:28:

```
GGAATTCGGC ACGAGCCAGT CGGGAGGGCG GGGAGGGCGG GGAGGGCGAG CGGCGGTCGA          60
ACACGATGGC GGGAGGAGGC GGGAGCAGCG ATAGCAGCGG GCGGGCGGCG AGCCGACGGG         120
CATCGCGCAG CGGCGGGCGG GCTCGACGGG GGCGACACGA GCCAGGGTTG GGAGGCGCGG         180
CCGAGCGGGG CGCGGGGGAA GCTCGCCTGG AGGAGGCGGT CAACCGCTGG GTGCTCAAGT         240
TCTATTTCCA CGAGGCGCTG CGGGCCTTTC GGAGTAGCCG GTACCGGGAC TTCAGGCAGA         300
TCCGGGACAT CATGCAGGCG TTGCTTGTCA GGCCCTTGGG GAAGGAGCAT ACGGTGTCCC         360
GGTTGCTGCG GGTTATGCAG TGTCTGTCGC GCATTGAAGA AGGAGAAAAT TTAGACTGTT         420
CCTTTGATAT GGAGGCTGAG CTCACACCCT TGGAATCAGC TATCAATGTG CTGGAGATGA         480
TTAAAACAGA GTTCACACTG ACAGACTCTA TGGTTGAATC CAGCAGAAAA CTGGTCAAGG         540
AGGCTGCTGT CATTATTTGT ATCAAAAACA AAGAATTTGA AAAGGCTTCA AAGATTTTGA         600
AAAAATACAT GTCTAAGGAC CCCACAACTC AGAAGCTGAG AACTGATCTC CTGAACATTA         660
TCCGGGAAAA GAACTTGGCC CACCCTGTTA TCCAGAACTT TTCCTATGAG GTCTTCCAGC         720
AGAAGATGCT GCGTTTCCTA GAGAGCCACC TGGATGACAC GGAGCCCTAC CTCCTCACGA         780
TGGCTAAAAA AGCTTTGAAA TCTGAATCAG CTGCTTCAAG TACAATGAGG GAAGAAAAGC         840
ACCCAGAGCC AGTGGAAAAA CCACTTAGAG AGCCTCCAAG ACAGCCTCAG AACCCTCCAG         900
CCACCATCGG GATCAGGACT CTGAAGGCAG CTTTCAAAGC TCTGTCTACT GCACAAGACT         960
CAGAGGCCGC TTTTGCAAAA CTGGACCAGA AGATCTGGT ACTTGCTAAT CTGGCATCCC        1020
CATCATCACC AGCCCACAAA CACAAGAGAC CCAGGAAAGA TGAACATGAA AGCGCAGCTC        1080
CTGCTGAGGG TGAGGGAGGC TCGAGCCGGC AGCCCAGGAA CAGTCCCATG ACAATAAGCA        1140
GATTGCTGTT GGAGGAGGAC AGCCAGAGTA CTGAGCCCAG CCCAGGCCTC AACTCCTCCC        1200
ACGAGGCCAT GTCAGCATCC AAGCCCAGAG CTCTCAACCA ACCCCACCCG GGGGAGAAGA        1260
AGCCCAAAGC ATCCAAAGAC AAGTGGAACA GCCCTAACGG GCTTGAAGAA AAGGAAGTTT        1320
GGTTGGAAGA GGACCAGCTG TTTGAAGTTC AGGCACCAGG TGAAGACAGG TCATCCAGTT        1380
TAACAAGAAA GCAGAAGTGG ACCATAGAAG AAAGCGAGTG GGTGAAGGAT GGAGTGCGCA        1440
AATACGGGGA AGGAAACTGG GCTGCCATTT CTAAAAGTTA CCCCTTTGTC AACCGAACAG        1500
CTGTGATGAT TAAAGACCGC TGGCGGACCA TGAAAAAACT TGGCATGAAC TGAGAAAGGG        1560
TTTCGTAGCC ACAGGACTCA CAAGAACACG GTTCTCAACA GTAGCCCCTG TGCTGTGACG        1620
CCTCTTTCAG AAGCGGGACT GCGATGAGAA TTGTGGCATC NTCCTCCTGA GTCGGAGGTC        1680
CCGGGACCCT CCCGTCACTG TTGCTGGAGA TCATGGAGCT AAAAAGCAAA GCCAGGACTA        1740
GCCGTGACCA CAGCCGAGGC AACAGGCAGG CCCACGGCTG GGACAGTGCC AGAAGATCAT        1800
TAGTGTTTCC CTTTAGTGCT TTGCTTCAAT TTGAATCCCT AGTATTCCGT AAAATCTTCC        1860
AAGAAATGAT AGAATCCATT AGGAGCACAT ACGATCTCAT GACCTGTAAA AACCAGAAAT        1920
GTGAACGTTA CCGGGAATGA ATTTAATCCT CGTTGAGTTT CAGTACAAAA GAGCTCTGTA        1980
TGTTGAGCCC AGATGAGAGA TTTTTTCGTC CCTGTGGAAT CAGATCTTTA AAAAAAAAAA        2040
AAAAAAAAAA AAACTCGAGG GGGGGCCCTA TTCTATAGTG TCACTAAATT GCTAAANCTC        2100
NCTGATCACC TCGANTGTN                                                    2119
```

(2) INFORMATION FOR SEQ ID NO:29:

(i) SEQUENCE CHARACTERISTICS:
        (A) LENGTH: 495 amino acids
        (B) TYPE: amino acid
        (C) STRANDEDNESS: single
        (D) TOPOLOGY: linear (ii) MOLECULE TYPE: protein
        (A) DESCRIPTION: TRF2

(iii) HYPOTHETICAL: NO (vi) ORIGINAL SOURCE:
        (A) ORGANISM: mouse (xi) SEQUENCE DESCRIPTION: SEQ ID NO:29:

```
Met Ala Gly Gly Gly Ser Ser Asp Ser Ser Gly Arg Ala Ala Ser
 1               5                  10                  15

Arg Arg Ala Ser Arg Ser Gly Gly Arg Ala Arg Arg Gly Arg His Glu
            20                  25                  30

Pro Gly Leu Gly Gly Ala Ala Glu Arg Gly Ala Gly Glu Ala Arg Leu
            35                  40                  45

Glu Glu Ala Val Asn Arg Trp Val Leu Lys Phe Tyr Phe His Glu Ala
        50                  55                  60

Leu Arg Ala Phe Arg Ser Ser Arg Tyr Arg Asp Phe Arg Gln Ile Arg
65                  70                  75                  80

Asp Ile Met Gln Ala Leu Leu Val Arg Pro Leu Gly Lys Glu His Thr
                85                  90                  95

Val Ser Arg Leu Leu Arg Val Met Gln Cys Leu Ser Arg Ile Glu Glu
                100                 105                 110

Gly Glu Asn Leu Asp Cys Ser Phe Asp Met Glu Ala Glu Leu Thr Pro
            115                 120                 125

Leu Glu Ser Ala Ile Asn Val Leu Glu Met Ile Lys Thr Glu Phe Thr
        130                 135                 140

Leu Thr Asp Ser Met Val Glu Ser Ser Arg Lys Leu Val Lys Glu Ala
145                 150                 155                 160

Ala Val Ile Ile Cys Ile Lys Asn Lys Glu Phe Glu Lys Ala Ser Lys
                165                 170                 175

Ile Leu Lys Lys Tyr Met Ser Lys Asp Pro Thr Thr Gln Lys Leu Arg
                180                 185                 190

Thr Asp Leu Leu Asn Ile Ile Arg Glu Lys Asn Leu Ala His Pro Val
            195                 200                 205

Ile Gln Asn Phe Ser Tyr Glu Val Phe Gln Gln Lys Met Leu Arg Phe
        210                 215                 220

Leu Glu Ser His Leu Asp Asp Thr Glu Pro Tyr Leu Leu Thr Met Ala
225                 230                 235                 240

Lys Lys Ala Leu Lys Ser Glu Ser Ala Ala Ser Ser Thr Met Arg Glu
                245                 250                 255

Glu Lys His Pro Glu Pro Val Glu Lys Pro Leu Arg Glu Pro Pro Arg
                260                 265                 270

Gln Pro Gln Asn Pro Pro Ala Thr Ile Gly Ile Arg Thr Leu Lys Ala
            275                 280                 285

Ala Phe Lys Ala Leu Ser Thr Ala Gln Asp Ser Glu Ala Ala Phe Ala
        290                 295                 300

Lys Leu Asp Gln Lys Asp Leu Val Leu Ala Asn Leu Ala Ser Pro Ser
305                 310                 315                 320
```

```
Ser Pro Ala His Lys His Lys Arg Pro Arg Lys Asp Glu His Glu Ser
            325                 330                 335
Ala Ala Pro Ala Glu Gly Glu Gly Ser Ser Arg Gln Pro Arg Asn
            340                 345                 350
Ser Pro Met Thr Ile Ser Arg Leu Leu Leu Glu Glu Asp Ser Gln Ser
            355                 360                 365
Thr Glu Pro Ser Pro Gly Leu Asn Ser Ser His Glu Ala Met Ser Ala
        370                 375                 380
Ser Lys Pro Arg Ala Leu Asn Gln Pro His Pro Gly Glu Lys Lys Pro
385                 390                 395                 400
Lys Ala Ser Lys Asp Lys Trp Asn Ser Pro Asn Gly Leu Glu Glu Lys
            405                 410                 415
Glu Val Trp Leu Glu Glu Asp Gln Leu Phe Glu Val Gln Ala Pro Gly
            420                 425                 430
Glu Asp Arg Ser Ser Ser Leu Thr Arg Lys Gln Lys Trp Thr Ile Glu
            435                 440                 445
Glu Ser Glu Trp Val Lys Asp Gly Val Arg Lys Tyr Gly Glu Gly Asn
        450                 455                 460
Trp Ala Ala Ile Ser Lys Ser Tyr Pro Phe Val Asn Arg Thr Ala Val
465                 470                 475                 480
Met Ile Lys Asp Arg Trp Arg Thr Met Lys Lys Leu Gly Met Asn
10              485                 490                 495

(2) INFORMATION FOR SEQ ID NO:30:

(i) SEQUENCE CHARACTERISTICS:
        (A) LENGTH: 1341 base pairs
        (B) TYPE: nucleic acid
        (C) STRANDEDNESS: double
        (D) TOPOLOGY: linear (ii) MOLECULE TYPE: cDNA
         (A) DESCRIPTION: TRF2

(iii) HYPOTHETICAL: NO (vi) ORIGINAL SOURCE:
         (A) ORGANISM: mouse (xi) SEQUENCE DESCRIPTION: SEQ ID NO:30:

GAGGCGGTCA ACCGCTGGGT GCTCAAGTTC TATTTCCACG AGGCGCTGCG GGCCTTTCGG       60

AGTAGCCGGT ACCGGGACTT CAGGCAGATC CGGGACATCA TGCAGGCGTT GCTTGTCAGG      120

CCCTTGGGGA AGGAGCATAC GGTGTCCCGG TTGCTGCGGG TTATGCAGTG TCTGTCGCGC      180

ATTGAAGAAG GAGAAAATTT AGACTGTTCC TTTGATATGG AGGCTGAGCT CACACCCTTG      240

GAATCAGCTA TCAATGTGCT GGAGATGATT AAAACAGAGT TCACACTGAC AGACTCTATG      300

GTTGAATCCA GCAGAAAACT GGTCAAGGAG GCTGCTGTCA TTATTTGTAT CAAAAACAAA      360

GAATTTGAAA AGGCTTCAAA GATTTTGAAA AAATACATGT CTAAGGACCC CACAACTCAG      420

AAGCTGAGAA CTGATCTCCT GAACATTATC CGGGAAAAGA ACTTGGCCCA CCCTGTTATC      480

CAGAACTTTT CCTATGAGGT CTTCCAGCAG AAGATGCTGC GTTTCCTAGA GAGCCACCTG      540

GATGACACGG AGCCCTACCT CCTCACGATG GCTAAAAAAG CTTTGAAATC TGAATCAGCT      600

GCTTCAAGTA CAATGAGGGA AGAAAAGCAC CCAGAGCCAG TGGAAAAACC ACTTAGAGAG      660

CCTCCAAGAC AGCCTCAGAA CCCTCCAGCC ACCATCGGGA TCAGGACTCT GAAGGCAGCT      720

TTCAAAGCTC TGTCTACTGC ACAAGACTCA GAGGCCGCTT TGCAAAACT GGACCAGAAA      780

GATCTGGTAC TTGCTAATCT GGCATCCCCA TCATCACCAG CCCACAAACA CAAGAGACCC      840
```

```
AGGAAAGATG AACATGAAAG CGCAGCTCCT GCTGAGGGTG AGGGAGGCTC GAGCCGGCAG    900

CCCAGGAACA GTCCCATGAC AATAAGCAGA TTGCTGTTGG AGGAGGACAG CCAGAGTACT    960

GAGCCCAGCC CAGGCCTCAA CTCCTCCCAC GAGGCCATGT CAGCATCCAA GCCCAGAGCT   1020

CTCAACCAAC CCCACCCGGG GGAGAAGAAG CCCAAAGCAT CCAAAGACAA GTGGAACAGC   1080

CCTAACGGGC TTGAAGAAAA GGAAGTTTGG TTGGAAGAGG ACCAGCTGTT TGAAGTTCAG   1140

GCACCAGGTG AAGACAGGTC ATCCAGTTTA ACAAGAAAGC AGAAGTGGAC CATAGAAGAA   1200

AGCGAGTGGG TGAAGGATGG AGTGCGCAAA TACGGGAAG  GAAACTGGGC TGCCATTTCT   1260

AAAAGTTACC CCTTTGTCAA CCGAACAGCT GTGATGATTA AAGACCGCTG GCGGACCATG   1320

AAAAAACTTG GCATGAACTG A                                             1341
```

(2) INFORMATION FOR SEQ ID NO:31:

(i) SEQUENCE CHARACTERISTICS:
        (A) LENGTH: 446 amino acids
        (B) TYPE: amino acid
        (C) STRANDEDNESS: single
        (D) TOPOLOGY: linear (ii) MOLECULE TYPE: protein
        (A) DESCRIPTION: TRF2

(iii) HYPOTHETICAL: NO (vi) ORIGINAL SOURCE:
        (A) ORGANISM: mouse (xi) SEQUENCE DESCRIPTION: SEQ ID NO:31:

```
Glu Ala Val Asn Arg Trp Val Leu Lys Phe Tyr Phe His Glu Ala Leu
 1               5                  10                  15

Arg Ala Phe Arg Ser Ser Arg Tyr Arg Asp Phe Arg Gln Ile Arg Asp
            20                  25                  30

Ile Met Gln Ala Leu Leu Val Arg Pro Leu Gly Lys Glu His Thr Val
        35                  40                  45

Ser Arg Leu Leu Arg Val Met Gln Cys Leu Ser Arg Ile Glu Glu Gly
    50                  55                  60

Glu Asn Leu Asp Cys Ser Phe Asp Met Glu Ala Glu Leu Thr Pro Leu
65                  70                  75                  80

Glu Ser Ala Ile Asn Val Leu Glu Met Ile Lys Thr Glu Phe Thr Leu
                85                  90                  95

Thr Asp Ser Met Val Glu Ser Ser Arg Lys Leu Val Lys Glu Ala Ala
            100                 105                 110

Val Ile Ile Cys Ile Lys Asn Lys Glu Phe Glu Lys Ala Ser Lys Ile
        115                 120                 125

Leu Lys Lys Tyr Met Ser Lys Asp Pro Thr Thr Gln Lys Leu Arg Thr
    130                 135                 140

Asp Leu Leu Asn Ile Ile Arg Glu Lys Asn Leu Ala His Pro Val Ile
145                 150                 155                 160

Gln Asn Phe Ser Tyr Glu Val Phe Gln Gln Lys Met Leu Arg Phe Leu
                165                 170                 175

Glu Ser His Leu Asp Asp Thr Glu Pro Tyr Leu Leu Thr Met Ala Lys
            180                 185                 190

Lys Ala Leu Lys Ser Glu Ser Ala Ala Ser Ser Thr Met Arg Glu Glu
        195                 200                 205

Lys His Pro Glu Pro Val Glu Lys Pro Leu Arg Glu Pro Pro Arg Gln
    210                 215                 220
```

```
Pro Gln Asn Pro Pro Ala Thr Ile Gly Ile Arg Thr Leu Lys Ala Ala
225                 230                 235                 240

Phe Lys Ala Leu Ser Thr Ala Gln Asp Ser Glu Ala Ala Phe Ala Lys
                245                 250                 255

Leu Asp Gln Lys Asp Leu Val Leu Ala Asn Leu Ala Ser Pro Ser Ser
                260                 265                 270

Pro Ala His Lys His Lys Arg Pro Arg Lys Asp Glu His Glu Ser Ala
                275                 280                 285

Ala Pro Ala Glu Gly Glu Gly Gly Ser Ser Arg Gln Pro Arg Asn Ser
290                 295                 300

Pro Met Thr Ile Ser Arg Leu Leu Leu Glu Glu Asp Ser Gln Ser Thr
305                 310                 315                 320

Glu Pro Ser Pro Gly Leu Asn Ser Ser His Glu Ala Met Ser Ala Ser
                325                 330                 335

Lys Pro Arg Ala Leu Asn Gln Pro His Pro Gly Glu Lys Lys Pro Lys
                340                 345                 350

Ala Ser Lys Asp Lys Trp Asn Ser Pro Asn Gly Leu Glu Glu Lys Glu
                355                 360                 365

Val Trp Leu Glu Glu Asp Gln Leu Phe Glu Val Gln Ala Pro Gly Glu
                370                 375                 380

Asp Arg Ser Ser Ser Leu Thr Arg Lys Gln Lys Trp Thr Ile Glu Glu
385                 390                 395                 400

Ser Glu Trp Val Lys Asp Gly Val Arg Lys Tyr Gly Glu Gly Asn Trp
                405                 410                 415

Ala Ala Ile Ser Lys Ser Tyr Pro Phe Val Asn Arg Thr Ala Val Met
                420                 425                 430

Ile Lys Asp Arg Trp Arg Thr Met Lys Lys Leu Gly Met Asn
                435                 440                 445

(2) INFORMATION FOR SEQ ID NO:32:

(i) SEQUENCE CHARACTERISTICS:
        (A) LENGTH: 201 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: human (xi) SEQUENCE DESCRIPTION: SEQ ID NO:32:

ATGGCGGAGG ATGTTTCCTC AGCGGCCCCG AGCCCGCGGC GGTGTGCGGA TGGTAGGGAT      60

GCCGACCCTA CTGAGGAGCA GATGGCAGAA ACAGAGAGAA ACGACGAGGA GCAGTTCGAA     120

TGCCAGGAAC TGCTCGAGTG CCAGGTGCAG GTGGGGGCCC CCGAGGAGGA GGAGGAGGAG     180

GAGGAGGACG CGGGCCTGGT G                                               201

(2) INFORMATION FOR SEQ ID NO:33:

(i) SEQUENCE CHARACTERISTICS:
        (A) LENGTH: 67 amino acids
        (B) TYPE: amino acid
        (C) STRANDEDNESS: single
        (D) TOPOLOGY: linear (ii) MOLECULE TYPE: protein
```

```
       (iii) HYPOTHETICAL: NO (vi) ORIGINAL SOURCE:
            (A) ORGANISM: Homo sapiens (xi) SEQUENCE DESCRIPTION: SEQ ID NO:33:

Met Ala Glu Asp Val Ser Ser Ala Ala Pro Ser Pro Arg Arg Cys Ala
1               5                  10                  15

Asp Gly Arg Asp Ala Asp Pro Thr Glu Glu Gln Met Ala Glu Thr Glu
            20                  25                  30

Arg Asn Asp Glu Glu Gln Phe Glu Cys Gln Glu Leu Leu Glu Cys Gln
        35                  40                  45

Val Gln Val Gly Ala Pro Glu Glu Glu Glu Glu Glu Glu Asp Ala
    50                  55                  60

Gly Leu Val
65

(2) INFORMATION FOR SEQ ID NO:34:

(i) SEQUENCE CHARACTERISTICS:
            (A) LENGTH: 162 base pairs
            (B) TYPE: nucleic acid
            (C) STRANDEDNESS: double
            (D) TOPOLOGY: linear (ii) MOLECULE TYPE: cDNA
            (A) DESCRIPTION: TRF1

(iii) HYPOTHETICAL: NO (vi) ORIGINAL SOURCE:
            (A) ORGANISM: mouse (xi) SEQUENCE DESCRIPTION: SEQ ID NO:34:

ATGGCGGAGA CGGTCTCCTC AGCGGCCCGG GACGCGCCGA GCCGTGAGGG CTGGACAGAT        60

TCGGATTCTC CAGAGCAGGA GGAGGTGGGA GACGACGCGG AGCTGCTCCA GTGCCAGCTT       120

CAGCTGGGGA CCCCGAGAGA GATGGAGAAC GCGGAGCTTG TG                         162

(2) INFORMATION FOR SEQ ID NO:35:

(i) SEQUENCE CHARACTERISTICS:
            (A) LENGTH: 54 amino acids
            (B) TYPE: amino acid
            (C) STRANDEDNESS: single
            (D) TOPOLOGY: linear (ii) MOLECULE TYPE: protein
            (A) DESCRIPTION: TRF1

(iii) HYPOTHETICAL: NO (vi) ORIGINAL SOURCE:
            (A) ORGANISM: mouse (xi) SEQUENCE DESCRIPTION: SEQ ID NO:35:

Met Ala Glu Thr Val Ser Ser Ala Ala Arg Asp Ala Pro Ser Arg Glu
1               5                  10                  15

Gly Trp Thr Asp Ser Asp Ser Pro Glu Gln Glu Glu Val Gly Asp Asp
            20                  25                  30

Ala Glu Leu Leu Gln Cys Gln Leu Gln Leu Gly Thr Pro Arg Glu Met
        35                  40                  45

Glu Asn Ala Glu Leu Val
    50
```

```
(2) INFORMATION FOR SEQ ID NO:36:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: cDNA
        (A) DESCRIPTION: TRF2

(iii) HYPOTHETICAL: NO (vi) ORIGINAL SOURCE:
        (A) ORGANISM: Homo sapiens (xi) SEQUENCE DESCRIPTION: SEQ ID NO:36:

ATGGCGGGAG GAGGCGGGAG TAGCGACGGC AGCGGGCGGG CAGCTGGCAG GCGGGCGTCC     60

CGCAGTAGCG GGCGGGCCCG GCGGGGGCGC CACGAGCCGG GGCTGGGGGG CCCGGCGGAG    120

CGCGGCGCGG GGGAG                                                    135

(2) INFORMATION FOR SEQ ID NO:37:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein
        (A) DESCRIPTION: TRF2

(iii) HYPOTHETICAL: NO (vi) ORIGINAL SOURCE:
        (A) ORGANISM: Homo sapiens (xi) SEQUENCE DESCRIPTION: SEQ ID NO:37:

Met Ala Gly Gly Gly Gly Ser Ser Asp Gly Ser Gly Arg Ala Ala Gly
 1               5                  10                  15

Arg Arg Ala Ser Arg Ser Ser Gly Arg Ala Arg Arg Gly Arg His Glu
            20                  25                  30

Pro Gly Leu Gly Gly Pro Ala Glu Arg Gly Ala Gly Glu
        35                  40                  45

(2) INFORMATION FOR SEQ ID NO:38:

(i) SEQUENCE CHARACTERISTICS:
        (A) LENGTH: 135 base pairs
        (B) TYPE: nucleic acid
        (C) STRANDEDNESS: double
        (D) TOPOLOGY: linear (ii) MOLECULE TYPE: cDNA
        (A) DESCRIPTION: TRF2

(iii) HYPOTHETICAL: NO (vi) ORIGINAL SOURCE:
        (A) ORGANISM: mouse (xi) SEQUENCE DESCRIPTION: SEQ ID NO:38:

ATGGCGGGAG GAGGCGGGAG CAGCGATAGC AGCGGGCGGG CGGCGAGCCG ACGGGCATCG     60

CGCAGCGGCG GGCGGGCTCG ACGGGGGCGA CACGAGCCAG GGTTGGGAGG CGCGGCCGAG    120

CGGGGCGCGG GGGAA                                                    135
```

(2) INFORMATION FOR SEQ ID NO:39:

(i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein
        (A) DESCRIPTION: TRF2

(iii) HYPOTHETICAL: NO (vi) ORIGINAL SOURCE:
        (A) ORGANISM: mouse (xi) SEQUENCE DESCRIPTION: SEQ ID NO:39:

```
Met Ala Gly Gly Gly Ser Ser Asp Ser Ser Gly Arg Ala Ala Ser
 1               5                  10                  15

Arg Arg Ala Ser Arg Ser Gly Gly Arg Ala Arg Arg Gly Arg His Glu
             20                  25                  30

Pro Gly Leu Gly Gly Ala Ala Glu Arg Gly Ala Gly Glu
         35                  40                  45
```

(2) INFORMATION FOR SEQ ID NO:40:

(i) SEQUENCE CHARACTERISTICS:
        (A) LENGTH: 591 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: Homo sapiens (xi) SEQUENCE DESCRIPTION: SEQ ID NO:40:

```
GCCGAGGCCG AGGCCGTGGC TGCCGGCTGG ATGCTCGATT TCCTCTGCCT CTCTCTTTGC      60

CGAGCTTTCC GCGACGGCCG CTCCGAGGAC TTCCGCAGGA CCCGCAACAG CGCAGAGGCT     120

ATTATTCATG GACTATCCAG TCTAACAGCT TGCCAGTTGA GAACGATATA CATATGTCAG     180

TTTTTGACAA GAATTGCAGC AGGAAAAACC CTTGATGCAC AGTTTGAAAA TGATGAACGA     240

ATTACACCCT TGGAATCAGC CCTGATGATT TGGGGTTCAA TTGAAAAGGA ACATGACAAA     300

CTTCATGAAG AAATACAGAA TTTAATTAAA ATTCAGGCTA TAGCTGTTTG TATGGAAAAT     360

GGCAACTTTA AGAAGCAGA AGAAGTCTTT GAAAGAATAT TTGGTGATCC AAATTCTCAT      420

ATGCCTTTCA AAAGCAAATT GCTTATGATA ATCTCTCAGA AGATACATT TCATTCCTTT      480

TTTCAACACT TCAGCTACAA CCACATGATG GAGAAAATTA AGAGTTATGT GAATTATGTG     540

CTAAGTGAAA AATCATCAAC CTTTCTAATG AAGGCAGCGG CAAAAGTAGT A              591
```

(2) INFORMATION FOR SEQ ID NO:41:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
    (A) ORGANISM: Homo sapiens (xi) SEQUENCE DESCRIPTION: SEQ ID NO:41:

```
Ala Glu Ala Glu Ala Val Ala Ala Gly Trp Met Leu Asp Phe Leu Cys
1               5                  10                  15

Leu Ser Leu Cys Arg Ala Phe Arg Asp Gly Arg Ser Glu Asp Phe Arg
            20                  25                  30

Arg Thr Arg Asn Ser Ala Glu Ala Ile Ile His Gly Leu Ser Ser Leu
        35                  40                  45

Thr Ala Cys Gln Leu Arg Thr Ile Tyr Ile Cys Gln Phe Leu Thr Arg
    50                  55                  60

Ile Ala Ala Gly Lys Thr Leu Asp Ala Gln Phe Glu Asn Asp Glu Arg
65                  70                  75                  80

Ile Thr Pro Leu Glu Ser Ala Leu Met Ile Trp Gly Ser Ile Glu Lys
                85                  90                  95

Glu His Asp Lys Leu His Glu Ile Gln Asn Leu Ile Lys Ile Gln
                100                 105                 110

Ala Ile Ala Val Cys Met Glu Asn Gly Asn Phe Lys Glu Ala Glu Glu
        115                 120                 125

Val Phe Glu Arg Ile Phe Gly Asp Pro Asn Ser His Met Pro Phe Lys
130                 135                 140

Ser Lys Leu Leu Met Ile Ile Ser Gln Lys Asp Thr Phe His Ser Phe
145                 150                 155                 160

Phe Gln His Phe Ser Tyr Asn His Met Met Glu Lys Ile Lys Ser Tyr
                165                 170                 175

Val Asn Tyr Val Leu Ser Glu Lys Ser Ser Thr Phe Leu Met Lys Ala
                180                 185                 190

Ala Ala Lys Val Val
        195
```

(2) INFORMATION FOR SEQ ID NO:42:

(i) SEQUENCE CHARACTERISTICS:
       (A) LENGTH: 591 base pairs
       (B) TYPE: nucleic acid
       (C) STRANDEDNESS: double
       (D) TOPOLOGY: linear (ii) MOLECULE TYPE: cDNA
        (A) DESCRIPTION: TRF1

(iii) HYPOTHETICAL: NO (vi) ORIGINAL SOURCE:
        (A) ORGANISM: mouse (xi) SEQUENCE DESCRIPTION: SEQ ID NO:42:

```
GCTGAGGTGG AGGCCGTGGC TGCGGGCTGG ATGCTCGACT TCCTCTGCCT GTCTCTGTGC    60

CGAGCCTTCC GCGACGGCCG CTCCGAGGAC TTTCGTCGTA CTCGTGACAG CGCCGAGGCT   120

ATTATTCATG GACTACACAG ACTTACAGCT TACCAATTGA AAACTGTGTA TATATGTCAG   180

TTTTTGACAA GAGTTGCATC TGGAAAGGCC CTTGATGCAC AGTTTGAAGT TGATGAGCGT   240

ATTACACCCT TGGAATCAGC CCTGATGATT TGGAACTCAA TTGAAAAGGA ACATGACAAA   300

CTGCATGACG AAATAAAGAA TTTAATTAAA ATTCAGGCTG TAGCTGTTTG TATGGAAATT   360

GGCAGCTTTA AGGAAGCAGA AGAAGTATTT GAAAGAATAT TTGGTGATCC AGAATTTTAC   420

ACGCCTTTAG AAAGGAAGTT ACTTAAGATA ATCTCTCAGA AGGATGTGTT CCACTCCCTT   480
```

```
TTCCAACACT TCAGCTATAG CTGCATGATG GAGAAAATTC AGAGTTATGT GGGTGATGTG      540

TTAAGTGAAA AATCATCAAC TTTTCTAATG AAGGCAGCAA CAAAAGTAGT G              591
```

(2) INFORMATION FOR SEQ ID NO:43:

(i) SEQUENCE CHARACTERISTICS:
        (A) LENGTH: 197 amino acids
        (B) TYPE: amino acid
        (C) STRANDEDNESS: single
        (D) TOPOLOGY: linear (ii) MOLECULE TYPE: protein
        (A) DESCRIPTION: TRF1

(iii) HYPOTHETICAL: NO (vi) ORIGINAL SOURCE:
        (A) ORGANISM: mouse (xi) SEQUENCE DESCRIPTION: SEQ ID NO:43:

```
Ala Glu Val Glu Ala Val Ala Ala Gly Trp Met Leu Asp Phe Leu Cys
 1               5                  10                  15

Leu Ser Leu Cys Arg Ala Phe Arg Asp Gly Arg Ser Glu Asp Phe Arg
             20                  25                  30

Arg Thr Arg Asp Ser Ala Glu Ala Ile Ile His Gly Leu His Arg Leu
         35                  40                  45

Thr Ala Tyr Gln Leu Lys Thr Val Tyr Ile Cys Gln Phe Leu Thr Arg
     50                  55                  60

Val Ala Ser Gly Lys Ala Leu Asp Ala Gln Phe Glu Val Asp Glu Arg
65                  70                  75                  80

Ile Thr Pro Leu Glu Ser Ala Leu Met Ile Trp Asn Ser Ile Glu Lys
                 85                  90                  95

Glu His Asp Lys Leu His Asp Glu Ile Lys Asn Leu Ile Lys Ile Gln
            100                 105                 110

Ala Val Ala Val Cys Met Glu Ile Gly Ser Phe Lys Glu Ala Glu Glu
        115                 120                 125

Val Phe Glu Arg Ile Phe Gly Asp Pro Glu Phe Tyr Thr Pro Leu Glu
    130                 135                 140

Arg Lys Leu Leu Lys Ile Ile Ser Gln Lys Asp Val Phe His Ser Leu
145                 150                 155                 160

Phe Gln His Phe Ser Tyr Ser Cys Met Met Glu Lys Ile Gln Ser Tyr
                165                 170                 175

Val Gly Asp Val Leu Ser Glu Lys Ser Ser Thr Phe Leu Met Lys Ala
            180                 185                 190

Ala Thr Lys Val Val
        195
```

(2) INFORMATION FOR SEQ ID NO:44:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: cDNA
        (A) DESCRIPTION: TRF2

(iii) HYPOTHETICAL: NO (vi) ORIGINAL SOURCE:
        (A) ORGANISM: Homo sapiens

-continued (xi) SEQUENCE DESCRIPTION: SEQ ID NO:44:

```
GCACGGCTGG AAGAGGCAGT CAATCGCTGG GTGCTCAAGT TCTACTTCCA CGAGGCGCTG      60

CGGGCCTTTC GGGGTAGCCG GTACGGGGAC TTCAGACAGA TCCGGGACAT CATGCAGGCT     120

TTGCTTGTCA GGCCCTTGGG GAAGGAGCAC ACCGTGTCCC GATTGCTGCG GGTTATGCAG     180

TGTCTGTCGC GGATTGAAGA AGGGGAAAAT TTAGACTGTT CCTTTGATAT GGAGGCTGAG     240

CTCACACCAC TGGAATCAGC TATCAATGTG CTGGAGATGA TTAAAACGGA ATTTACACTG     300

ACAGAAGCAG TGGTCGAATC CAGTAGAAAA CTGGTCAAGG AAGCTGCTGT CATTATTTGT     360

ATCAAAAACA AGAATTTGA AAAGGCTTCA AAAATTTTGA AAAAACATAT GTCCAAGGAC      420

CCCACAACTC AGAAGCTGAG AAATGATCTC CTGAATATTA TTCGAGAAAA GAACTTGGCC     480

CATCCTGTTA TCCAGAACTT TTCATATGAG ACCTTCCAGC AGAAGATGCT GCGCTTCCTG     540

GAGAGCCACC TGGATGACGC CGAGCCCTAC CTCCTCACGA TGGCCAAAAA GGCTTTGAAA     600
```

(2) INFORMATION FOR SEQ ID NO:45:

(i) SEQUENCE CHARACTERISTICS:
       (A) LENGTH: 200 amino acids
       (B) TYPE: amino acid
       (C) STRANDEDNESS: single
       (D) TOPOLOGY: linear (ii) MOLECULE TYPE: protein
        (A) DESCRIPTION: TRF2

(iii) HYPOTHETICAL: NO (vi) ORIGINAL SOURCE:
        (A) ORGANISM: Homo sapiens (xi) SEQUENCE DESCRIPTION: SEQ ID NO:45:

```
Ala Arg Leu Glu Glu Ala Val Asn Arg Trp Val Leu Lys Phe Tyr Phe
 1               5                  10                  15

His Glu Ala Leu Arg Ala Phe Arg Gly Ser Arg Tyr Gly Asp Phe Arg
            20                  25                  30

Gln Ile Arg Asp Ile Met Gln Ala Leu Leu Val Arg Pro Leu Gly Lys
        35                  40                  45

Glu His Thr Val Ser Arg Leu Leu Arg Val Met Gln Cys Leu Ser Arg
    50                  55                  60

Ile Glu Glu Gly Glu Asn Leu Asp Cys Ser Phe Asp Met Glu Ala Glu
65                  70                  75                  80

Leu Thr Pro Leu Glu Ser Ala Ile Asn Val Leu Glu Met Ile Lys Thr
                85                  90                  95

Glu Phe Thr Leu Thr Glu Ala Val Val Glu Ser Ser Arg Lys Leu Val
            100                 105                 110

Lys Glu Ala Ala Val Ile Ile Cys Ile Lys Asn Lys Glu Phe Glu Lys
        115                 120                 125

Ala Ser Lys Ile Leu Lys Lys His Met Ser Lys Asp Pro Thr Thr Gln
    130                 135                 140

Lys Leu Arg Asn Asp Leu Leu Asn Ile Ile Arg Glu Lys Asn Leu Ala
145                 150                 155                 160

His Pro Val Ile Gln Asn Phe Ser Tyr Glu Thr Phe Gln Gln Lys Met
                165                 170                 175

Leu Arg Phe Leu Glu Ser His Leu Asp Asp Ala Glu Pro Tyr Leu Leu
            180                 185                 190

Thr Met Ala Lys Lys Ala Leu Lys
        195                 200
```

(2) INFORMATION FOR SEQ ID NO:46:

(i) SEQUENCE CHARACTERISTICS:
        (A) LENGTH: 600 base pairs
        (B) TYPE: nucleic acid
        (C) STRANDEDNESS: double
        (D) TOPOLOGY: linear (ii) MOLECULE TYPE: cDNA
        (A) DESCRIPTION: TRF2

(iii) HYPOTHETICAL: NO (vi) ORIGINAL SOURCE:
        (A) ORGANISM: mouse (xi) SEQUENCE DESCRIPTION: SEQ ID NO:46:

```
GCTCGCCTGG AGGAGGCGGT CAACCGCTGG GTGCTCAAGT TCTATTTCCA CGAGGCGCTG      60

CGGGCCTTTC GGAGTAGCCG GTACCGGGAC TTCAGGCAGA TCCGGACAT CATGCAGGCG      120

TTGCTTGTCA GGCCCTTGGG GAAGGAGCAT ACGGTGTCCC GGTTGCTGCG GGTTATGCAG     180

TGTCTGTCGC GCATTGAAGA AGGAGAAAAT TTAGACTGTT CCTTTGATAT GGAGGCTGAG     240

CTCACACCCT TGGAATCAGC TATCAATGTG CTGGAGATGA TTAAAACAGA GTTCACACTG     300

ACAGACTCTA TGGTTGAATC CAGCAGAAAA CTGGTCAAGG AGGCTGCTGT CATTATTTGT     360

ATCAAAAACA AGAATTTGA AAAGGCTTCA AGATTTTGA AAAAATACAT GTCTAAGGAC       420

CCCACAACTC AGAAGCTGAG AACTGATCTC CTGAACATTA TCCGGGAAAA GAACTTGGCC     480

CACCCTGTTA TCCAGAACTT TTCCTATGAG GTCTTCCAGC AGAAGATGCT GCGTTTCCTA     540

GAGAGCCACC TGGATGACAC GGAGCCCTAC CTCCTCACGA TGGCTAAAAA AGCTTTGAAA     600
```

(2) INFORMATION FOR SEQ ID NO:47:

(i) SEQUENCE CHARACTERISTICS:
        (A) LENGTH: 200 amino acids
        (B) TYPE: amino acid
        (C) STRANDEDNESS: single
        (D) TOPOLOGY: linear (ii) MOLECULE TYPE: protein
        (A) DESCRIPTION: TRF2

(iii) HYPOTHETICAL: NO (vi) ORIGINAL SOURCE:
        (A) ORGANISM: mouse (xi) SEQUENCE DESCRIPTION: SEQ ID NO:47:

```
Ala Arg Leu Glu Glu Ala Val Asn Arg Trp Val Leu Lys Phe Tyr Phe
1               5                   10                  15

His Glu Ala Leu Arg Ala Phe Arg Ser Ser Arg Tyr Arg Asp Phe Arg
                20                  25                  30

Gln Ile Arg Asp Ile Met Gln Ala Leu Leu Val Arg Pro Leu Gly Lys
            35                  40                  45

Glu His Thr Val Ser Arg Leu Leu Arg Val Met Gln Cys Leu Ser Arg
        50                  55                  60

Ile Glu Glu Gly Glu Asn Leu Asp Cys Ser Phe Asp Met Glu Ala Glu
65                  70                  75                  80

Leu Thr Pro Leu Glu Ser Ala Ile Asn Val Leu Glu Met Ile Lys Thr
                85                  90                  95

Glu Phe Thr Leu Thr Asp Ser Met Val Glu Ser Ser Arg Lys Leu Val
            100                 105                 110
```

```
Lys Glu Ala Ala Val Ile Ile Cys Ile Lys Asn Lys Glu Phe Glu Lys
        115                 120                 125

Ala Ser Lys Ile Leu Lys Lys Tyr Met Ser Lys Asp Pro Thr Thr Gln
        130                 135                 140

Lys Leu Arg Thr Asp Leu Leu Asn Ile Ile Arg Glu Lys Asn Leu Ala
145                 150                 155                 160

His Pro Val Ile Gln Asn Phe Ser Tyr Glu Val Phe Gln Gln Lys Met
                165                 170                 175

Leu Arg Phe Leu Glu Ser His Leu Asp Asp Thr Glu Pro Tyr Leu Leu
            180                 185                 190

Thr Met Ala Lys Lys Ala Leu Lys
        195                 200
```

(2) INFORMATION FOR SEQ ID NO:48:

(i) SEQUENCE CHARACTERISTICS:
        (A) LENGTH: 606 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (vi) ORIGINAL SOURCE:
        (A) ORGANISM: chicken (xi) SEQUENCE DESCRIPTION: SEQ ID NO:48:

```
GCGTTGGCAG AAGCTGTGGC CGCGGACTGG GTGCTGGAAT TCAGCTGCTG CTGTCTGTGC    60

CGGTATTTCG TGGAGGAGTG TGAGGCCGAG TTCAGGCGGT GGAGGGACGT GGCGCACGCT   120

GTTTCTAATG GCTTCTCCAA AGTAACAACG CATCAGAAAA AAATGGTGTA CCTCTGTCAG   180

CTTTTGATAA GAATTGCAGA AGGAAAAAGA CTTGAATGCC ACTTTGAAAA CAATACAACA   240

ATTTCGCCTT TGGAGTCTGC TCTGTCTTTT TGGACTTTAC TTGAAAGGGA AGAAAGTAAA   300

CTAAATACAC TTCATGAAGA AATCCGTCGC TTGATTCAAA TTCAGGTTGT AGCAGTCTAT   360

ATGGAAAAAG GATATTATAA GGAGGCTGCT GAAGTTCTTG AAAGGCTATT CACAGACTCA   420

GAATCACATA AGCCTTTAAG GATGAAGCTG GCAGCCATAG TCAAAAGCAA GGATCCATAT   480

GTTCCCCTTC TCCAGAGCTT CAGTTACAGT CTTTTGTTAA GTAAAGTCAA GTCTTACGTC   540

AAACTTTTCC TGAAAGAAAA CAGAACCAAC TTCTTACTAC AGGCAGCTAC AAAACAAGTG   600

GAGTCT                                                              606
```

(2) INFORMATION FOR SEQ ID NO:49:

(i) SEQUENCE CHARACTERISTICS:
        (A) LENGTH: 202 amino acids
        (B) TYPE: amino acid
        (C) STRANDEDNESS: single
        (D) TOPOLOGY: linear (ii) MOLECULE TYPE: protein (iii) HYPOTHETICAL: NO (vi) ORIGINAL SOURCE:
        (A) ORGANISM: chicken (xi) SEQUENCE DESCRIPTION: SEQ ID NO:49:

```
Ala Leu Ala Glu Ala Val Ala Ala Asp Trp Val Leu Glu Phe Ser Cys
1               5                   10                  15
```

```
Cys Cys Leu Cys Arg Tyr Phe Val Glu Glu Cys Glu Ala Glu Phe Arg
            20                  25                  30

Arg Trp Arg Asp Val Ala His Ala Val Ser Asn Gly Phe Ser Lys Val
        35                  40                  45

Thr Thr His Gln Lys Lys Met Val Tyr Leu Cys Gln Leu Leu Ile Arg
    50                  55                  60

Ile Ala Glu Gly Lys Arg Leu Glu Cys His Phe Glu Asn Asn Thr Thr
65                  70                  75                  80

Ile Ser Pro Leu Glu Ser Ala Leu Ser Phe Trp Thr Leu Leu Glu Arg
                85                  90                  95

Glu Glu Ser Lys Leu Asn Thr Leu His Glu Glu Ile Arg Arg Leu Ile
            100                 105                 110

Gln Ile Gln Val Val Ala Val Tyr Met Glu Lys Gly Tyr Tyr Lys Glu
            115                 120                 125

Ala Ala Glu Val Leu Glu Arg Leu Phe Thr Asp Ser Glu Ser His Lys
        130                 135                 140

Pro Leu Arg Met Lys Leu Ala Ala Ile Val Lys Ser Lys Asp Pro Tyr
145                 150                 155                 160

Val Pro Leu Leu Gln Ser Phe Ser Tyr Ser Leu Leu Ser Lys Val
                165                 170                 175

Lys Ser Tyr Val Lys Leu Phe Leu Lys Glu Asn Arg Thr Asn Phe Leu
            180                 185                 190

Leu Gln Ala Ala Thr Lys Gln Val Glu Ser
            195                 200
```

(2) INFORMATION FOR SEQ ID NO:50:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:50:

TTGAATTCGA GGCACGGCTG GAAGAG                                        26

(2) INFORMATION FOR SEQ ID NO:51:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:51:

CGGGATCCTG TTTCAGTTCA TGCCAA                                        26

(2) INFORMATION FOR SEQ ID NO:52:

(i) SEQUENCE CHARACTERISTICS:
        (A) LENGTH: 31 base pairs
        (B) TYPE: nucleic acid -continued

```
        (C) STRANDEDNESS: single
        (D) TOPOLOGY: linear (ii) MOLECULE TYPE: other nucleic acid
        (A) DESCRIPTION: /desc = "Primer"

(iii) HYPOTHETICAL: NO (xi) SEQUENCE DESCRIPTION: SEQ ID NO:52:

CGGGATCCTC ATTCTACAGT CCACTTCTGC T                                       31
```

TELOMERE REPEAT BINDING FACTORS AND DIAGNOSTIC AND THERAPEUTIC USE THEREOF

CROSS-REFERENCE TO RELATED APPLICATIONS

The present Application is a Continuation-In-Part of U.S. Ser. No. 08/938,052 filed Sep. 26, 1997, now abandoned, which in turn is a Continuation-In-Part of U.S. Ser. No. 08/519,103 filed Aug. 25, 1995, now U.S. Pat. No. 5,733,730, Issued Mar. 31, 1998, the disclosures of which are hereby incorporated by reference in their entireties. Applicants claim the benefits of these prior filings under 35 U.S.C. §120.

GOVERNMENTAL SUPPORT

The research leading to the present invention was supported, in part, by a grant from the National Institutes of Health, No. GM49046 and MSTP No. GM07739. Accordingly, the United States Government may have certain rights in the present invention.

TECHNICAL FIELD OF THE INVENTION

The present invention relates generally to telomeric binding proteins, in particular to telomeric repeat binding factors (TRFs), to the nucleotiae and ammo acid sequences encoding the TRFs, and to diagnostic and therapeutic methods of use thereof. TRFs have particular uses in the treatment of cancer and aging.

BACKGROUND OF THE INVENTION

Eucaryotic chromosomes end in specialized structures, called telomeres [Muller, *The Collecting Net-Woods Hole*, 13:181–195 (1939] that are thought to fulfill at least three functions. First, telomeres protect natural double-stranded DNA ends from degradation, fusion, and recombination with chromosome-internal DNA [McClintock, *Genetics*, 26:234–282 (1941)]. Second, cytogenetic observations indicate that telomeres are located at the nuclear periphery, suggesting a role for chromosome ends in the architecture of the nucleus [Agard et al., *Nature*, 302:676–681 (1983); Rabl, *Morphol. J.*, 10:214–330 (1885)]. Third, telomeres must provide a solution to the end-replication problem [Watson, *Nature*, 239:197–201 (1972)]: because all known polymerases require a primer and synthesize DNA from 5' to 3', the 3' ends of linear DNA pose a problem to the replication machinery.

The single common structural feature of most eucaryotic telomeres is the presence of a tandem array of G-rich repeats which, according to genetic studies in *Saccharomyces cerevisiae*, are necessary and sufficient for telomere function [Lunablad et al., *Cell*, 83:633–643 (1989); Szostak et al., *Cell*, 36:459–568 (1982)]. Although all telomeres of one genome are composed of the same repeats, the terminal sequences in different species vary. For instance, Oxytricha chromosomes terminate in TTTTGGGG repeats [Klobutcher et al., *Proc. Natl. Acad. Sci. USA*, 78:3015–3019 (1981)], Tetrahymena utilizes an array of $(TTGGGG)_n$ [Blackburn et al., *J. Mol. Biol.*, 120:33–53 (1978)], plant chromosomes carry the sequence $(TTTAGGG)_n$ (Richards et al., *Cell*, 53:127–136 (1988)], and trypanosomas and mammals have TTAGGG repeats at their chromosome ends [Blackburn et al., *Cell*, 36:447–458 (1984); Brown, *Nature*, 338:774–776 (1986); Cross et al., *Nature*, 338:771–774 (1989); Moyzis et al., *Proc. Natl. Acad. Sci. USA*, 85:6622–6626 (1988); Van der Ploeg et al., *Cell* 36:459–468 (1984)]. The organization of the telomeric repeats is such that the G-rich strand extends to the 3' end of the chromosome. At this position, telomerase, an RNA-dependent DNA polymerase, first demonstrated in *Tetrahymena thermophila* and other ciliates, can elongate telomeres, probably by using an internal RNA component as template for the addition of the appropriate G-rich sequence [Greider and Blackburn, *Cell*, 43:405–413 (1985)]. This activity is thought to complement the inability of polymerases to replicate chromosome ends, but other mechanisms of telomere maintenance may operate as well [Pluta et al., *Nature*, 337:429–433 (1989)]. Recently, it has been reported that the addition of telomerase into a cultured human cell leads to an increase of the proliferative life-span of that cell [Bodner et al., *Science*, 279:349–352 (1998)].

Proximal to the essential telomeric repeats, some chromosome ends harbor additional common elements called sub-telomeric repeats or telomere-associated sequences [Chan et al., *Cell*, 33:563–573 (1983); Corcoran et al., *Cell*, 53:807–813 (1988); de Lange et al., *Nucl. Acids. Res.*, 11:8149–8165 (1983); Van der Ploeg et al. (1984); Dunn et al., *Cell*, 39:191–201 (1984)]. Unlike telomeric repeats, these sequences are not conserved and their function remains unclear [Murray et al., *Mol. Cell. Biol.*, 6:3166–3172 (1986)].

Chromosome ends of unicellular organisms often show structural instability. Frequent rearrangements of subtelomeric sequences occur in trypanosomas [Borst, *Annu. Rev. Biochem.*, 55:701–732 (1986), de Lange et al. (1983)], *S. cerevisiae* [Carlson et al., *Mol. Cell. Biol.*, 3:351–359 (1983); Horowitz et al., *Mol. Cell. Biol.*, 4:2509–2517 (1984)], and plasmodia [Corcoran et al., (1988)], and changes in the telomeric repeat region can be observed in protozoa [Bernards et al., *Nature*, 303:592–597 (1983); Pays, *Nucl. Acids. Res.*, 11:8137–8147 (1983); Van der Ploeg (1984)], ciliates [Larson et al., *Cell*, 50:477–483 (1987)], and fungi [Carson et al., *Cell*, 42:249–257 (1985); Lundblad et al., (1989); Lustig et al., *Proc. Natl. Acad. Sci. USA*, 83:1398–1402 (1986)]. As much as 3.5 kilobase pairs (kb) was seen to be added to telomeres of *Trypanosoma brucei* in a process that appears gradual and continuous, and was calculated to result from the addition of 6 to 10 base pairs (bp) per end per cell division [Bernards et al., (1983); Pays et al., (1983); Van der Ploeg, (1984)]. A similar gradual telomere elongation, compatible with the addition of telomeric repeats by telomerase, occurs in continuously growing *T. thermophila* [Larson, (1987)] and a cell cycle mutant (cdc17) of *S. cerevisiae* [Carson et al., (1985)]. In wild-type *S. cerevisiae* [Shampay et al., *Proc. Natl. Acad. Sci. USA*, 85:534–538 (1988)], however, and in *T. thermophila* grown in batch cultures [Larson et al., (1998)], the tandem array of telomeric repeats is maintained at constant length. At least four genes (CDC17, EST1, TEL1, and TEL2 [Carson et al., (1985); Lundblad et al., (1989); Lustig et al., (1986)] govern the length and stability of yeast telomeres; their mode of action is not understood.

Much less is known about the structure and behavior of chromosome ends of multicellular organisms. Mammalian telomeres have become amenable to molecular dissection with the demonstration that telomeric repeats of plants and *T. thermophila* species cross-hybridize to vertebrate chromosome ends [Allshire et al., *Nature*, 332:656–659 (1988); Richards et al., (1988)]. It has also been shown that human DNA contains tandem arrays of TTAGGG repeats, probably at the chromosome ends, providing further evidence for the evolutionary conservation of telomeres and a tool for the isolation of telomeric DNA [Moyzis et al., (1988)]. Two strategies to obtain human chromosome ends have proven successful: an indirect isolation protocol that relies on human telomeres to be functional in *S. cerevisiae* [Brown et al., (1989); Cross et al., (1989)] and direct cloning in *E. coli*.

de Lange et al. [*Mol. Cell. Biol.*, 10:518–527 (1990)] characterized the structure and variability of human autosomal chromosome ends. The chromosome ends they analyzed shared a sub-telomeric repeat of at least 4 kb that is not conserved in rodent genomes. These chromosome ends were characterized by a long stretch of DNA, of up to 14 kb, that lacks restriction enzyme cutting sites and may be entirely composed of TTAGGG repeats. From this region sequences are lost during development, leading to shortened, heterogeneously sized telomeres in somatic tissues, primary tumors, and most cell lines.

de Lange [*EMBO J.*, 11:717–724 (1992)] reported that human telomeres are tightly associated with the nuclear matrix. Telomeres were demonstrated to be anchored via their TTAGGG repeats. Moreover, TTAGGG repeats at internal sites within the chromosome do not behave as matrix-attached loci, suggesting that the telomeric position of the repeats is required for their interaction with the nuclear matrix. This evidence is consistent with the role of telomeres in a nucleoprotein complex.

TRF activity was first identified in 1992 by Zhong et al. [*Mol. Cell. Biol*, 12:4834–4943 (1992)] as a DNA-binding factor specific for TTAGGG repeat arrays. TRF was found to be present in nuclear extracts of human, mouse and monkey cells. The optimal site for TRF binding was found to contain at least six contiguous TTAGGG repeats. However, the protein isolated by Zhong et al. was not sufficiently purified from other DNA-binding proteins such that its amino acid sequence could be determined.

Saltman et al. [*Chromosoma*, 102:121–128 (1993)] characterized the molecular structure of telomeres of two human tumor cell lines with frequent end-to-end associations of metaphase chromosomes. Such end-to-end associations have been observed in a variety of human tumors, aging cells and several chromosome instability syndromes. The telomeres of such end-associated chromosomes were shown by Saltman et al. to be severely reduced compared to other human cells with functional telomeres. However, other cell lines with severely shortened telomeres were not detectably compromised in their function. Thus, the investigators suggested that telomeric length was not the only determinant of the fusigenic behavior of human telomeres in tumor cells.

A *Xenopus laevis* protein factor that specifically recognizes vertebrate telomeric repeats at DNA ends, termed Xenopus telomere end factor (XTEF) was identified by Cardenas et al. in 1993 [*Genes and Devel.*, 7:883–894 (1993)]. The DNA-binding properties of XTEF resembled the characteristics of a class of terminus-specific telomere proteins identified in hypotrichous ciliates.

There has been speculation on the role of an enzyme termed telomerase in human cancer, in particular in ovarian carcinoma [de Lange, *Proc. Natl. Acad. Sci. USA*, 91:2882–2885 (1994)]. Telomerases use the 3' end of DNA as a primer and employ an RNA template for the synthesis of G-rich telomeric repeats. Telomerase activation appears to be an obligatory step in the immortalization of human cells.

Hanish et al. [*Proc. Natl. Acad. Sci. USA*, 91:8861–8865 (1994)] examined the requirements for the formation of human telomeres from TTAGGG seeds, and found that telomere formation was not correlated with the ability of human telomerase to elongate telomeric sequences in vitro, and did not appear to be a result of homologous recombination. Rather, the investigators reported that the sequence dependence of telomere formation matched the in vitro binding requirements for TRF1.

Although the activity of TRF1 had been identified and isolated to some extent, the purification of TRF was fraught with difficulty, both in isolating the protein away from other DNA binding proteins, and in obtaining active protein from the isolate.

Therefore, there is a need to isolate and characterize vertebrate TRF1. In addition, there is a need to identify other vertebrate telomere repeat binding factors which must also serve as structural and/or functional proteins in the maintenance of normal telomere physiological processes. Further, there is a need to isolate and characterize such TRFs (including TRF2) and to distinguish their characteristics from TRF1, as well as ascertain the role such TRFs play in telomere maintenance and elongation.

SUMMARY OF THE INVENTION

The present invention provides vertebrate telomeric binding factors (TRFs) that bind to the TTAGGG repeat sequences of telomeres. Such TRFs comprise two key domains: a dimerization domain, and a Myb domain. In addition, at least some TRFs, e.g. mammalian TRF1 and TRF2 contain a third domain, a polar N-terminal domain. In specific examples, the TRF nucleotide sequence is isolated from human, murine, or avian sources. The present invention includes these nucleic acids, the TRFs they encode, the individual domains of the encoded TRFs, and the nucleic acids that encode these individual domains.

In one particular embodiment of the present invention the TRF has the following characteristics:

a) it binds to telomere repeat sequences, in particular, TTAGGG repeats;

b) the DNA binding activity in a purified form requires the presence of another factor such as casein; and c) it exhibits substantial sequence homology to Myb type DNA binding domains.

The present invention includes a nucleic acid or a degenerate variant thereof, which encodes a TRF of the present invention; preferably a recombinant DNA molecule or cloned gene. For example a recombinant DNA molecule or cloned gene, encodes a TRF such a TRF1 which has a nucleotide sequence of (or complementary to) SEQ ID NO:11 (shown in FIGS. 2A–2B), or SEQ ID NO:22. These nucleotide sequences encode a TRF having an amino acid sequence of SEQ ID NO:12 or 23 respectively which are also part of the present invention. A nucleotide sequence of a TRF1 having a nucleotide sequence of SEQ ID NO:24 is also part of the present invention.

The present invention also provides an isolated nucleic acid encoding a vertebrate telomere repeat binding factor (TRF) which is a TRF2 having an amino acid sequence substantially homologous to that of SEQ ID NO:27, and comprising the following characteristics: a basic N-terminal domain; a dimerization domain; and a Myb domain. In one such embodiment when the basic N-terminal domain is removed the TRF detectably binds to the telomere repeat sequence $(TTAGGG)_{12}$. Such binding is preferably detected in an in vitro assay.

In a preferred embodiment of this type, the isolated nucleic acid encodes a TRF that is a mammalian protein. More preferably the isolated nucleic acid encodes a human TRF having the amino acid sequence of SEQ ID NO:27, or SEQ ID NO:27 with a conservative amino acid substitution. In a particular embodiment the nucleic acid encodes a human TRF having the amino acid sequence of SEQ ID NO:27. In a preferred embodiment of this type the isolated nucleic acid comprises the coding sequence of SEQ ID NO:26.

In another embodiment the isolated nucleic acid encodes a murine TRF having the amino acid sequence of SEQ ID NO:29, or SEQ ID NO:29 with a conservative amino acid substitution. In a particular embodiment the nucleic acid encodes a murine TRF having the amino acid sequence of SEQ ID NO:29. In a preferred embodiment of this type the isolated nucleic acid comprises the coding sequence of SEQ ID NO:28.

Another aspect of the invention includes a nucleic acid encoding an avian TRF1 having the nucleotide sequence of SEQ ID NO:24. All of the isolated nucleic acids of the present invention can further comprise a heterologous nucleotide sequence. Such heterologous nucleotide sequences can encode, for example, a fusion peptide (e.g., a FLAG-tag as in Example 7 below) or a chimeric protein partner such as a fusion protein. In addition any isolated nucleic acid of the present invention e.g., the corresponding recombinant DNA molecule or cloned gene can be operatively linked to an expression control sequence which may be introduced into an appropriate host. The present invention accordingly extends to unicellular hosts transformed with the cloned gene or recombinant DNA molecule comprising a DNA sequence encoding a TRF, or a structural/functional domain of a TRF of the present invention.

In one such example, the present invention provides the isolated nucleic acid encoding a vertebrate TRF having an amino acid sequence of SEQ ID NO:27 operatively linked to an expression control sequence. The present invention also provides a unicellular host transformed or transfected with the nucleic acid. In addition the present invention provides a method of expressing the TRF encoded by the nucleic acid which comprises culturing the unicellular host in an appropriate cell culture medium under conditions that provide for expression of the protein by the cell. This method can further comprise the step of purifying the TRF. The purified form of the TRF obtained by such methodology is also part of the present invention. This methodology is intended to be general and is suitable for the expression and isolation of all of the nucleic acids of the present invention.

According to other preferred features of certain preferred embodiments of the present invention, a recombinant expression system is provided to produce biologically active vertebrate TRFs, including human TRFs as well as TRF structural/functional domains, TRF chimeric proteins and the like.

The present invention also includes nucleic acids that encode the dimerization domain of a TRF and/or the basic or acidic N-terminal domain of a TRF. In one such embodiment an isolated nucleic acid comprises a nucleotide sequence encoding a basic N-terminal domain of a TRF that has the amino acid sequence of SEQ ID NO:37, or SEQ ID NO:37 with a conservative amino acid substitution. In a particular embodiment the nucleic acid encodes a basic N-terminal domain that has the amino acid sequence of SEQ ID NO:37. In a preferred embodiment of this type the isolated nucleic acid comprises the coding sequence of SEQ ID NO:36. In another such embodiment an isolated nucleic acid comprises a nucleotide sequence encoding a basic N-terminal domain of a TRF that has the amino acid sequence of SEQ ID NO:39, or SEQ ID NO:39 with a conservative amino acid substitution. In a particular embodiment the nucleic acid encodes a basic N-terminal domain that has the amino acid sequence of SEQ ID NO:39. In a preferred embodiment of this type the isolated nucleic acid comprises the coding sequence of SEQ ID NO:38.

In another embodiment an isolated nucleic acid comprises a nucleotide sequence encoding an acidic N-terminal domain of a TRF that has the amino acid sequence of SEQ ID NO:33, or SEQ ID NO:33 with a conservative amino acid substitution. In a particular embodiment the nucleic acid encodes an acidic N-terminal domain that has the amino acid sequence of SEQ ID NO:33. In a preferred embodiment of this type the isolated nucleic acid comprises the coding sequence of SEQ ID NO:32. In another such embodiment an isolated nucleic acid comprises a nucleotide sequence encoding an acidic N-terminal domain of a TRF that has the amino acid sequence of SEQ ID NO:35, or SEQ ID NO:35 with a conservative amino acid substitution. In a particular embodiment the nucleic acid encodes an acidic N-terminal domain that has the amino acid sequence of SEQ ID NO:35. In a preferred embodiment of this type the isolated nucleic acid comprises the coding sequence of SEQ ID NO:34.

In still another embodiment an isolated nucleic acid comprises a nucleotide sequence encoding a dimerization domain of a TRF that has the amino acid sequence of SEQ ID NO:45, or SEQ ID NO:45 with a conservative amino acid substitution. In a particular embodiment the nucleic acid comprises a nucleotide sequence encoding a dimerization domain that has the amino acid sequence of SEQ ID NO:45. In a preferred embodiment of this type the isolated nucleic acid comprises the coding sequence of SEQ ID NO:44.

In a related embodiment an isolated nucleic acid comprises a nucleotide sequence encoding a dimerization domain of a TRF that has the amino acid sequence of SEQ ID NO:47, or SEQ ID NO:47 with a conservative amino acid substitution. In a particular embodiment the nucleic acid comprises a nucleotide sequence encoding a dimerization domain that has the amino acid sequence of SEQ ID NO:47. In a preferred embodiment of this type the isolated nucleic acid comprises the coding sequence of SEQ ID NO:46.

In another embodiment an isolated nucleic acid comprises a nucleotide sequence encoding a dimerization domain of a TRF that has the amino acid sequence of SEQ ID NO:43, or SEQ ID NO:43 with a conservative amino acid substitution. In a particular embodiment the nucleic acid comprises a nucleotide sequence encoding a dimerization domain that has the amino acid sequence of SEQ ID NO:43. In a preferred embodiment of this type the isolated nucleic acid comprises the coding sequence of SEQ ID NO:42.

In yet another embodiment an isolated nucleic acid comprises a nucleotide sequence encoding a dimerization domain of a TRF that has the amino acid sequence of SEQ ID NO:49, or SEQ ID NO:49 with a conservative amino acid substitution. In a particular embodiment the nucleic acid comprises a nucleotide sequence encoding a dimerization domain that has the amino acid sequence of SEQ ID NO:49. In a preferred embodiment of this type the isolated nucleic acid comprises the coding sequence of SEQ ID NO:48.

In still another embodiment an isolated nucleic acid comprises a nucleotide sequence encoding a dimerization domain of a TRF that has the amino acid sequence of SEQ ID NO:41, or SEQ ID NO:41 with a conservative amino acid substitution. In a particular embodiment the nucleic acid comprises a nucleotide sequence encoding a dimerization domain that has the amino acid sequence of SEQ ID NO:41. In a preferred embodiment of this type the isolated nucleic acid comprises the coding sequence of SEQ ID NO:40.

The present invention includes an isolated nucleic acid comprising a nucleotide sequence encoding a truncated vertebrate TRF that has the amino acid sequence of SEQ ID NO:31 or SEQ ID NO:31 with a conservative amino acid substitution. In a particular embodiment the isolated nucleic acid comprises a nucleotide sequence encoding a truncated vertebrate TRF that has the amino acid sequence of SEQ ID NO:31. In a preferred embodiment of this type the isolated nucleic acid has the nucleotide sequence of SEQ ID NO:30.

The present invention also provides all of the peptides or proteins that are encoded by all of the nucleic acids of the present invention including isolated TRFs, proteolytic fragments of TRFs, truncated proteins, and peptides or proteins comprising a particular domain of a TRF such as the dimerization domain, the Myb domain or the basic or acidic N-terminal domain of the TRF. In addition, all of these proteins and peptides can be combined into corresponding chimeric proteins or peptides such as fusion proteins or fusion peptides. Such chimeric proteins and peptides are also part of the present invention including for example, a chimeric protein having an N-terminal domain and a dimerization domain of a TRF2 and a Myb domain of TRF1.

In one such embodiment the isolated vertebrate telomere repeat binding factor (TRF) has an amino acid sequence substantially homologous to that of SEQ ID NO:27, and comprises the following characteristics: a basic N-terminal domain, a dimerization domain, and a Myb domain. In a preferred embodiment when the basic N-terminal domain is removed the TRF detectably binds to the telomere repeat sequence $(TTAGGG)_{12}$. Such binding is preferably detected in an in vitro assay. Preferably the isolated TRF is a is a mammalian protein.

In one embodiment the isolated TRF is a human protein having the amino acid sequence of SEQ ID NO:27, or SEQ ID NO:27 with a conservative amino acid substitution. In a particular embodiment the isolated TRF has the amino acid sequence of SEQ ID NO:27. In another embodiment the isolated TRF is a murine protein having the amino acid sequence of SEQ ID NO:29, or SEQ ID NO:29 with a conservative amino acid substitution. In a particular embodiment the isolated TRF has the amino acid sequence of SEQ ID NO:29.

The present invention further provides an isolated protein comprising the basic N-terminal domain of a TRF that has the amino acid sequence of SEQ ID NO:37, or SEQ ID NO:37 with a conservative amino acid substitution. In a particular embodiment the isolated the basic N-terminal domain has the amino acid sequence of SEQ ID NO:37. Another embodiment comprises the basic N-terminal domain of a TRF that has the amino acid sequence of SEQ ID NO:39, or SEQ ID NO:39 with a conservative amino acid substitution. In a particular embodiment the isolated the basic N-terminal domain has the amino acid sequence of SEQ ID NO:39.

An isolated protein comprising a dimerization domain of a TRF having the amino acid sequence of SEQ ID NO:45, or SEQ ID NO:45 with a conservative amino acid substitution is also included in the present invention. In a particular embodiment the isolated the dimerization domain has the amino acid sequence of SEQ ID NO:45. A related embodiment contains an isolated protein comprising a dimerization domain of a TRF having the amino acid sequence of SEQ ID NO:47, or SEQ ID NO:47 with a conservative amino acid substitution. In a particular embodiment the isolated the dimerization domain has the amino acid sequence of SEQ ID NO:47.

The present invention also includes an isolated protein comprising a dimerization domain of a TRF having the amino acid sequence of SEQ ID NO:41, or SEQ ID NO:41 with a conservative amino acid substitution. In a particular embodiment the isolated the dimerization domain has the amino acid sequence of SEQ ID NO:41. A related embodiment contains an isolated protein comprising a dimerization domain of a TRF having the amino acid sequence of SEQ ID NO:43, or SEQ ID NO:43 with a conservative amino acid substitution. In a particular embodiment the isolated the dimerization domain has the amino acid sequence of SEQ ID NO:43. In yet another embodiment an isolated protein comprises a dimerization domain of a TRF that has the amino acid sequence of SEQ ID NO:49, or SEQ ID NO:49 with a conservative amino acid substitution. In a particular embodiment of this type, the dimerization domain has the amino acid sequence of SEQ ID NO:49.

The present invention further provides an isolated avian TRF encoded by SEQ ID NO:24.

The present invention also provides an isolated protein that is a truncated TRF having the amino acid sequence of SEQ ID NO:31 or SEQ ID NO:31 with a conservative amino acid substitution. In a particular embodiment the isolated the truncated TRF has the amino acid sequence of SEQ ID NO:31.

The present invention also includes antibodies to all of the TRFs and TRF domains of the present invention. One such embodiment is an antibody that recognizes a basic N-terminal domain of a TRF that has the amino acid sequence of SEQ ID NO:37. In another such embodiment the antibody recognizes a basic N-terminal domain of a TRF that has the amino acid sequence of SEQ ID NO:39.

Such antibodies can be polyclonal, monoclonal, and/or chimeric antibodies. The present invention also includes immortal cell lines that produce the monoclonal antibodies of the present invention.

In a related aspect of the present invention, a novel method for purifying telomeric binding proteins is provided, which comprises the steps of:

a) isolating nuclei from tissue culture cells;

b) preparing nuclear extracts of the nuclei;

c) contacting the nuclear extracts with an affinity chromatography column comprising a bound DNA fragment, wherein the DNA fragment comprises TTAGGG repeat sequences; and d) eluting telomeric binding proteins from the column.

In a particular embodiment, casein is added to the eluted telomeric binding proteins to obtain active DNA-binding proteins.

In another aspect of the present invention, the TRFs of the present invention or antagonists or agonists thereof may be used to counteract the shortening of telomere length which occurs during aging, and to counteract the abnormal telomere physiology present in cancerous cells. Accordingly, methods of providing a TRF and/or its agonists or antagonists are contemplated.

Still a further aspect of the present invention extends to antibodies and oligonucleotide probes to the TRFs of the present invention, which may be used for both diagnostic and therapeutic approaches.

The DNA sequences of the TRFs of the present invention or portions thereof, may be prepared as probes to screen for complementary sequences and genomic clones in the same or alternate species. The present invention extends to probes so prepared that may be provided for screening cDNA and genomic libraries for the TRF. For example, the probes may be prepared with a variety of known vectors, such as the phage λ vector. The present invention also includes the preparation of plasmids including such vectors, and the use of the DNA sequences to construct vectors expressing antisense RNA or ribozymes which would attack the mRNAs of any or all of the DNA sequences in the present invention. Correspondingly, the preparation of antisense RNA and ribozymes are included herein.

The present invention also includes TRF proteins having the activities noted herein, and that have the amino acid sequences included in the present invention.

The present invention provides specific factors i.e., TRFs, which bind to TTAGGG repeat sequences as described earlier. Accordingly, the exact structure of each TRF will understandably vary so as to achieve this DNA binding and activity specificity. It is this specificity and the direct involvement of the TRF in the chain of events leading to telomere length regulation, that offers the promise of a broad spectrum of diagnostic and therapeutic utilities.

The present invention naturally contemplates several means for preparation of a TRF, including as illustrated herein known recombinant techniques, and the invention is accordingly intended to cover such synthetic preparations within its scope. The isolation of the cDNAs that encode a TRF amino acid sequence disclosed herein (e.g., using a nucleic acid that hybridizes with the cDNA encoding a TRF to act as a probe/binding partner to detect and/or isolate a nucleic acid encoding a related TRF), facilitates the reproduction of the TRF by such recombinant techniques, and accordingly, the invention extends to expression vectors prepared from the disclosed DNA sequences for expression in host systems by recombinant DNA techniques, and to the resulting transformed hosts.

The invention includes an assay system for screening of potential drugs effective to modulate TRF activity of target mammalian cells by interrupting or potentiating the activity of the TRF. In one instance, the test drug could be administered to a cellular sample containing the TRF along with telomeric sequences, to determine its effect upon the binding activity of the TRF to the DNA, or to the test drug, by comparison with a control. In still another assay, the purified TRFs or a particular structural/functional domain are used as targets for testing the binding characteristics of potential drugs. For example, the basic N-terminal domain of TRF2 and acidic N-terminal domain of TRF1 can be employed to screen potential drugs for binding specificity for the two corresponding TRFs. In this way a drug can be readily identified which is likely to interfere with TRF1 without interfering with TRF2.

The assay system could more importantly be adapted to identify drugs or other entities that are capable of binding to a TRF and/or other telomeric binding factors or proteins in the nucleus, thereby inhibiting or potentiating the activity of the TRF. Such assays would be useful in the development of drugs that would be specific against particular cellular activity, or that would potentiate such activity, in time or in level of activity. For example, such drugs might be used to inhibit the proliferation of cells in cancerous states, or to treat cells which are aging, or to treat other pathologies associated with variations in telomere length.

In yet a further embodiment, the invention contemplates antagonists of the activity of a TRF, in particular, an agent or molecule that inhibits the role of TRFs in telomere function. In a specific embodiment, the antagonist can be a peptide having the sequence of a portion of a DNA binding domain of a TRF, such as that illustrated by SEQ ID NO:13.

The diagnostic utility of the present invention extends to the use of the present TRF in assays to screen for cancer and other inherited diseases associated with telomere length.

The present invention likewise extends to the development of antibodies against the TRFs or to the specific structural/functional domains of the TRFs of the present invention, including naturally raised and recombinantly prepared antibodies. For example an antibody raised against the basic N-terminal domain of a TRF can be used to distinguish a TRF2 from a TRF1. In addition, the antibodies could be used to screen expression libraries to obtain the gene or genes that encode the TRFs. Such antibodies could include both polyclonal and monoclonal antibodies prepared by known genetic techniques, as well as bi-specific (chimeric) antibodies, and antibodies including other functionalities suiting them for additional diagnostic use conjunctive with their capability of modulating telomere length.

Thus, the TRFs, their analogs and/or agonists, and any antagonists or antibodies that may be raised thereto, are capable of use in connection with various diagnostic techniques, including immunoassays, such as a radioimmunoassay, using for example, an antibody to the TRF that has been labelled by either radioactive addition, reduction with sodium borohydride, or radio iodination.

In an immunoassay, a control quantity of the antagonists or antibodies thereto, or the like may be prepared and labelled with an enzyme, a specific binding partner and/or a radioactive element, and may then be introduced into a cellular sample. After the labelled material or its binding partner(s) has had an opportunity to react with sites within the sample, the resulting mass may be examined by known techniques, which may vary with the nature of the label attached.

In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the instance where the label is an enzyme, detection may be accomplished by any of the presently utilized colorimetric, spectrophotometric, fluorospectrophotometric, amperometric or gasometric techniques known in the art.

The present invention includes an assay system which may be prepared in the form of a test kit for the quantitative analysis of the extent of the presence of the TRF, or to identify drugs or other agents that may mimic or block their activity. The system or test kit may comprise a labelled component prepared by one of the radioactive and/or enzymatic techniques discussed herein, coupling a label to the TRFs, their agonists and/or antagonists, and one or more additional immunochemical reagents, at least one of which is a free or immobilized ligand, capable either of binding with the labelled component, its binding partner, one of the components to be determined or their binding partner(s).

In a further embodiment, the present invention relates to certain therapeutic methods which would be based upon the activity of the TRF(s), its (or their) subunits, or active fragments thereof, or upon agents or other drugs determined to possess the same activity. A first therapeutic method is associated with the prevention of the manifestations of conditions causally related to or following from the binding activity of the TRF or its subunits, and comprises administering an agent capable of modulating the production and/or activity of the TRF or subunits thereof, either individually or in mixture with each other in an amount effective to prevent the development of those conditions in the host. For example, drugs or other binding partners to the TRF or proteins may be administered to inhibit or potentiate TRF activity, as in the potentiation of TRF activity in aging, or the inhibition or modulation of TRF activity in cancer therapy.

More specifically, the therapeutic method generally referred to herein could include the method for the treatment of various pathologies or other cellular dysfunctions and derangements by the administration of pharmaceutical compositions that may comprise effective inhibitors or enhancers of activation of the TRF or its subunits, or other equally effective drugs developed for instance by a drug screening assay prepared and used in accordance with a further aspect of the present invention. For example, drugs or other binding partners to the TRF or proteins, as represented by SEQ ID NO:12, may be administered to inhibit or potentiate telomere lengthening activity, as in the potentiation of TRF in cancer therapy.

In particular, the isolated TRFs, proteolytic fragments of TRFs, truncated proteins, and peptides or proteins which comprise a particular structural/functional domain of a TRF, their antibodies, agonists, antagonists, or active fragments thereof, could be prepared in pharmaceutical formulations for administration in instances where appropriate, such as to treat cancer or counteract the aging process.

Accordingly, it is a principal object of the present invention to provide TRFs in purified form that exhibits certain characteristics and activities associated with telomere lengthening activity.

It is a further object of the present invention to provide antibodies to the TRFs, and methods for their preparation, including by recombinant means.

It is a further object of the present invention to provide a method for detecting the presence of the TRF and its subunits in mammals in which invasive, spontaneous, or idiopathic pathological states are suspected to be present.

It is a further object of the present invention to provide a method and associated assay system for screening substances such as drugs, agents and the like, potentially effective in either mimicking the activity or combating the adverse effects of the TRFs and/or its subunits in mammals.

It is a still further object of the present invention to provide a method for the treatment of mammals to control the amount or activity of the TRF or subunits thereof, so as to alter the adverse consequences of such presence or activity, or where beneficial, to enhance such activity.

It is a still further object of the present invention to provide a method for the treatment of mammals to control the amount or activity of the TRF or its subunits, so as to treat or avert the adverse consequences of invasive, spontaneous or idiopathic pathological states.

It is a still further object of the present invention to provide pharmaceutical compositions for use in therapeutic methods which comprise or are based upon the TRF, its subunits, their binding partner(s), or upon agents or drugs that control the production, or that mimic or antagonize the activities of the TRF.

Other objects and advantages will become apparent to those skilled in the art from a review of the ensuing description which proceeds with reference to the following illustrative drawings.

BRIEF DESCRIPTION OF THE DRAWINGS

FIGS. 1A–1B depicts peptide sequences derived from the purified TRF preparation (SEQ ID NOS:1–10).

FIGS. 2A–2B depicts the nucleotide sequence of human TRF mRNA (SEQ ID NO:11). The Xho I site used for construction of expression constructs (in vitro and in vivo) is indicated. The sequence contains a Met ATG codon with the surrounding sequence AAC<u>ATG</u>G, which is as expected for an initiation codon. The encoded protein is 439 amino acids in length, with a predicted molecular weight of about 51 kD. The fact that this is t somewhat smaller than the 67 kD protein observed on SDS-PAGE indicated that TRF may be modified or run anomalously on SDS-PAGE.

FIG. 3 depicts the deduced amino acid sequence of human TRF (SEQ ID NO:12). In italics is a region with a high percentage acidic residues ("acidic domain"), a hallmark of transcription factors. Underlined are the regions determined by peptide sequencing. Bolded is the region of homology to Myb type DNA binding repeats.

FIG. 4 depicts the alignment of human TRF sequence to Myb type DNA binding domains (SEQ ID NOS:13–19). Hu=human, Mu=mouse and Dro=Drosophila.

FIG. 7 depicts various staining patterns on HeLa cells.

FIG. 8: Characterization of the expression of TRF2. FIG. 8A depicts a Northern blot (Clontech) containing polyadenylated RNAs from the indicated human tissues probed with hTRF2, hTRF1, and a β-actin probe. FIG. 8*b* shows an SDS-PAGE of $^{35}$S-methionine labelled in vitro translation products obtained with cDNAs encoding mouse and human TRF1 and TRF2 (as indicated above the lanes).

FIG. 9A shows the alignment of the primary sequences of mouse and human TRF1 and TRF2. Identical amino acids are highlighted. The likely positions of the three helices constituting the Myb domain, as inferred from the NMR structure of c-Myb,[Ogata et al., *Cell* 79:639–648 (1994)] are indicated below the sequence.

FIG. 10: TRF2 binds duplex telomeric DNA with the same sequence specificity as TRF1. FIG. 10A shows the results of a gel-shift assay [Zhong et al. *Mol. Cell. Biol.* 13:4834–4843 (1992)] with whole cell extracts [Bianchi et al., *EMBO J.* 16:1785–1794 (1997)] from HeLa cells transfected with FLAG-tagged full length mTRF2 or the vector backbone as indicated below the lanes. Incubations contained either of the following additions: antibody 5 to hTRF1 [Luderus et al., *J. Cell. Biol.* 135:867–883 (1996)]. FLAG-antibody M2, or 200 ng of a plasmid (pTH5[19]) containing [TTAGGG]$_{27}$ as indicated above the lanes. FIG. 10B shows the results of a gel-shift assay with extracts of cells transfected with FLAG-tagged mTRF2ΔN-49 or the vector backbone. Additions as in a. Asterisks in a and b denote mTRF2-DNA complexes supershifted with the FLAG antibody. FIG. 10C shows the results of a gel-shift assay with mTRF2ΔN-49 as in b but in the presence of 50 and 100 ng circular plasmids containing 1–2 kb stretches of the indicated telomeric sequences [Hanish et al., *Proc. Natl Acad Sci USA* 91:8861–8865 (1994)] (lanes 3–14) or single-stranded [TTAGGG]$_6$ and [CCCTAA]$_6$ oligonucleotides (lanes 15–18). The reaction in lane 2 contained 50 ng pTH5. The probe used in FIGS. 10A–10C is a double-stranded restriction fragment containing the sequence [TTAGGG]$_{12}$ [Zhong et al., 1992, supra].

FIG. 11: Telomeric localization of TRF2 in transfected HeLa cells. FIG. 11A shows the detection of mTRF2 with the FLAG-antibody M2 (green) in transiently transfected HeLa cell. FIG. 11B shows the detection of telomeric DNA in the same nucleus with a [CCCUAA]$_{27}$ RNA probe (red), and FIG. 11C depicts the superimposition of FIGS. 11A–11B.

FIG. 12: TRF2 interacts with TRF2 but not with TRF 1. FIG. 12B depicts in vitro translated $^{35}$S-methionine labelled TRF1 and TRF2 proteins with or without an N-terminal FLAG tag (indicated above the lanes) were immunoprecipitated using the M2 anti-FLAG antibodies and analyzed by autoradiography.

FIG. 13. Inducible expression of TRF2 proteins in HTC75 cells.

FIG. 14. In vivo effects of the TRF2 mutants on telomere binding of endogenous wild-type TRF1 and TRF2 in transiently transfected HeLa cells. FIGS. 14A–B show the localization of endogenous wild-type TRF2 using antibody #508 (green/yellow) in an interphase nucleus (FIG. 14A) and on mitotic chromosomes (FIG. 14B) of HeLa cells. DNA was stained with DAPI (shown in red).

FIGS. 14C–D show HeLa cells transiently transfected with wild-type TRF were dual-labelled for TRF2 using antibody #508 (green in FIG. 14C) and endogenous TRF1 using mouse serum #2 (end TRF1, red in FIG. 14D). Three transfected cells overexpressing TRF2 are indicated by arrowheads; the other three cells were probably not transfected and showed levels of endogenous TRF2 similar to untransfected control cells.

FIGS. 14 E–H show HeLa cells transiently transfected with TRF2$^{\Delta B}$ that were dual-labelled for FLAG-tagged mutant protein using antibody M2 (green in FIG. 14E and FIG. 14G) and either endogenous TRF2 (endTRF2, red in FIG. 14F) or endogenous TRF1 (endTRF1, red in FIG. 14H).

FIGS. 14I–L show HeLa cells transiently transfected with TRF2$^{\Delta B \Delta M}$ that were dual-labelled for FLAG-tagged mutant protein using antibody M2 (green in FIGS. 14I and 14K) and either endogenous TRF2 (red in FIG. 14J) or endogenous TRF1 (red in FIG. 14L). DAPI staining of nuclear DNA in C–L is shown in blue.

FIG. 15. Growth arrest and induction of a senescent phenotype in response to TRF2 mutants. FIGS. 15A and 15B contain graphs showing the effect of induction of full length TRF2 (clone P12), TRF2$^{\Delta B}$ (clone S13), and TRF2$^{\Delta B \Delta M}$ (clone T4) on the growth of HTC75 cells. B27 is a clonal HTC75 cell line containing the vector.

FIG. 16 depicts the induction of anaphase bridges and metaphase fusions by TRF2$^{\Delta B \Delta M}$.

FIG. 16F shows metaphase chromosomes G-banded with Trypsin showing multiple end-to-end fusions. FIG. 16G shows the detection of telomeric TTAGGG repeats at the sites of telomere fusion (arrowheads). TTAGGG repeats were detected using a fluorescently labelled PNA [CCCTAA]$_3$ probe (green). DNA was stained with DAPI.

FIG. 17. Detection of telomere fusions in naked DNA.

FIGS. 17A–F shows all genomic DNA samples were digested with Hinf1 and Rsa1 and analyzed by blotting using a TTAGGG repeat scientific probe (see Experimental Procedures in Example 8). The position of λHindIII DNA marker fragments (23, 9.4, 6.6, 4.4, 2.3, and 2.0 kb) is indicated next to each blot.

FIG. 18. Expression of TRF2$^{\Delta B \Delta M}$ causes loss of G-strand overhang signals in the presence of telomerase activity. FIG. 18A shows the G-strand overhang assays performed on DNA derived from the indicated cell lines (grown in the presence or absence of doxycyclin for 9 days as indicated) expressing the indicated TRF2 polypeptides.

FIG. 18B depicts the time course of the loss of G-tails in the T4 clone expressing TRF2$^{\Delta B \Delta M}$.

DETAILED DESCRIPTION

Figure 5:
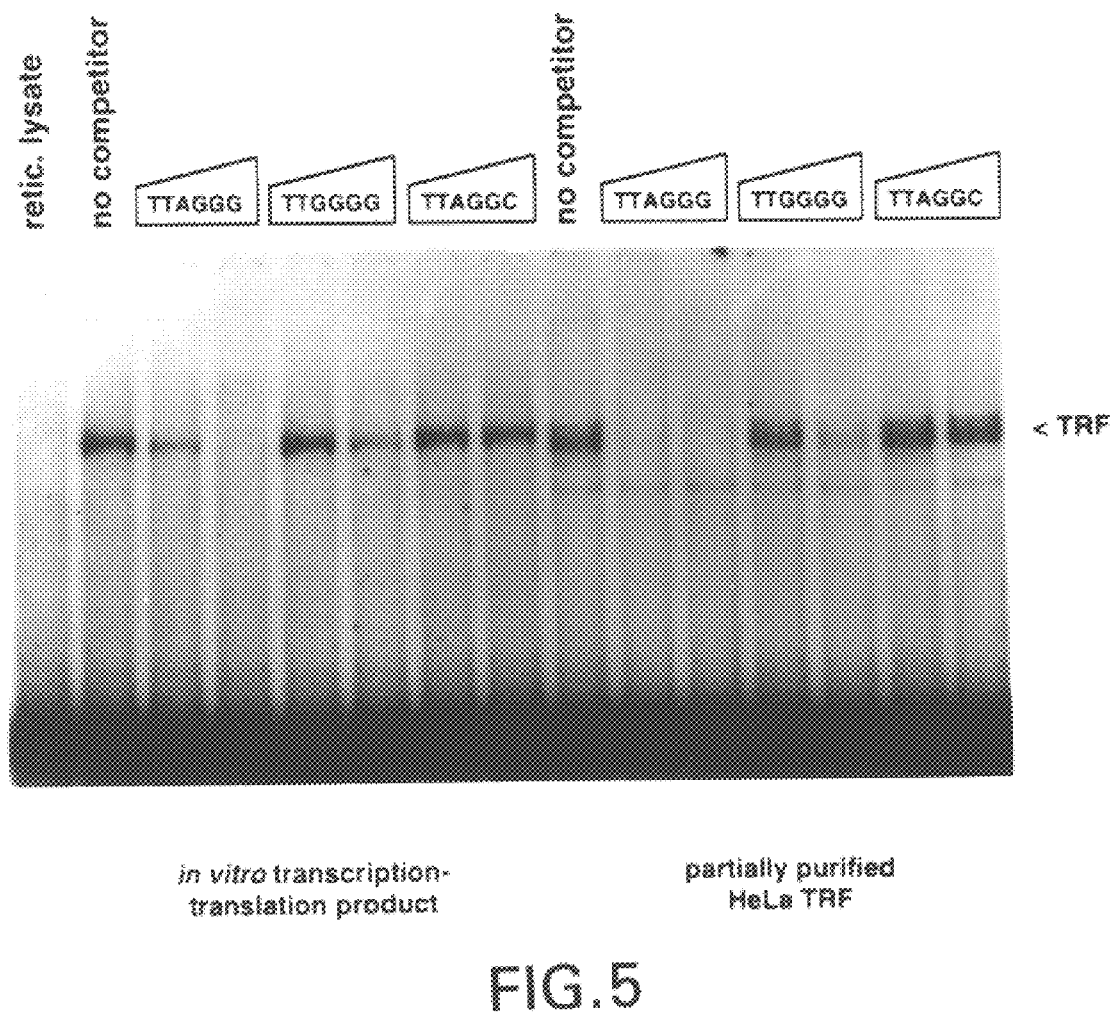
FIG. 5 depicts a gel-shift experiment showing telomeric repeat binding activity of protein encoded by the human HTRF4.1 cDNA. The human cDNA was fused onto a His6 tag and a initiator codon and expressed by in vitro transcription (T7 RNA polymerase) and translation in a rabbit reticulocyte lysate. No gel shift complex is formed in the absence of human TRF cDNA. The probe is a $(TTAGGG)_{12}$ containing restriction fragment. Competitions were done with plasmids containing long arrays of telomeric DNAs with the indicated sequence. Gel-shift methods are as described by [Zhong et al., *Mol. Cell Biol.*, 13:4834–4843 (1992)]. The data indicate that the human TRF binds TTAGGG repeats with the same sequence specificity as HeLa TRF activity.

The present invention provides vertebrate telomeric binding factors (TRFs) that bind specifically to duplex TTAGGG repeats in vitro. Human TRFs, for example, are localized to all human telomeres in metaphase. The binding of the TRFs to telomeres plays an important role in telomere elongation and maintenance. The TRFs of the present invention contain a distinctive polar N-terminal domain, a dimerization domain, and a Myb domain. TRFs function as homodimers in solution and require two Myb motifs to bind to telomeric DNA in vitro and in vivo.

There are two classes of TRFs, TRF1s and TRF2s. TRF1 and TRF2 do not readily form heterodimers with each other, if at all. Further, although the structural motif of the both classes of TRFs contain the same three structural/functional domains listed above, both the dimerization domain and the polar N-terminal domains of TRFs differ appreciably. Indeed, whereas mammalian TRF1 has an acidic N-terminal domain, mammalian TRF2 has a basic N-terminal domain. Similarly, the lack of heterodimers indicates that the dimerization domains of the two classes of TRFs do not bind to each other. The structural features of the proteins and more particularly the individual domains allows the two classes to be readily distinguished in either functional assays or in drug assays in which the object would be to attenuate the function of one of the classes of TRFs while minimally effecting the function of the other class.

As described herein, TRF2 is a human telomeric protein that is required to maintain the correct structure at telomere termini, and protects against end-to-end fusions. In addition, TRF2 plays a role in the successful progression through the cell division cycle. As such, TRF2 is involved in the main functions ascribed to telomeres in somatic human cells and is therefore a likely player in the loss of telomere function and growth arrest that accompanies telomere shortening in normal and transformed human cells.

The mechanism by which telomeres prevent end-to-end fusion has heretofore remained elusive. Human telomeres are bound by two TTAGGG repeat binding factors: TRF1, a negative regulator of telomere maintenance, and TRF2, a homolog of TRF1. TRF2 is shown herein to be required for cellular proliferation and for the protection of chromosome ends in human cells. Overexpression of two deletion derivatives of TRF2 lacking its basic N-terminus induced an irreversible growth arrest with characteristics of cellular senescence. A strong dominant negative allele causing the loss of endogenous TRF2 from telomeres, induced end-to-end chromosome fusions detectable in metaphase and anaphase cells. Telomeric DNA persisted at the fusions, demonstrating that TTAGGG repeat arrays per se are not sufficient to maintain telomere integrity. Telomeric fusions were detectable in native genomic DNA as joined terminal restriction fragments and molecular analysis suggested that they represented ligation of chromosome ends that have lost their single-stranded G-tails. TRF2 protects chromosome ends from fusion, through the maintenance of the correct structure at telomere termini. The chromosome end fusions and growth arrest observed in senescent primary human cells and certain malignant cells are caused by the logs of TRF2 from the critically shortened telomeres in these cells.

Figure 19:
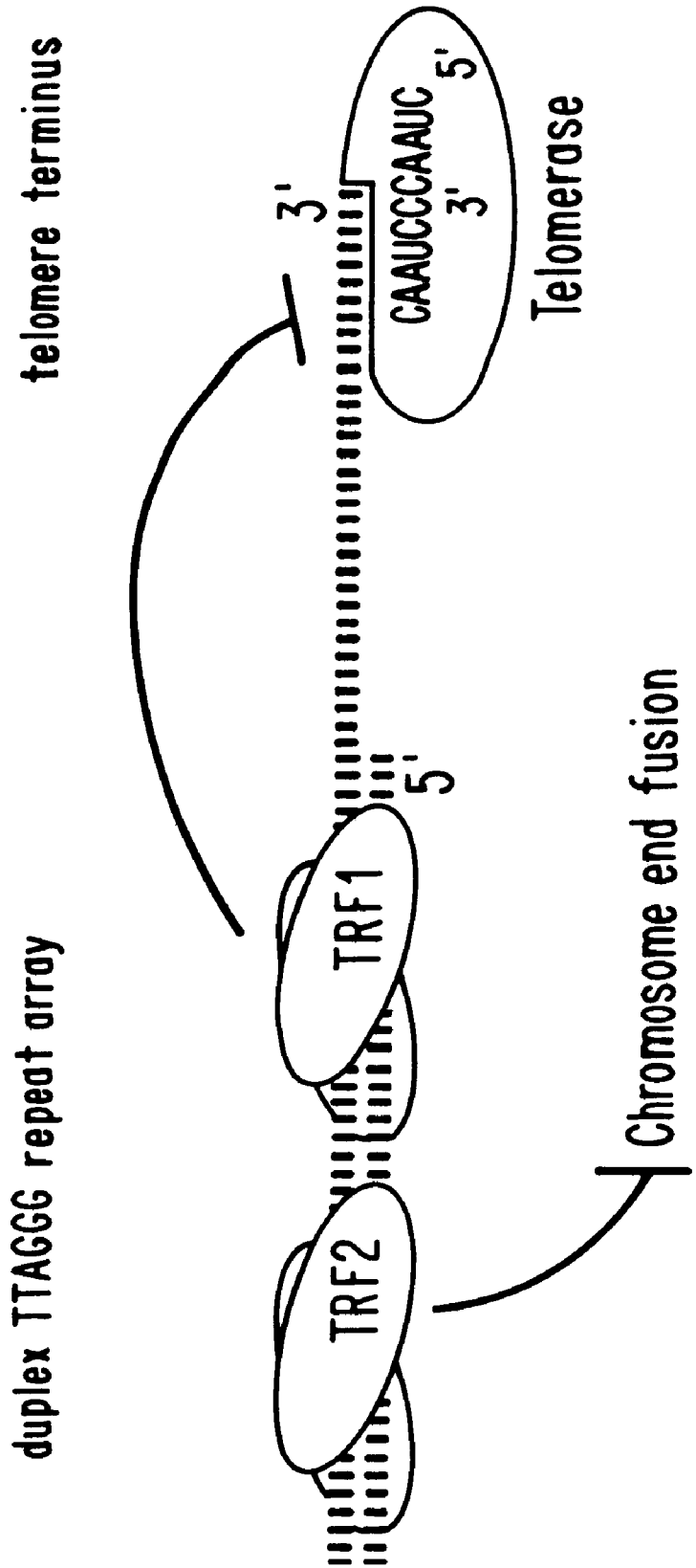
FIG. 19 illustrates the role of human telomeric proteins in telomere protection and telomere length regulation. TRF1 is depicted as a negative regulator of telomere maintenance, proposed to act by inhibiting telomerase at individual chromosome ends [van Steensel and de Lange, Nature, 385:740–743 (1997); U.S. patent application Ser. No. 08/800,264, filed Feb. 13, 1997, herein incorporated by reference in its entirety] TRF2 is involved in the protection of chromosome ends by inhibiting end-to-end fusions. Thus, in the process of adding TTAGGG repeats, telomerase synthesizes binding sites for two proteins onto chromosome ends, one of which ensures telomere integrity and the other regulates the length of the telomeres.

A general view of the logic underlying the function of human telomeres is now emerging (FIG. 19). Human telomerase has long been understood to maintain the terminal sequences of human chromosome ends and thus counter DNA attrition with cell divisions. The need for telomere length maintenance is particularly obvious in immortalized cells and in the germline. The results described herein reveal a second function for telomerase. In addition to balancing the terminal sequence loss that accompanies DNA replication, in the process of synthesizing arrays of TTAGGG repeats, telomerase also ensures the continued presence of TRF2 binding sites at chromosome ends. Since TRF2 is required to prevent telomere fusions, telomerase thus maintains the protective activity of telomeres by constantly replenishing TRF2 binding sites that are lost from telomere termini with DNA replication. This second function of telomerase critically depends on the sequence of the telomeric repeats its synthesizes and this model predicts that the exact sequence of the telomerase products is a key aspect of the mechanism of telomere function.

In this regard, mutations of the telomerase template RNA in Tetrahymena has given rise to dramatic cellular phenotypes [Yu et al., *Nature*, 344:126–132 (1990); Kirk et al., *Science*, 275:1478–1481 (1997)], including occasional anaphase bridges that may well represent telomere fusions of the type reported herein. Tetrahymena telomeric binding proteins that could have been displaced by the altered telomeric repeats have not yet been identified.

Addition of TTAGGG repeats to chromosome ends also ensures the binding of a second telomeric protein, TRF1, that acts as a negative regulator of telomerase, and modulates the length of the TTAGGG repeats arrays at chromosome ends [van Steensel and de Lange, *Nature*, 385:740–743 (1997); U.S. patent application Ser. No. 08/800,264 filed Feb. 13, 1997, herein incorporated by reference in its entirety]. Thus, the telomerase-mediated maintenance of telomeric TTAGGG repeats secures a functional and regulated telomeric complex required for the integrity of chromosome ends. Selective chromosome end fusions and growth arrest in, malignant cells, for example can be effected by inhibiting TRF2 by agents identified by methods and compositions disclosed herein.

Since both TRF1 and TRF2 have the ability to bind to double-stranded TTAGGG repeats, they can be used as tools for the targeting of protein domains to TTAGGG repeats in vitro and in vivo. For example, the Green Fluorescent Protein (GFP) can be targeted to telomeres by fusion to TRF1. Such specific targeting of protein domains to TTAGGG repeat regions in the genome can act as important research tools for telomere length monitoring etc. Furthermore, TRF1 and TRF2 can also be used in the construction of mammalian artificial chromosomes. Artificial chromosomes have great utility in gene therapy and basic research. Artificial chromosomes depend on the functionality of their telomere ends. Since telomeres depend on the function of both TRF1 and TRF2, coating the telomere termini of artificial chromosomes with TRF1 and/or TRF2 strongly enhances the frequency of artificial chromosome formation. In particular the activity of TRF2 as a telomere protection protein can be crucial in the generation of functional telomeres.

Overexpression of TRF1 in human HTC75 cells has resulted in cell lines with critically shortened telomeres (e.g. the D4 cell line of U.S. patent application Ser. No. 08/800, 264 filed Feb. 13, 1997). Because their telomeres are unusually short, such cell lines are expected to show a highly increased sensitivity to the inhibition of telomerase and could be used as a screening tool for the in vivo effects of telomerase inhibitors identified by in vitro screening strategies.

Therefore, the present invention provides nucleic acids, antibodies, proteins and fragments thereof and methodology using the same which can be utilized in basic research and/or the clinical setting, e.g., to monitor, probe, diagnose and potentially treat conditions involving telomere maintenance.

The direct correlation shown between telomere maintenance and cellular senescence, for example [Bodner et al., *Science*, 279:349–352 (1998)] indicates that the compositions of matter and processes provided by the present invention can also play a direct role in preventing and/or treating (1) atrophy of the skin through loss of extracellular matrix homeostasis in dermal fibroblasts [Takeda et al., *Arch. Dermatol.*, 130:87 (1994)]; (2) age-related macular degeneration [Boulton et al., *J. Neurosci.*, 15:4992 (1995)]; and (3) atherosclerosis [Kamazaki et al., *J. Med. Sci.*, 42:97 (1993)]. In addition, Bodner et al. [supra] have pointed out that cells having an extended life-span can also have important ex vivo applications in the production of bioengineered products and even in gene therapy.

Nucleic Acids, Peptides and Proteins

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, N.Y. (herein "Sambrook et al., 1989); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds (1985)]; *Transcription and Translation* [B. D. Hames & S. J. Higgins, eds. (1984)]; *Animal Cell Culture* R. I. Freshney, ed. (1986)]; *Immobilized Cells and Enzymes* [IRL Press, (1986)]; B. Perbal, *A Practical Guide to Molecular Cloning* (1984); F. M. Ausubel et al. (eds.), *Current Protocols in Molecular Biology*, John Wiley & Sons, Inc. (1994).

Therefore, if appearing herein, the following terms shall have the definitions set out below.

The terms "telomere repeat binding factor", "telomeric repeat binding factor", "telomeric binding factor", "TTAGGG repeat binding factor", and "TRF," and any variants not specifically listed, may be used herein interchangeably, and as used throughout the present application and claims refer to proteinaceous material including single or multiple proteins, including the functional dimeric form of the protein and extends to those proteins having the amino acid sequences described herein, and the profile of activities set forth herein. Accordingly, proteins displaying substantially equivalent or altered activity are likewise contemplated. These modifications may be deliberate, for example, such as modifications obtained through site-directed mutagenesis, or may be accidental, such as those obtained through mutations in hosts that are producers of the complex or its named subunits. Also, the terms "telomere repeat binding factor," and "TRF" are intended to include within their scope proteins specifically recited herein as well as all substantially homologous analogs and allelic variations. There are two classes of TRFs, TRF1s and TRF2s both of which are contained in the group of proteins labelled as TRFs.

A "structural/functional domain" is used herein to indicate a specific domain of a TRF which can identified by a structural and/or a functional characteristic such as a polar N-terminal domain, a dimerization domain, and a Myb domain. The polar N-terminal domain of TRF1 is acidic, whereas that of TRF2 is basic.

A "basic N-terminal domain" as used herein comprises an amino acid sequence at the N-terminal segment of a TRF that contains 30 to 90 amino acids, preferably 40 to 60 amino acids which has a ratio of basic amino acids to acidic amino acids of greater than 1.5:1 and preferably greater than 2:1. Examples of such basic N-terminal amino acids include SEQ ID NOs:37 and 39.

An "acidic N-terminal domain" as used herein comprises an amino acid sequence at the N-terminal segment of a TRF that contains 30 to 90 amino acids, preferably 40 to 75 amino acids which has a ratio of acidic amino acids to basic amino acids of greater than 2:1 and preferably greater than 3:1. Examples of such basic N-terminal amino acids include SEQ ID NOs:32 and 35.

The amino acid residues described herein are preferred to be in the "L" isomeric form. However, residues in the "D" isomeric form can be substituted for any L-amino acid residue, as long as the desired functional property of the protein is retained by the polypeptide.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of about 15 or more nucleotides, preferably more than about 24. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15–25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

Mutations can be made in nucleotide sequences of the present invention such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such conservative amino acid changes define the term "a conservative amino acid substitution" as used herein, which is used to denote one or more conservative changes.

A conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein.

The following is one example of various groupings of amino acids:
Amino Acids with Nonpolar R Groups
  Alanine
  Valine
  Leucine
  Isoleucine
  Proline
  Phenylalanine
  Tryptophan
  Methionine
Amino Acids with Uncharged Polar R Groups
  Glycine
  Serine
  Threonine
  Cysteine
  Tyrosine
  Asparagine
  Glutamine
Amino Acids with Charged Polar R Groups (negatively charged at Ph 6.0)
  Aspartic acid
  Glutamic acid
Basic Amino Acids (positively charged at pH 6.0)
  Lysine
  Arginine
  Histidine (at pH 6.0)
Another grouping may be those amino acids with phenyl groups:
  Phenylalanine
  Tryptophan
  Tyrosine
  Particularly preferred substitutions are:
  Lys for Arg and vice versa such that a positive charge may be maintained;
  Glu for Asp and vice versa such that a negative charge may be maintained;
  Ser for Thr such that a free —OH can be maintained; and
  Gln for Asn such that a free $NH_2$ can be maintained.

Amino acid substitutions may also be introduced to substitute an amino acid with a particularly preferable property. For example, a Cys may be introduced a potential site for disulfide bridges with another Cys. A His may be introduced as a particularly "catalytic" site (i.e., His can act as an acid or base and is the most common amino acid in biochemical catalysis). Pro may be introduced because of its particularly planar structure, which induces β-turns in the protein's structure.

A "heterologous nucleotide sequence" as used herein is a nucleotide sequence that is added to a nucleotide sequence of the present invention by recombinant methods to form a nucleic acid which is not naturally formed in nature. Such nucleic acids can encode chimeric and/or fusion proteins. Thus the heterologous nucleotide sequence can encode peptides and/or proteins which contain regulatory and/or structural properties. In another such embodiment the heterologous nucleotide can encode a protein or peptide that functions as a means of detecting the protein or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence call comprise non-coding sequences including restriction sites, regulatory sites, promoters and the like.

A "heterologous region" of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

As used herein, the terms "restriction endonucleases" and "restriction enzymes" refer to bacterial enzymes, each of which cut double-stranded DNA at or near a specific nucleotide sequence.

Two DNA sequences are "substantially homologous" when at least about 60% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra. Likewise, two polypeptide sequences are "substantially homologous" when at least about 60% (preferably at least about 80%, and most preferably at least about 90 or 95%) of the amino acids are either identical or contain conservative changes, as defined above, over the defined length of the polypeptide sequences.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. For preliminary screening for homologous nucleic acids, low stringency hybridization conditions are used corresponding to 50° C. as described by Church and Gilbert [*Proc. Natl. Acad. Sci. USA*, 81:1991–1995 (1984)]. Washes are performed in 2×SSC/0.1% SDS at 50° C. Moderate stringency hybridization conditions correspond to a higher temperature e.g., 60° C. High stringency hybridization conditions are performed at 65° C. Washes in this case are performed in 0.3×SSC/0.1% SDS at 65° C. Hybridization require that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–0.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid is at least about 12 nucleotides; preferably at least about 18 nucleotides; and more preferably the length is at least about 27 nucleotides; and most preferably 36 nucleotides or more.

In a specific embodiment, the term "standard hybridization conditions" refers to a $T_m$ of 55° C., and utilizes conditions as set forth above. In a preferred embodiment, the $T_m$ is 60° C.; in a more preferred embodiment, the $T_m$ is 65° C.

The term "standard hybridization conditions" refers to salt and temperature conditions substantially equivalent to 5×SSC and 65° C. for both hybridization and wash.

The term "approximately" is used interchangeably with the term "about" and means that the value may vary by 10%, preferably no more than 5%, and most preferably no more than 2%.

Another feature of this invention is the expression of the DNA sequences disclosed herein. As is well known in the art, DNA sequences may be expressed by operatively linking them to an expression control sequence in an appropriate expression vector and employing that expression vector to transform an appropriate unicellular host. Such operative linking of a DNA sequence of this invention to an expression control sequence, of course, includes, if not already part of the DNA sequence, the provision of an initiation codon, ATG, in the correct reading frame upstream of the DNA sequence.

A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., *E. coli* plasmids col E1, pCR1, pBR322, pMB9 and their derivatives, plasmids such as RP4; phage DNAS, e.g., the numerous derivatives of phage λ, e.g., NM989, and other phage DNA, e.g., M13 and Filamentous single stranded phage DNA; yeast plasmids such as the 2 μplasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast α-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of *E. coli*, Pseudomonas, Bacillus, Streptomyces, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. For example, in selecting a vector, the host must be considered because the vector must function in it. The vector's copy number, the ability to control that copy number, and the expression of any other proteins encoded by the vector, such as antibiotic markers, will also be considered.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

Considering these and other factors a person skilled in the art will be able to construct a variety of vector/expression control sequence/host combinations that will express the DNA sequences of this invention on fermentation or in large scale animal culture.

In a specific embodiment, an TRF fusion protein or peptide can be expressed. A TRF fusion protein comprises at least a functionally active portion of a non-TRF protein joined via a peptide bond to a TRF or a structural/functional domain of a TRF. Similarly a TRF fusion peptide can be expressed. The non-TRF sequences can be amino- or carboxyl-terminal to the TRF sequences. For stable expression of a TRF fusion protein, the portion of the non-TRF fusion protein or peptide can be joined via a peptide bond to the amino terminus of the TRF protein. A recombinant DNA molecule encoding such a fusion protein comprises a sequence encoding at a functionally active portion of a non-TRF protein or peptide joined in-frame to the TRF coding sequence, and preferably encodes a cleavage site for a specific protease, e.g., thrombin or Factor Xa, preferably at the TRF-non-TRF juncture. In a specific embodiment, the fusion protein is expressed in *Escherichia coli*. An example of a fusion peptide is a TRF having a FLAG-tag as described in Example 7 below. An example of a fusion protein is a TRF or a structural/functional domain of a TRF joined with a green fluorescent protein or modified green fluorescent protein as described in U.S. Pat. No. 5,625,048, Issued Apr. 29, 1997 herein incorporated by reference in its entirety.

Such fusion proteins and peptides may also be classified as chimeric proteins or peptides which further include TRFs having switched structural/functional domains such as a TRF having an acidic N-terminal domain and a Myb domain of a TRF1, and a dimerization domain of a TRF2. All of such chimeric TRFs including the fusion proteins and peptides are contemplated in the present invention.

It is further intended that TRF analogs may be prepared from nucleotide sequences of the protein complex/subunit derived within the scope of the present invention. Analogs, such as fragments, may be produced, for example, by pepsin digestion of TRF material. Other analogs, such as muteins, can be produced by standard site-directed mutagenesis of TRF coding sequences. Analogs exhibiting "TRF activity" such as small molecules, whether functioning as promoters or inhibitors, may be identified by known in vivo and/or in vitro assays.

As mentioned above, a DNA sequence encoding a TRF can be prepared synthetically rather than cloned. The DNA sequence can be designed with the appropriate codons for the TRF amino acid sequence. In general, one will select preferred codons for the intended host if the sequence will be used for expression. The complete sequence is assembled from overlapping oligonucleotides prepared by standard methods and assembled into a complete coding sequence. See, e.g., Edge, *Nature*, 292:756 (1981); Nambair et al., *Science*, 223:1299 (1984); Jay et al., *J. Biol. Chem.*, 259:6311 (1984).

Synthetic DNA sequences allow convenient construction of genes which will express TRF analogs or "muteins". Alternatively, DNA encoding muteins can be made by site-directed mutagenesis of native TRF genes or cDNAs, and muteins can be made directly using conventional polypeptide synthesis.

A general method for site-specific incorporation of unnatural amino acids into proteins is described in Christopher J. Noren, Spencer J. Anthony-Cahill, Michael C. Griffith, Peter G. Schultz, *Science*, 244:182–188 (April 1989). This method may be used to create analogs with unnatural amino acids.

Antibodies

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. One antibody of the present invention is exemplified by an antibody to human TRF2 in Example 8.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The general methodology for making monoclonal antibodies by hybridomas is well known. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against TRF peptides can be screened for various properties; i.e., isotype, epitope, affinity, etc. Of particular interest are monoclonal antibodies that neutralize the binding activity of the TRF or its subunits. Such monoclonals can be readily identified in, for example, gel-shift assays. High affinity antibodies are also useful when immunoaffinity purification of native or recombinant TRF is possible.

Preferably, the anti-TRF antibody used in the diagnostic methods of this invention is an affinity purified polyclonal antibody. More preferably, the antibody is a monoclonal antibody (mAb). In addition, it is preferable for the anti-TRF antibody molecules used herein be in the form of Fab, Fab', F(ab')$_2$ or F(v) portions of whole antibody molecules.

Methods for producing polyclonal anti-polypeptide antibodies are well-known in the art. See U.S. Pat. No. 4,493, 795 to Nestor et al. A monoclonal antibody, typically containing Fab and/or F(ab')$_2$ portions of useful antibody molecules, can be prepared using the hybridoma technology described in *Antibodies-A Laboratory Manual*, Harlow and Lane, eds., Cold Spring Harbor Laboratory, New York (1988), which is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a TRF-binding portion thereof, or TRF, or a DNA-binding portion thereof.

Splenocytes are typically fused with myeloma cells using polyethylene glycol (PEG) 6000. Fused hybrids are selected by their sensitivity to HAT. Hybridomas producing a monoclonal antibody useful in practicing this invention are identified by their ability to immunoreact with the present TRF and their ability to inhibit specified activity at telomeres in target cells, A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Media useful for the preparation of these compositions are both well-known in the art and commercially available and include synthetic culture media, inbred mice and the like. An exemplary synthetic medium is Dulbecco's minimal essential medium (DMEM) [Dulbecco et al., Virol. 8:396 (1959)] supplemented with 4.5 gm/l glucose, 20 mm glutamine, and 20% fetal calf serum. An exemplary inbred mouse strain is the Balb/c.

Methods for producing monoclonal anti-TRF antibodies are also well-known in the art. See Niman et al. [*Proc. Natl. Acad. Sci. USA*, 80:4949–4953 (1993)]. Typically, the present TRF or a peptide analog is used either alone or conjugated to an immunogenic carrier, as the immunogen in the before-described procedure for producing anti-TRF monoclonal antibodies. The hybridomas are screened for the ability to produce an antibody that immunoreacts with the TRF peptide analog and the present TRF.

Diagnostics and Therapeutics

The phrase "pharmaceutically acceptable" refers to molecular entities and composition that are physiologically tolerable and do not typically produce an allergic or similar untoward reaction, such as gastric upset, dizziness and the like, when administered to a human.

The phrase "therapeutically effective amount" is used herein to mean an amount sufficient to prevent, and preferably reduce by at least about 30 percent, more preferably by at least 50 percent, most preferably by at least 90 percent, a clinically significant change in the S phase activity of a target cellular mass, or other feature of pathology such as for example, elevated blood pressure, fever or white cell count as may attend its presence and activity.

The possibilities both diagnostic and therapeutic that are raised by the existence of the TRF, derive from the fact that the factors appear to participate in direct and causal protein-DNA interaction between the repeat sequences that are bound by their binding factors, and those factors that thereafter directly interface with the DNA repeat sequence and effect telomere length and accordingly the health and/or proliferative capacity of the cell. As suggested earlier and elaborated further on herein, the present invention contemplates pharmaceutical intervention in the cascade of reactions in which the TRF is implicated, to modulate the activity initiated by the binding factor bound to the repeat sequence.

In instances where it is desired to modulate the length or function of a telomere resulting from a particular stimulus or factor, an appropriate modulator of the TRF could be introduced to block the interaction of the TRF with those repeat sequences causally connected with telomere maintenance.

As discussed earlier, the TRF or their binding partners or other ligands or agents exhibiting either mimicry or antagonism to the TRF or control over their production, may be prepared in pharmaceutical compositions, with a suitable carrier and at a strength effective for administration by various means to a patient experiencing an adverse medical condition associated with abnormal telomere length, stimulation for the treatment thereof. A variety of administrative techniques may be utilized, among them parenteral techniques such as subcutaneous, intravenous and intraperitoneal injections, catheterizations and the like. Average quantities of the TRFs or their subunits may vary and in particular should be based upon the recommendations and prescription of a qualified physician or veterinarian.

Also, antibodies including both polyclonal and monoclonal antibodies, and drugs that modulate the production or activity of the TRF and/or their subunits may possess certain diagnostic applications and may for example, be utilized for the purpose of detecting and/or measuring conditions such as viral infection or the like. For example, the TRF or its structural/functional domains may be used to produce both polyclonal and monoclonal antibodies to themselves in a variety of cellular media, by known techniques such as the hybridoma technique utilizing, for example, fused mouse spleen lymphocytes and myeloma cells. Likewise, small molecules that mimic or antagonize the activity(ies) of the TRF of the invention may be discovered or synthesized, and may be used in diagnostic and/or therapeutic protocols.

As suggested earlier, the diagnostic method of the present invention comprises examining a cellular sample or medium by means of an assay including an effective amount of an antagonist to a TRF protein, such as an anti-TRF antibody, preferably an affinity-purified polyclonal antibody, and more preferably a mAb. In addition, it is preferable for the anti-TRF antibody molecules used herein be in the form of Fab, Fab', F(ab')$_2$ or F(v) portions or whole antibody molecules. As previously discussed, patients capable of benefiting from this method include those suffering from cancer, a pre-cancerous lesion, a viral infection or other like pathological derangement. Methods for isolating and inducing anti-TRF antibodies and for determining and optimizing the ability of anti-TRF antibodies to assist in the examination of the target cells are all well-known in the art.

The present invention further contemplates therapeutic compositions useful in practicing the therapeutic methods of this invention. A subject therapeutic composition includes, in admixture, a pharmaceutically acceptable excipient (carrier) and one or more of a TRF, polypeptide analog thereof or fragment thereof, as described herein as an active ingredient. In a preferred embodiment, the composition comprises an antigen capable of modulating the specific binding of the present TRF within a target cell.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization of TRF binding capacity desired. Precise amounts of active ingredient required to be administered depend on the judgment of the practitioner and are peculiar to each individual. However, suitable dosages may range from about 0.1 to 20, preferably about 0.5 to about 10, and more preferably one to several, milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

The present invention also relates to a variety of diagnostic applications, including methods for detecting the presence of stimuli such as the earlier referenced polypeptide ligands, by reference to their ability to elicit the activities which are mediated by the present TRF. As mentioned earlier, the TRFs can be used to produce antibodies to itself by a variety of known techniques, and such antibodies could then be isolated and utilized as in tests for the presence of particular activity of TRF at telomeres in suspect target cells.

Antisense, Gene Targeting and Ribozymes

The functional activity of TRF can be evaluated transgenically. In this respect, a transgenic mouse model can be used. The TRF gene can be used in complementation studies employing transgenic mice. Transgenic vectors, including viral vectors, or cosmid clones (or phage clones) corresponding to the wild type locus of candidate gene, can be constructed using the isolated TRF gene. Cosmids may be introduced into transgenic mice using published procedures [Jaenisch, Science, 240,1468–1474 (1988)]. In a genetic sense, the transgene acts as a suppressor mutation.

Alternatively, a transgenic animal model can be prepared in which expression of the TRF gene is disrupted. Gene expression is disrupted, according to the invention, when no functional protein is expressed. One standard method to evaluate the phenotypic effect of a gene product is to employ knock-out technology to delete the gene (see U.S. Pat. No. 5,464,764 Issued Nov. 7, 1995 herein incorporated by reference in its entirety.)

The present invention also extends to the preparation of antisense nucleotides and ribozymes that may be used to interfere with the expression of the TRF at the translational level. This approach utilizes antisense nucleic acid and ribozymes to block translation of a specific mRNA, either by masking that mRNA with an antisense nucleic acid or cleaving it with a ribozyme.

Antisense nucleic acids are DNA or RNA molecules that are complementary to at least a portion of a specific mRNA molecule. [See Weintraub, (1990); Marcus-Sekura, (1988)]. In the cell, they hybridize to that mRNA, forming a double stranded molecule. The cell does not translate an mRNA in this double-stranded form. Therefore, antisense nucleic acids interfere with the expression of mRNA into protein. Oligomers of about fifteen nucleotides and molecules that hybridize to the AUG initiation codon will be particularly efficient, since they are easy to synthesize and are likely to pose fewer problems than larger molecules when introducing them into TRF-producing cells. Antisense methods have been used to inhibit the expression of many genes in vitro [Marcus-Sekura, (1988); Hambor et al., (1988)].

Ribozymes are RNA molecules possessing the ability to specifically cleave other single stranded RNA molecules in a manner somewhat analogous to DNA restriction endonucleases. Ribozymes were discovered from the observation that certain mRNAs have the ability to excise their own introns. By modifying the nucleotide sequence of these RNAs, researchers have been able to engineer molecules that recognize specific nucleotide sequences in an RNA molecule and cleave it [Cech, (1988)]. Because they are sequence-specific, only mRNAs with particular sequences are inactivated.

Investigators have identified two types of ribozymes, Tetrahymena-type and "hammerhead"-type. [Hasselhoff and Gerlach, (1988)] Tetrahymena-type ribozymes recognize four-base sequences, while "hammerhead"-type recognize eleven- to eighteen-base sequences. The longer the recognition sequence, the more likely it is to occur exclusively in the target mRNA species. Therefore, hammerhead-type ribozymes are preferable to Tetrahymena-type ribozymes for inactivating a specific mRNA species, and eighteen base recognition sequences are preferable to shorter recognition sequences.

The DNA sequences described herein may thus be used to prepare antisense molecules against, and ribozymes that cleave mRNAs for TRF and their ligands.

Labels

The TRFs, structural/functional domains of TRFs, and their antibodies, nucleic acids encoding TRFs, structural/ functional domains of TRFs and probes to the nucleic acids may all be labelled The labels most commonly employed for these studies are radioactive elements, enzymes, chemicals which fluoresce when exposed to ultraviolet light, and others.

A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate.

The TRF or its binding partner(s) can also be labelled with a radioactive element or with an enzyme. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

Assays for Agonists and Antagonists of TRFs

Identification and isolation of a gene encoding a TRF of the invention provides for expression of TRF in quantities greater than can be isolated from natural sources, or in indicator cells that are specially engineered to indicate the activity of TRF expressed after transfection or transformation of the cells. Accordingly, in addition to rational design of agonists and antagonists based on the structure of TRF, the present invention contemplates an alternative method for identifying specific ligands of TRF using various screening assays known in the art.

Any screening technique known in the art can be used to screen for TRF agonists or antagonists. The present invention contemplates screens for small molecules that bind to TRF and agonize or antagonize TRF in vitro and/or in vivo. For example, natural products libraries can be screened using assays of the invention for molecules that agonize or antagonize the activity of TRF (see Example 7 for assays which test the ability of a TRF to bind a telomeric repeat sequence).

Knowledge of the primary sequence of the TRF, and the similarity of that sequence with other DNA binding proteins, can provide an initial clue as the inhibitors or antagonists of the TRF. Identification and screening of antagonists is further facilitated by determining structural features of the protein, e.g., using X-ray crystallography, neutron diffraction, nuclear magnetic resonance spectrometry, and other techniques for structure determination. These techniques provide for the rational design or identification of agonists and antagonists.

Another approach uses recombinant bacteriophage to produce large libraries. Using the "phage method" [Scott and Smith, *Science*, 249:386–390 (1990); Cwirla, et al., *Proc. Natl. Acad. Sci.*, 87:6378–6382 (1990); Devlin et al., *Science*, 249:404–406 (1990)), very large libraries can be constructed ($10^6$–$10^8$ chemical entities). A second approach uses primarily chemical methods, of which the Geysen method [Geysen et al., *Molecular Immunology*, 23:709–715 (1986); Geysen et al. *J. Immunologic Method*, 102:259–274 (1987)] and the method of Fodor et al. [*Science*, 251:767–773 (1991)] are examples. Furka et al. [*14th International Congress of Biochemistry*, Volume 5, Abstract FR:013 (1988); Furka, *Int. J. Peptide Protein Res.*, 37:487–493 (1991)], Houghton [U.S. Pat. No. 4,631,211, issued December 1986] and Rutter et al. [U.S. Pat. No. 5,010,175, issued Apr. 23, 1991] describe methods to produce a mixture of peptides that can be tested as agonists or antagonists.

In another aspect, synthetic libraries [Needels et al., *Proc. Natl. Acad. Sci. USA*, 90:10700–4 (1993); Ohlmeyer et al., *Proc. Natl. Acad. Sci. USA*, 90:10922–10926 (1993); Lam et al., International Patent Publication No. WO 92/00252; Kocis et al., International Patent Publication No. WO 9428028, each of which is incorporated herein by reference in its entirety], and the like can be used to screen for TRF ligands according to the present invention.

Screening can be performed with recombinant cells that express one or more TRFs of the present invention, or alternatively, using purified protein, and/or specific structural/functional domains of TRFs e.g., produced recombinantly, as described above. For example, a labelled TRF2 dimerization domain can be used to screen libraries, as described in the foregoing references for small molecules that will inhibit the dimerization of the TRF2. Similarly, antagonists or agonists to the acidic or basic domains of TRF1 and TRF2 respectively, can be identified in analogous screens. Indeed, essentially all of the nucleic acids, peptides and proteins, and antibodies can be employed in such drug assays.

In one such case, the activity of a specific TRF or fragment thereof (as disclosed herein) can be monitored or determined in the presence and absence of a potential drug. A candidate drug can then be selected on the basis of a measurable change in the activity determined, for example, which is found in the presence of the potential drug relative to in its absence. Such assays may be performed in vitro, in situ, and/or in vivo as desired.

Gene Therapy and Transgenic Vectors

In one embodiment, a gene encoding a TRF or structural/functional domain thereof is introduced in vivo in a viral vector. Such vectors include an attenuated or defective DNA virus, such as but not limited to herpes simplex virus (HSV), papilloma virus, Epstein Barr virus (EBV), adenovirus, adeno-associated virus (AAV), and the like. Defective viruses, which entirely or almost entirely lack viral genes, are preferred. Defective virus is not infective after introduction into a cell. Use of defective viral vectors allows for administration to cells in a specific, localized area, without concern that the vector can infect other cells. Thus, any tissue can be specifically targeted. Examples of particular vectors include, but are not limited to, a defective herpes virus 1 (HSV1) vector [Kaplitt et al., *Molec. Cell. Neurosci.*, 2:320–330 (1991)], an attenuated adenovirus vector, such as the vector described by Stratford-Perricaudet et al. [*J. Clin. Invest.*, 90:626–630 (1992)], and a defective adeno-associated virus vector [Samulski et al., *J. Virol.*, 61:3096–3101 (1987); Samulski et al., *J. Virol.*, 63:3822–3828 (1989)].

Preferably, for in vitro administration, an appropriate immunosuppressive treatment is employed in conjunction with the viral vector, e.g., adenovirus vector, to avoid immunodeactivation of the viral vector and transfected cells. For example, immunosuppressive cytokines, such as interleukin-12 (IL-12), interferon-γ(IFN-γ), or anti-CD4 antibody, can be administered to block humoral or cellular immune responses to the viral vectors [see, e.g., Wilson, *Nature Medicine* (1995)]. In addition, it is advantageous to employ a viral vector that is engineered to express a minimal number of antigens.

In another embodiment the gene can be introduced in a retroviral vector, e.g., as described in Anderson et al., U.S. Pat. No. 5,399,346; Mann et al., *Cell*, 33:153 (1983); Temin et al., U.S. Pat. No. 4,650,764; Temin et al., U.S. Pat. No. 4,980,289; Markowitz et al., *J. Virol.*, 62:1120 (1988); Temin et al., U.S. Pat. No. 5,124,263; International Patent Publication No. WO 95/07358, published Mar. 16, 1995, by Dougherty et al.; and Kuo et al., *Blood*, 82:845 (1993).

Targeted gene delivery is described in International Patent Publication WO 95/28494, published October 1995.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for in vivo transfection of a gene encoding a marker [Felgner et. al., *Proc. Natl. Acad. Sci. U.S.A.*, 84:7413–7417 (1987); see Mackey et al., *Proc. Natl. Acad. Sci U.S.A.*, 85:8027–8031 (1988)]. The use of cationic lipids may promote encapsulation of negatively charged nucleic acids, and also promote fusion with negatively charged cell membranes [Felgner and Ringold, *Science*, 337:387–388 (1989)]. The use of lipofection to introduce exogenous genes into the specific organs in vivo has certain practical advantages. Molecular targeting of liposomes to specific cells represents one area of benefit. It is clear that directing transfection to particular cell types would be particularly advantageous in a tissue with cellular heterogeneity, such as pancreas, liver, kidney, and the brain. Lipids may be chemically coupled to other molecules for the purpose of targeting [see Mackey et. al., supra]. Targeted peptides, e.g., hormones or neurotransmitters, and proteins such as antibodies, or non-peptide molecules could be coupled to liposomes chemically.

It is also possible to introduce the vector in vivo as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter [see, e.g., Wu et al.,*J. Biol. Chem.*, 267:963–967 (1992); Wu and Wu, *J. Biol. Chem.*, 263:14621–14624 (1988); Hartmut et al., Canadian Patent Application No. 2,012,311, filed Mar. 15, 1990].

In a preferred embodiment of the present invention, a gene therapy vector as described above employs a transcription control sequence operably associated with the sequence for the TRF inserted in the vector. That is, a specific expression vector of the present invention can be used in gene therapy.

Such an expression vector is particularly useful to regulate expression of a therapeutic TRF gene. In one embodiment, the present invention contemplates constitutive expression of the TRF gene, even if at low levels. Various therapeutic heterologous genes can be inserted in a gene therapy vector of the invention such as but not limited to adenosine deaminase (ADA) to treat severe combined immunodeficiency (SCID); marker genes or lymphokine genes into tumor infiltrating (TIL) T cells [Kasis et al.,*Proc. Natl. Acad. Sci. U.S.A.*, 87:473 (1990); Culver et al., ibid. 88:3155 (1991)]; genes for clotting factors such as Factor VIII and Factor IX for treating hemophilia [Dwarki et al., *Proc. Natl. Acad. Sci. USA*, 92:1023–1027 (1995); Thompson, *Thromb. and Haemostatis*, 66:119–122 (1991)]; and various other well known therapeutic genes such as, but not limited to, β-globin, dystrophin, insulin, erythropoietin, growth hormone, glucocerebrosidase, β-glucuronidase, α-antitrypsin, phenylalanine hydroxylase, tyrosine hydroxylase, ornithine transcarbamylase, apolipoproteins, and the like. In general, see U.S. Pat. No. 5,399,346 to Anderson et al.

Kits

In a further embodiment of this invention, commercial test kits suitable for use by a medical specialist may be prepared to determine the presence or absence of predetermined telomere-binding activity or predetermined telomere lengthening activity capability in suspected target cells. In accordance with the testing techniques discussed above, one class of such kits will contain at least the labelled TRF or its binding partner, for instance an antibody specific thereto, and directions, of course, depending upon the method selected, e.g., "competitive", "sandwich", "DASP" and the like. The kits may also contain peripheral reagents such as buffers, stabilizers, etc.

Accordingly, a test kit may be prepared for the demonstration of the presence or capability of cells for binding activity to telomeres, comprising:

(a) a predetermined amount of at least one labelled immunochemically reactive component obtained by the direct or indirect attachment of the present TRF or a specific binding partner thereto, to a detectable label;

(b) other reagents; and (c) directions for use of said kit.

More specifically, the diagnostic test kit may comprise:

(a) a known amount of the TRF as described above (or a binding partner) generally bound to a solid phase to form an immunosorbent, or in the alternative, bound to a suitable tag, or plural such end products, etc. (or their binding partners) one of each;

(b) if necessary, other reagents; and (c) directions for use of said test kit.

In a further variation, the test kit may be prepared and used for the purposes stated above, which operates according to a predetermined protocol (e.g. "competitive", "sandwich", "double antibody", etc.), and comprises:

(a) a labelled component which has been obtained by coupling the TRF to a detectable label;

(b) one or more additional immunochemical reagents of which at least one reagent is a ligand or an immobilized ligand, which ligand is selected from the group consisting of:

(i) a ligand capable of binding with the labelled component (a);

(ii) a ligand capable of binding with a binding partner of the labelled component (a);

(iii) a ligand capable of binding with at least one of the component(s) to be determined; and (iv) a ligand capable of binding with at least one of the binding partners of at least one of the component(s) to be determined; and (c) directing for the performance of a protocol for the detection and/or determination of one or more components of an immunochemical reaction between the TRF and a specific binding partner thereto.

In accordance with the above, an assay system for screening potential drugs effective to modulate the activity of the TRF may be prepared. The TRF may be introduced into a test system, and the prospective drug may also be introduced into the resulting cell culture, and the culture thereafter examined to observe any changes in the telomere lengths of chromosomes in the cells, due either to the addition of the prospective drug alone, or due to the effect of added quantities of the known TRF.

PRELIMINARY CONSIDERATION

Vertebrate telomeres contain 2–100 kb of tandem GGTTAG repeats. This telomeric nucleotide sequence is specified by the 5° CUAACC 3' template within the RNA component of vertebrate telomerases. Telomerase-mediated addition of GGTTAG repeats to the 3' chromosome ends can balance the loss of terminal sequences that occurs during replication of linear DNAs. The telomeric repeat array is essential for the stability of mammalian chromosomes. Without this protective cap, chromosome termini might activate DNA damage checkpoints, or be attacked by DNA repair functions leading to chromosome end fusion and degradation. This protective function of vertebrate telomeres is thought to result from the interaction of the telomeric GGTTAG repeats with telomere specific proteins. In support of this notion, telomeres in yeast and hypotrichous ciliates are known to contain protein components, telomeres have a unique chromatin structure [Tommerup et al., Mol. Cell Biol., 14:5777–5785 (1994)], and the sequence requirements for formation of new telomeres in human cells are highly specific [Hanish et al., Proc. Natl. Acad. Sci. USA, 91:8861–8865 (1994)], as would be expected if the GGTTAG repeats interact with a sequence specific DNA binding protein [de Lange, Seminars in Cell Biology 7, in press (1995)].

A search for telomeric proteins in vertebrate cells was therefore initiated. Since homologs of the telomeric proteins from unicellular organisms have not been found in vertebrates, biochemical approaches were taken to identify GGTTAG sequence specific DNA binding proteins. Several groups identified abundant proteins that interact with single-stranded GGTTAG repeats but these factors turned out to be hnRNP components that probably have a function in RNA metabolism rather than at telomeres [Ishikawa et al., Mol. Cell Biol., 13:4301–4310 (1993); McKay et al., Nucl. Acids Res., 20:1387–1391 (1992); McKay et al., Nucl. Acids Res., 20:6461–6464 (1992)].

The present invention uses double-stranded telomeric sequences to probe HeLa nuclear extracts for the presence of sequence-specific DNA binding proteins and has identified one candidate activity, called here Telomeric Repeat Binding Factor or TRF (Zhong et al., Mol. Cell Biol., 13:4834–4843 (1992), incorporated herein by reference in its entirety]. TRF was identified as a gel-shift activity that forms a specific complex with probes containing 3 or more tandem TTAGGG repeats. The sequence specificity of TRF is apparent from competition experiments in which the TRF gel-shift complex is easily competed out with TTAGGG repeat DNA but not with closely related telomeric sequences form other organisms, such as TTGGGG, and TTAGGC repeats. A TRF-like activity was found in all mammalian nuclear extracts that were examined, including extracts from a variety of human cell lines, human peripheral blood leukocytes, and extracts from monkey, mouse, hamster, and chicken cells [Zhong et al, (1992); unpublished observations by Chong and de Lange]. The sequence specificity of TRF and its ubiquitous expression were as expected for a vertebrate telomeric protein.

A series of molecular genetic experiments also suggested that TRF interacts with telomeric DNA in human cells [Hanish et al., Proc. Natl. Acad. Sci. USA, 91:8861–8865 (1994)]. In these experiments de novo formation of human telomeres was induced by transfection of telomeric repeat sequences into human cells. Upon transfection of 0.8 kb or more of TTAGGG repeat DNA into human HeLa cells, approximately 70% of the transfected cell lines will carry a new telomere. However, when stretches of TTGGGG repeats, TTAGGC repeats or other closely related sequences are transfected, telomere formation is not observed in any of the cell lines examined. These stringent sequence requirements for telomere formation in human cells closely follow the sequence preference of TRF [Hanish et al., (1994)]. No other factor that is currently known can explain this dependence on precise TTAGGG repeat in the process of de novo telomere formation. Therefore, it seems likely that the incoming TTAGGG repeats require the interaction with TRF to form a new telomere. This is as expected if TRF is an integral component of mammalian telomeres.

TRF1 is the first telomeric protein isolated from human, any other vertebrate cell, or any other multicellular organism. Uses for the TRF include those related to the involvement of telomeres in human cancer and aging. Human telomeres shorten during normal cell divisions and telomere shortening may eventually limit cell proliferation and lead to aging. In cancer cells, telomere shortening may lead to genome instability. Many human cancer cells contain the enzyme telomerase that can restore telomere length.

Inhibition of TRF in human tumors is expected to lead to loss of telomere function. This loss of telomere function could limit the growth of tumor cells. Inhibition of TRF could be achieved by anti-sense approaches. In addition, TRF inhibition could be used in combination with anti-telomerase therapy. Anti-telomerase drugs are presently being developed. However, such drugs may not have an acute cytotoxic phenotype because it takes some time to lose enough telomeric DNA after inhibition of telomerase. Dual inhibition of both TRF and telomerase may synergize the effects of either drug.

The presence of TRF on telomeres may be a good indicator of the function of human telomeres. Since telomeres change in length during tumorigenesis, TRF staining of chromosome ends in human tumors may be able to reveal aspects of the stage of the tumor. Moreover, loss of TRF function or changes in TRF function are predicted to destabilize the genome and may contribute to tumorigenic transformation. TRF may therefore be an oncogene. As such, TRF has diagnostic and therapeutic uses in cancer diagnosis and treatment. By analogy to the function of the telomeric protein RAP1 in yeast, TRF is expected to control telomere length. Therefore, TRF could be a target for therapies that aim to change telomere length. In addition, it is possible that mutations in TRF would be responsible for certain genome instability syndromes. In the cases of families with mutations in TRF, TRF could be useful for diagnostic purposes and also for gene therapy.

The present invention may be better understood by reference to the following non-limiting Examples, which are provided as exemplary of the invention. The following examples are presented in order to more fully illustrate the preferred embodiments of the invention. They should in no way be construed, however, as limiting the broad scope of the invention.

EXAMPLE 1

Purification of TRF Protein

TRF was isolated from nuclear extract from HeLa cells (see Zhong et al., 1992, for preparation of nuclear extract). The following general strategy was used:

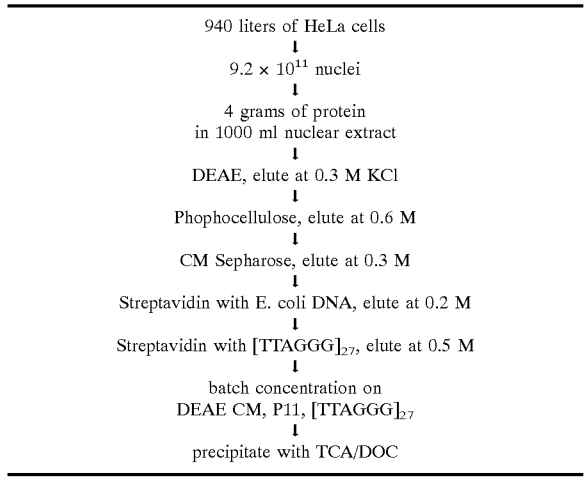

The use of a [TTAGGG]$_{27}$ repeat column greatly facilitated the purification of TRF. The column contains restriction fragments derived from a plasmid that was constructed by the present inventors, p[TTAGGG]$_{27 \times 6}$. This plasmid contains an tandem array of six restriction fragments that are identical and each carry 27 TTAGGG repeats. The plasmid is digested with Asp 718 restriction enzyme and the ends of the fragments are labelled with Bio-dUTP and coupled onto Sepharose-Streptavidin. This is the only column material which allowed the separation of TRF from other DNA binding proteins.

A significant finding was that TRF does not bind DNA when it is highly purified. Thus, during isolation of the protein all DNA binding activity disappears. It was discovered that the DNA binding activity could be rescued by adding back bovine b-casein and a select set of other proteins. The addition of casein to TRF preparations during the purification thus appeared to be a necessary element of the isolation.

Detailed Description of the Purification

TRF was isolated from a total of 9.2×10$^{11}$ HeLa Cells, equivalent to 940 liters of culture (in Joklik's Media, supplemented with bovine calf serum, 2 mM L-glutamine, 0.1 mM non-essential amino acids, and penicillin/streptomycin). A nuclear extract containing 4 grams of protein and about 650 pmol of TRF (1 pmol TRF is defined as the amount of protein required to complex 1 pmol of labelled probe), as determined by quantitation using a PhosphoImager, was obtained from the cells and the soluble fraction was then purified over a series of ion exchange and affinity columns, as noted above. For each column, the sample was loaded in buffer containing 100 mM KCI and the flow-through was reloaded. The columns were developed in buffer with increasing potassium chloride salt concentration, with a final stripping of the column with 1 M salt. All fractions were dialyzed to 100 mM KCl, 20 mM HEPES, 3 mM MgCl$_2$, 20% glycerol, and 0.1% NP-40 (nonidet-P40). Activity was determined by gel shift assay using a probe of 145 bp fragment containing (TTAGGG)$_{12}$ having the following sequence (SEQ ID NO:20):

5'-GTA CCC GGG GAT CGT GAC TCT AGA GGG GCC CTA ACC CTA ACC CTA ACC CTA ACC CTA ACC CTA ACC CTA ACC CTA ACC CTA ACC CTA ACC CTA ACC CTA ACC CGG GTC GAA TTC GAT CTC TAG AGT CGA CCT GCA GGC ATG C-3'

The nuclear extract was divided in half and the first 4 columns were run in duplicate. A 530 ml sample was applied onto a 200 ml DEAE column (diethenyl benzene, anion exchanger with 0.45–0.90 μm particle size, EM Separations) and TRF eluted at 0.2–0.3 M KCl. Fractions were collected in 100 ml aliquots. The active fractions were pooled (226 ml, 201 mg protein, 131 pmol TRF) and applied onto a 200 ml P11, phosphocellulose column (cation exchanger with fiber length 50–250 μm, Whatman). To activate the column the P11 resin was incubated in NaOH for 1 minute, HCl for 1 minute, then neutralized in HEPES, pH 7.9. TRF activity was found in 0.6 M fractions. These fractions were then combined (125 ml, 14 mg protein) and then run over a 4 ml CM Sepharose column (cross-linked agarose, 6%, cation exchanger, 45–165 μm). TRF eluted at 0.4–0.5 M KCl. The 4.5 ml of active fractions collected were run on a 4.5 ml non-specific DNA column. This column is composed of Biotin-labelled, Hinf I digested E. coli chromosomal DNA bound to streptavidin beads. TRF activity eluted at 0.2–0.3 mM KCl. At this point, the active fractions were combined from the duplicate purification schemes run in parallel and the rest of the purification was completed using 1 of each subsequent column. The affinity column is a biotin-labelled, Asp 718 digested DNA bound to streptavidin beads, with (TTAGGG)$_{27}$ plasmid DNA. A 4.5 ml sample was loaded onto a 0.5 ml affinity column and the activity eluted into 0.5 M KCl fractions. This fraction was supplied with casein (50 μg) and batch-wise bound to DEAE, CM, and P11 columns. The final fraction was bound to 100 μl of (TTAGGG)$_{27}$ column material and eluted at 0.5 M KCl. This active sample was precipitated with 20% trichloroacetic acid and 0.015% deoxycholate and then run on an SDS-PAGE gel and transferred to nitrocellulose. The 67 kD band was cut out, trypsinized, and sequenced.

EXAMPLE 2

Peptide Sequence Analysis and Isolation of TRF cDNAs

Approximately 3 micrograms TRF protein of a MW of 67 kD was isolated. The partial amino acid sequences of a number of TRF peptides was determined (FIG. 1). One of these sequences (T29) was used for a search of the databases and identified two anonymous human cDNA fragments present in the databases at that time. The Genbank accession number of these sequence are: Z19923 and Z45971.

Based on the nucleotide sequence of the anonymous cDNA fragment Z19923, a 33 nucleotide synthetic DNA probe was synthesized that overlaps the T29 peptide sequence. This probe was end-labelled and used to screen a commercial HeLa cDNA library (from Stratagene). The sequence of this probe is:

5' GTCAAAAACTGACATATGTATATCGTTCTCAAC 3' (SEQ ID NO:22)

From the screen of the HeLa cDNA library a candidate TRF cDNA was isolated (clone 11.2). The insert in this clone was subsequently used to rescreen the HeLa cDNA library. Sequence analysis of the longest human cDNAs resulted in the identification of an open reading frame that contained all peptide sequences previously identified.

The human TRF cDNA 4.1 was used to screen a Stratagene mouse cDNA library. One of the resulting clones, #12, was partially sequenced and showed a high degree of sequence similarity to the human cDNA. The MTRF12 cDNA contains an open reading frame that begins with an initiator codon that conforms to the Kozak rules, indicating that this is the N-terminus of the mouse TRF reading frame. That this clone indeed encodes full length mouse TRF proteins is further substantiated by the fact that TRF gel-shift complex encoded by this cDNA co-migrates with genuine mouse TRF from cultured J558 cells (see below).

The mouse and human sequences are very similar, allowing alignment of the two reading frames. The cDNA sequence of the human cDNA sequence and deduced open reading frame are given in FIGS. 2 and 3, respectively.

EXAMPLE 3

TRF Contains a Myb Type DNA Binding Domain

The TRF sequence was used to execute database searches and a similarity to Myb type DNA binding domains was noted (FIG. 4).

EXAMPLE 4

Proof That the cDNAs Encode TRF Activity

One of the human cDNAs (HTRF4.1) was used to construct a fusion protein in which part of the TRF open reading frame from the N-terminal Xho I site to the natural termination codon at the Hind III site was inserted into the pET28b His6Tag expression vector from Novagen (Madison, Wis.). This new, chimeric open reading frame contained an initiator ATG codon with "Kozak rules" environment at its 5' end as well as an T7 RNA polymerase promoter sequence upstream. This construct was used for in vitro coupled transcription/translation (using a kit from Promega) resulting in synthetic protein (labelled with $^{35}$S methionine) with an apparent molecular weight (MW) of 60 kD. The in vitro synthesized protein was used in a gel-shift assay with a double stranded (TTAGGG)$_{12}$ repeat probe and shown to form a complex that migrates close to the HeLa TRF gel-shift complex. The in vitro synthesized protein was shown to have the same sequence specificity as TRF; i.e., it bound to TTAGGG repeats but not to TTGGGG or TTAGGC repeats (FIG. 5).

Figure 6:
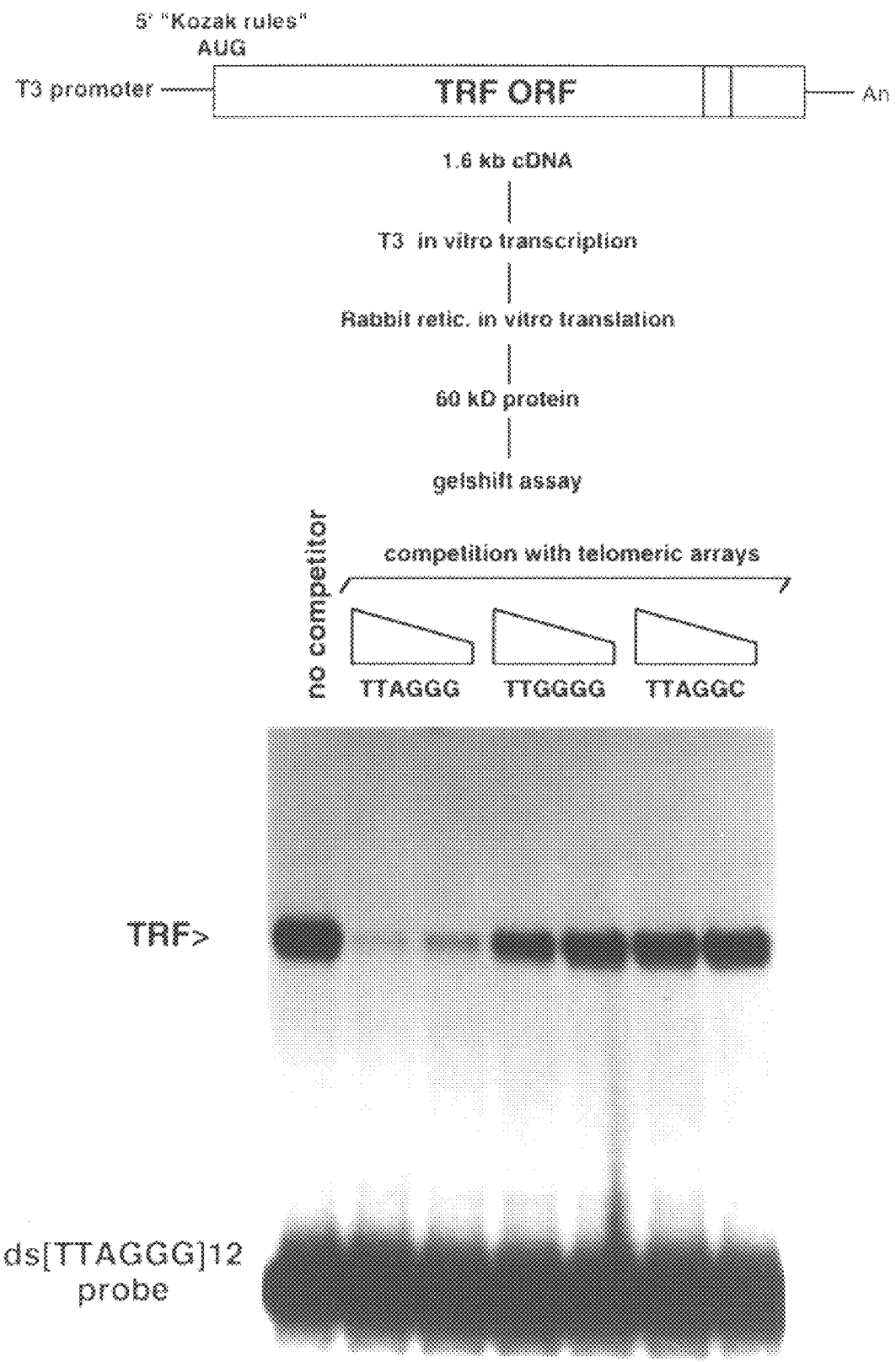
FIG. 6 depicts a gel-shift experiment showing telomeric repeat binding activity of protein encoded by the mouse MTRF12 cDNA. The cDNA was transcribed using T3 RNA polymerase and translated in a rabbit reticulocyte lysate. The probe is a $(TTAGGG)_{12}$-containing restriction fragment. Competitions were done with plasmids containing long arrays of telomeric DNAs with the indicated sequence. Gel-shift methods are as described by (Zhong et al, 1992).
Figure 7A:
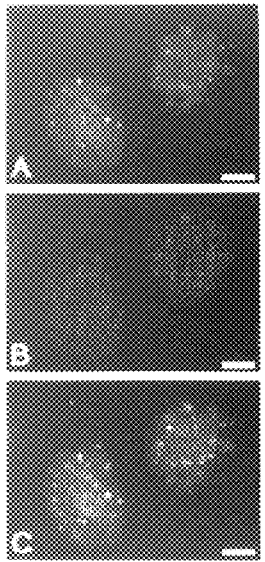
FIG. 7A shows a FLAG epitope tagged mouse TRF expressed in human HeLa cells. Shown is two interphase nuclei in which the anti-FLAG antibodies detect a speckled TRF pattern (green) against the background of DAPI stained DNA (blue).
Figure 7B:
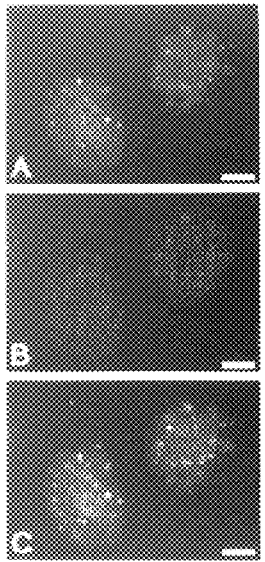
FIG. 7B shows in situ hybridization of telomeric TTAGGG DNA (red) in the nuclei shown in A.
Figure 7C:
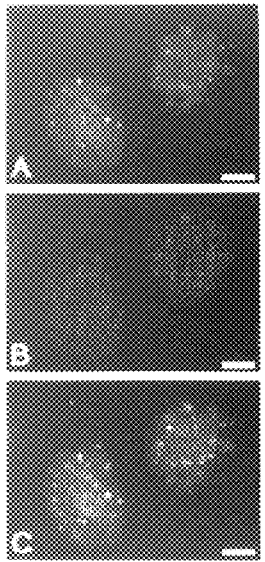
FIG. 7C shows superimposed images from FIGS. 7A and 7B, demonstrating that all signals co-localize.
Figure 7D:
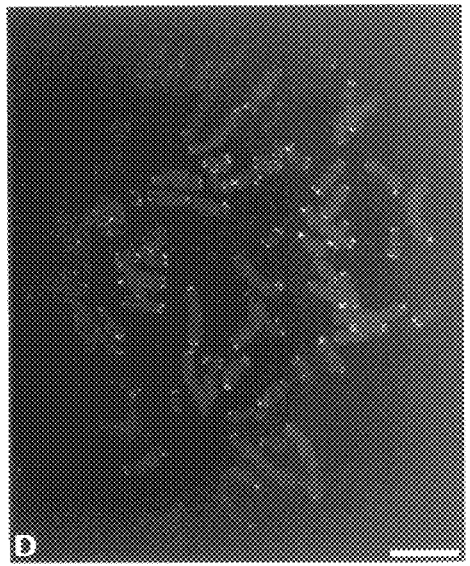
FIG. 7D shows HA epitope tagged mouse TRF expressed in human HeLa cells. Shown is a metaphase spread in which the anti-HA antibody detects TRF at each chromosome end (green). The DNA is stained with DAPI (blue).

The mouse cDNA (MTRF12) contained its own initiator codon and was transcribed and translated without further modification using the T3 promoter in its pBluescript vector. Similar to the human cDNA, a ~60 kD protein was synthesized that bound TTAGGG repeats but not TTGGGG or TTAGGC repeats (FIG. 6). The gel-shift complex obtained with MTRF-12 encoded protein co-migrates with the gel-shift complex formed with J558 mouse TRF, indicating that MTRF12 encodes full length TRF protein.

EXAMPLE 5

Proof That TRF is a Telomeric Protein
Staining of Metaphase Chromosome Ends

Using the mouse TRF cDNA (MTRF12), a gene was constructed encoding the TRF protein tagged at the N-terminus with the HA antibody tag. This gene was endowed with the cytomegalovirus promoter and a Bovine Growth Hormone poly A addition site and transfected into a HeLa cell line which had previously been shown to have long telomeres [de Lange, *EMBO J.*, 11:717–724 (1992); de Lange et al., *Mol. Cell Biol.*, 10:518–527 (1990)]. The construct also contained a neomycin marker gene, allowing selection of stably transfected HeLa cells in the presence of 300 μg/ml G418. Clonal cell lines that expressed the HA-tagged TRF were isolated and used to make metaphase chromosome spreads (using colcemid block and cytospin technique for spreading). Staining for the HA-tagged TRF was achieved using a monoclonal anti-HA antibody and a FITC labelled secondary goat anti-mouse antibody, Signals are noted at the ends of all metaphase chromosomes (FIG. 7). No other signals are seen. Control experiments with HeLa cells without the HA-TRF construct do not show telomeric staining.

EXAMPLE 6

Co-localization of TRF and Telomeric DNA in Interphase Nuclei

In a second line of evidence that TRF is exclusively located at telomeres it was shown that TTAGGG repeat DNA and epitope TRF co-localize in interphase cells. For these experiments MTRF12 was used to construct a FLAG tagged derivative fusion protein expressed from the CMV promoter.

This construct was transiently transfected (by electroporation) into HeLa cells with long telomeres (see preceding paragraph) and the cells were fixed 24 hours post-transfection with 2% formaldehyde. The telomeric DNA in these nuclei was detected through the annealing of a 150 nucleotide RNA containing CCCUAA repeats (the template is one of the TTAGGG repeat clones described in de Lange et al, 1990) that was synthesized in vitro in the presence of digoxygenin labelled rUTP and detected with sheep anti-digoxygenin primary antibody and a TRITC labelled donkey anti-sheep secondary antibody. The FLAG-tagged TRF was detected with a monoclonal mouse anti-FLAG antibody followed by a FITC labelled goat anti-mouse antibody. Both signals (TRITC and FITC) showed a speckled fully overlapping pattern, indicating complete co-localization of TRF with telomeric DNA (FIG. 7).

The following is a list of documents related to the above disclosure and particularly to the experimental procedures and discussions.

1. Tommerup, H., Dousmanis, A & de Lange, T., *Mol. Cell Biol.*, 14:5777–5785 (1994).
2. Hanish, J. P., Yanowitz, J. & de Lange, T., *Proc. Natl. Acad. Sci. USA*, 91:8861–8865 (1994).
3. de Lange, T., Seminars in *Cell Biology*, 7, in press (1996).
4. Ishikawa, F., Matunis, M. J., Dreyfuss, G & Cech, T. R., *Mol. Cell Biol.*, 13:4301–4310 (1993).
5. McKay, S. J. & Cooke, H., *Nucl. Acids Res.*, 20:1387–1391 (1992).
6. Mckay, S. J. & Cooke, H., *Nucl. Acids Res.*, 20:6461–6464 (1992).
7. Zhong, Z., Shiue, L., Kaplan, S. & de Lange, T., *Mol. Cell Biol.*, 13:4834–4843 (1992).
8. de Lange, T., *EMBO J.*, 11:717–724 (1992).
9. de Lange, T., Shiue, L., Myers, R. M., Cox, D. R., Naylor, S. L., Killery, A. M. & Varmus, H. E., *Mol. Cell Biol.*, 10:518–527 (1990).
10. de Lange, T., "Tolomore Dynamics and Gonomo Instability in Human Cancer," in Telomeres, Cold Spring Harbor Monograph, E. H. Blackburn and C. W. Greider, Eds (1995).
11. Broccoli, D., Young, J. W., de Lange, T., "Telomerase activity in normal and malignant hematopoietic cells," *Proc. Natl. Acad. Sci. USA*, in press (1995).

EXAMPLE 7

Human Telomeres Contain Two Distinct Myb-Related Proteins, TRF1 and TRF2

Introduction

Human telomeres are composed of long arrays of TTAGGG repeats that form a nucleoprotein complex required for the protection and replication of chromosome ends. One component of human telomeres is the TTAGGG repeat binding factor 1 (TRF1) disclosed above, a ubiquitously expressed, Myb-related protein present at telomeres throughout the cell cycle [Zhong et al, *Mol. Cell. Biol.*, 13:4834–4843 (1992); Chong et al., *Science*, 270:1663–1667 (1995); Ludérus et al., *J. Cell. Biol.*, 135:867–883 (1996); Broccoli et al., *Hum. Mol. Genetics*, 6:69–76 (1997); Smith et al., *Trends in Genetics*, 13:21–26 (1997); and Bianchi et al., supra, (1997)]. Recent evidence has implicates TRF1 in the control of telomere length [van Steensel, et al., *Nature*, 385:740–743 (1997)]. TRF1 is proposed to be an inhibitor of telomerase, acting in cis to limit the elongation of individual chromosome ends. The cloning of TRF2, a related homologue of TRF1 that carries a very similar Myb-type DNA binding motif is reported herein, Like TRF1, TRF2 is ubiquitously expressed, bound specifically to duplex TTAGGG repeats in vitro, and localized to all human telomeres in metaphase. TRF2 is shown to have a similar architecture to TRF1 in that it carries a C-terminal Myb motif and a large TR1-related dimerization domain near its N-terminus. However, the dimerization domains of TRF1 and TRF2 do not interact, suggesting that these proteins predominantly exist as homodimers. While having identical telomere binding activity and similar domain organization, TRF2 differs from TRF1 in that its N-terminus is basic rather than acidic, and TRF2 is much more conserved than TRF1. The results indicate that the TTAGGG repeat arrays at the ends of human and mouse chromosomes bind to two related proteins. Since TRF1 and TRF2 showed significant differences, suggesting that these factors have distinct functions at telomeres.

Methods

Cloning and Sequence Analysis.

The sequence of the 3' UTR of a TRF1-related EST (GenBank T58911) was used in a nested PCR strategy to clone a human TRF2 cDNA fragment from a HeLa cDNA library (Stratagene). Additional hTRF2 cDNAs were isolated by hybridization screening from a Namalwa [Scheidereit et al., *Nature*, 336:551–557 (1988)] and a breast cancer cell line [Kratzschmar et al., *J. Biol. Chem.*, 271:4593–4596 (1996)] library. The latter library yielded a cDNA that carried the complete open reading frame (designated hTRF2–16.1). This EDNA contains 1,282 bp of 3' UTR but appears to lack a canonical poly(A) addition sequence. The cDNA derived from HeLa cells and the hTRF2–16.1 cDNAs differed at amino acid position 433 where the HeLa cDNA encoded two alanine residues whereas the 16.1 cDNA encoded only a single alanine (FIG. 10A). A mouse cDNA (designated mTRF2–26) carrying the full open reading frame of mTRF2 was isolated from a mouse brain cDNA library (Stratagene) by hybridization to the human TRF2 cDNA.

Sequences were determined on both strands using duplex templates and have been deposited in the GenBank database. A comparison to the databases indicated that the TRF2 proteins are not homologous to previously identified proteins other than TRF1 and other Myb-related factors. Alignment of the TRF1 and 2 sequences was achieved using Clustalw 1.5 with a gap opening penalty of 20 and a gap extension penalty of 0.1 and the results were displayed using SeqVu 1.01.

Expression Studies.

mTRF2 containing an N-terminal FLAG epitope tag was constructed by cloning a NotI–ApaI fragment from mTRF2–26 representing the entire open reading frame into a modified pRc/CMV expression vector (Invitrogen) carrying the FLAG epitope 5' of the cloning site. The resulting construct contained 10 amino acids derived from the pBluescript polylinker and an additional 22 amino acids from the mTRF2 5' UTR as well as the mTRF2 start codon. FLAG-tagged mTRF2ΔN49 was constructed by PCR amplification of the region between amino acids 49 and the stop codon and cloning the purified PCR product into pRc/CMV. HeLa cells were transfected with the constructs by electroporation and processed for immunofluorescence of metaphase spreads or for simultaneous detection of telomeric DNA by FISH and mTRF2 by immunofluorescence as described previously [Chong et al., *Science*, 270:1663–1667 (1995); van Steensel et al., *Nature*, 385:740–743 ((1997)]. FLAG-tagged protein was detected with monoclonal antibody M2 (Kodak) followed by FITC-labelled donkey anti-mouse. For FISH, digoxigenin-labelled $[CCCUAA]_{27}$ RNA was detected with a sheep anti-digoxigenin antibody (Boehringer) and a TRITC-conjugated donkey anti-sheep IgG. Whole cell extracts were prepared from transfected cells in a buffer containing 400 mM KCl and 0.2% NP-40 as described [van Steensel et al., *Nature*, 385:740–743 (1997)] and used under standard conditions [Chong et al., *Science*, 270:1663–1667 (1995); van Steensel et al., *Nature*, 385:740–743 (1997)] in electrophoretic mobility shift assays for duplex [TTAGGG]$_{12}$ binding activity [Zhong et al., *Mol. Cell. Biol.*, 13:4834–4843 (1992)].

Yeast 2-hybrid Analysis.

Constructs for 2-hybrid analysis [Fields et al., *Nature*, 340:245–246 (1989)] containing the region between amino acid 45 and amino acid 246, representing the dimerization domain of hTRF2, were built by PCR-amplification and cloning into vectors pBTM116 [Bartel et al., Cellular interactions in development: a practical approach 9ed. Harley, D. A.) 153–179 IRL Perss, Oxford (1993)] and pACT2 (Clontech) to create GAD and LexA fusions respectively. The other constructs used as well as the procedures followed for yeast transformation and analysis of b-galactosidase activity were described previously [Bianchi et al., supra, (1997)].

Co-immunoprecipitation Experiments.

The human and mouse TRF1 constructs used were previously described [Chong et al., *Science*, 270:1663–1667 (1995); Broccoli et al., *Hum. Mol. Genetics*, 6:69–76 (1997); Bianchi et al., supra (1997)]. The FLAG-tagged mTRF2 and untagged mTRF2 were translated from cDNAs described above. $^{35}$S-methionine labelled proteins [Chong et al., *Science*, 270:1663–1667 (1995); Broccoli et al., *Hum. Mol. Genetics*, 6:69–76 (1997); Bianchi et al., supra, (1997)] were immunoprecipitated using the M2 anti-FLAG antibody in buffer D (20 mM Hepes-KOH pH 7.9, 100 mM KCl, 20% glycerol, 0.2 mM EDTA, 0.2 mM EGTA, 0.1% NP40, 0.1% Triton-X-100, 0.5 mM DTT, 0.5 mM PMSF) followed by four washes in buffer D with detergents and two washes in buffer D without detergent. Pellets were suspended in SDS/PAGE loading buffer and resolved on a 9% SDS-polyacrylamide gel.

Results

An anonymous cDNA fragment encoding a TRF1 related-Myb motif was reported in the database (GenBank T58911) [Bilaud et al., *Nucl. Acids Res.*, 24:1294–303 (1996)]. This sequence information was used in a combination of PCR and hybridization strategies to isolate the full length human and mouse cDNAs representing this protein (called TRF2 for TTAGGG repeat binding factor 2) (see Methods above). The human TRF2 (hTRF2) cDNA hybridized to a 3.1 kb mRNA with the same ubiquitous expression pattern as hTRF1 (FIG. 8A).

Figure 9B:
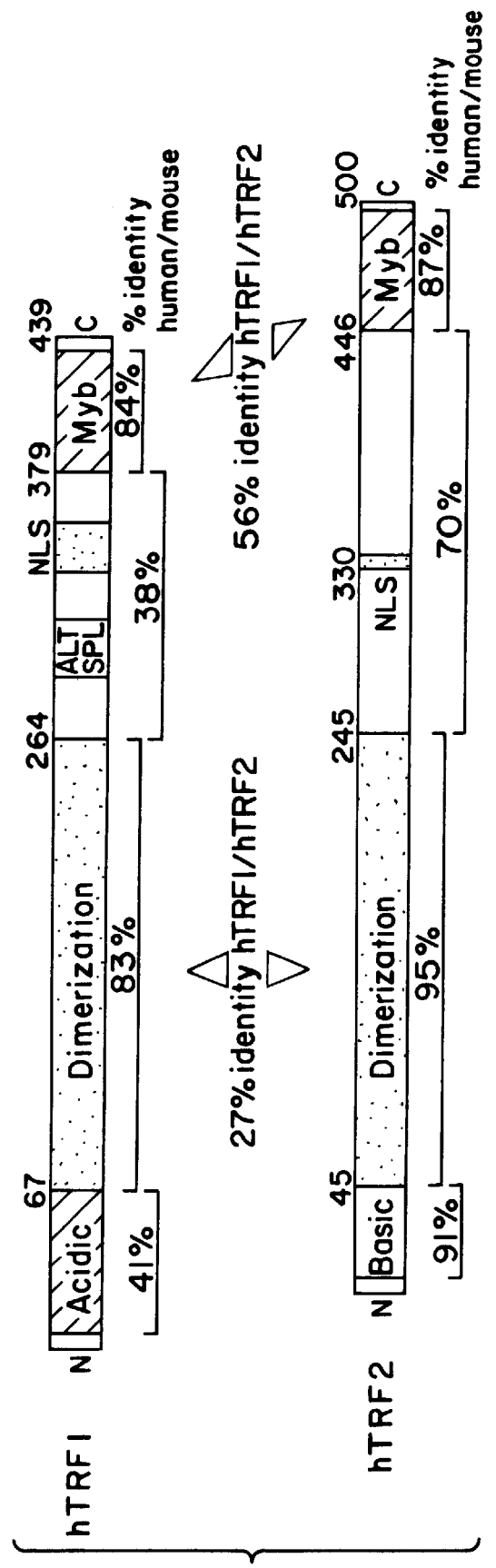
FIG. 9B is a schematic representation of the domain structure of hTRF1 and hTRF2 and their sequence similarity. The data on TRF1 is from Broccoli et al. [*Hum. Mol. Genetics* 6:69–76 (1997)] A small alternatively spliced exon (ALT SPL) is indicated in the hTRF1 sequence, The asterisk in c denotes an alanine residue that was found to be absent in one of the HeLa cDNAs sequenced.
Figure 11A:
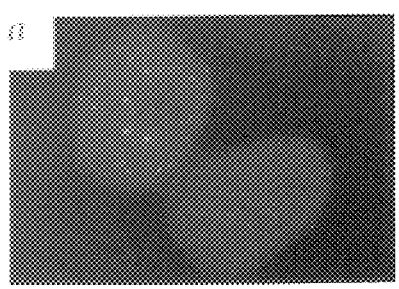
FIGS. 11A–11C show the co-localization of FLAG-epitope tagged mTRF2 protein with telomeric DNA in interphase.
Figure 11B:
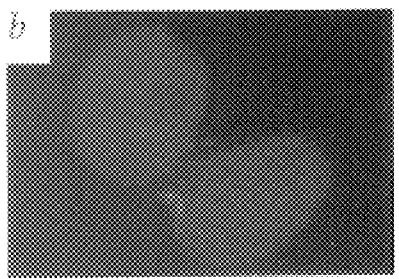
Figure 11C:
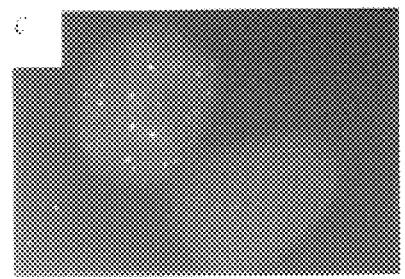
Figure 11D:
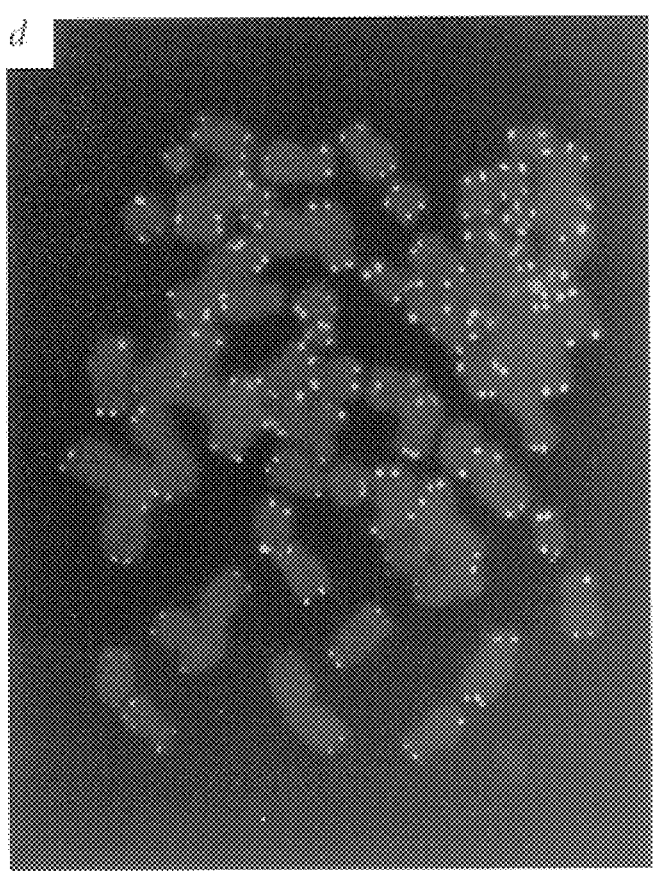
FIG. 11D shows the detection of mTRF2 at the ends of metaphase chromosomes with the M2 anti-FLAG antibody (green). DNA was stained with 4,6-diamidino-2-phenylindole (blue) in FIGS. 11A–11D.

Conceptual translation of the mouse and human TRF2 cDNAs revealed two open reading frames starting with Kozak consensus initiation sites that predicted two closely related proteins of approximately 500 amino acids. In agreement with the slightly longer primary sequence of TRF2, in vitro translated human and mouse TRF2 proteins displayed a larger apparent MW than human and mouse TRF1 (FIG. 8B). Alignment of the predicted sequences of TRF1 and TRF2 showed that the strongest conservation between these proteins is in their C-terminal Myb-domains (FIGS. 9A and 9B). In addition, a moderate level of conservation (27% identity) was observed in the region from positions 45 to 245 in hTRF2, coinciding with the previously identified dimerization domain of TRF1 [Bianchi et al., supra, (1997)] (FIG. 9B). Thus, TRF2 had a similar overall architecture as TRF1 with a C-terminal Myb-type DNA binding motif and a dimerization domain in the N-terminal half of the protein (FIG. 9B). However, a striking difference was that while both mouse and human TRF1 have an acidic amino terminus, TRF2 proteins contained predominantly basic residues in the N-terminus and the predicted pI of the two proteins is rather different (estimated to be 6.06 for hTRF1 and 9.11 for hTRF2). A second unexpected distinction was that TRF1 and 2 appeared to evolve at different rates. While TRF1 diverged rapidly leading to as little as 65% sequence identity between the human and mouse proteins [Broccoli et al., *Hum. Mol. Genetics*, 6:69–76 (1997)], TRF2 showed a much higher level of conservation (82% identity) more in keeping with the rate of divergence of other mammalian proteins (for which 85% identity is the norm [Makalowski et al., *Genome Res.*, 6:846–857 (1996)]) (FIG. 9B).

As TRF2 cared a Myb-type DNA binding domain with considerable sequence similarity to the TRF1 Myb motif, it was of interest to compare the DNA binding properties of these proteins. To address this issue, gel-shift assays were performed with extracts from HeLa cells transiently expressing mouse TRF2 (mTRF2) endowed with an N-terminal FLAG epitope (FIG. 10A). Using conditions previously optimized for the detection of TRF1 activity [Zhong et al., 1992, supra], a discrete DNA-protein complex that could represent mTRF2 bound to the duplex [TTAGGG]$_{12}$ probe was not observed. This effect is not due to co-migration of the hTRF1 and mTRF2 complexes because supershifting of the hTRF1 complex using a TRF1-specific anti-peptide antibody (antibody 5 [Ludérus et al., *J. Cell. Biol.*, 135:867–883 (1996)]) did not reveal a residual DNA binding activity that could represent TRF2 (FIG. 10A, lane 3). We also failed to detect a discrete TRF2 complex with a TRF2 protein lacking the FLAG-tag or when using a variety of other gel-shift systems. However, when the mTRF2-containing extracts were assayed in the presence of the anti-FLAG antibody, two discrete mTRF2-specific complexes were observed (FIG. 10A, lane 5). These supershifted complexes did not appear with extract from cells transfected with the vector backbone (FIG. 2a, lane 11). Possibly the binding of the FLAG antibody stabilized the mTRF2-DNA complex, altered its mobility in this gel-system, or removed an inhibitory activity such as interacting with the juxtaposed basic N-terminus and thereby preventing its potentially inhibiting effect, allows detection of the DNA binding activity of mTRF2.

Since the most striking difference between TRF2 and TRF1 is found in the charge of the N-terminus, it was determined if deletion of this part of TRF2 resulted in a detectable gel-shift complex. Transfection of deletion mutant mTRF2ΔN-49 into HeLa cells resulted in extracts with a readily detectable new TTAGGG repeat binding activity (FIG. 10B). This new activity was present in excess over the endogenous hTRF1 activity and could be supershifted with the FLAG antibody (FIG. 10B, lane 4). The mTRF2ΔN-49 mutant protein was also found to localize to telomeric loci in transfected cells (see below). The results suggested that TRF2 has the ability to bind to TTAGGG repeats in vitro but that its basic N-terminus somehow interfered with detection of a discrete TRF2-DNA complexes in this assay. These findings are in agreement with the previous demonstration by Bilaud et al. that a C-terminal fragment of hTRF2 can bind TTAGGG repeat DNA in a SouthWestern assay [Bilaud et al., *Nucl. Acids Res.*, 24:1294–303 (1996)].

In order to address the sequence specificity of TRF2, we assayed the [TTAGGG]$_{12}$ binding activity of mTRF2ΔN-49 in the presence of six different duplex telomeric DNAs (FIG. 10C). The competition experiments showed that the sequence preference of mTRF2ΔN-49 is indistinguishable from TRF1, both proteins binding much better to TTAGGG repeats than to TTAGGC, TTAGGGGG, and TAGGG repeats. Similar to TRF1 [Zhong et al., *Mol. Cell. Biol.*, 13:4834–4843 (1992); Hanish et al., *Proc. Natl. Acad. Sci. USA*, 91:8861–8865 (1994)], mTRF2DN-49 bound weakly to the TTGGGG repeats from Tetrahymena telomeres (FIG. 10C, lanes 5 and 6). As mTRF2 DN-49 binding is competed for by circular plasmids carrying TTAGGG repeat arrays (FIG. 10C), there is no in vitro requirement for a DNA end near the TRF2 binding site. Competition experiments also showed that, like TRF 1 [Zhong et al., *Mol. Cell. Biol.*, 13:4834–4843 (1992)], mTRF2 DN-49 failed to bind to single-stranded [TTAGGG]$_6$ and [CCCTAA]$_6$ oligonucleotides (FIG. 10C, lanes 15–18). These results are consistent with the high degree of sequence similarity of the Myb motifs in TRF1 and TRF2, and suggest that TRF2, like TRF1, could bind specifically to telomeric DNA in vivo.

To determine whether TRF2 is a component of the mammalian telomeric complex, full length FLAG-tagged mouse TRF2 was expressed in transiently-transfected HeLa cells. Indirect immunofluorescence with a monoclonals antibody to the FLAG epitope (M2) revealed a punctate pattern in interphase nuclei (FIG. 11A), as expected if the epitope-tagged mTRF2 protein specifically localized to telomeres. Labeling of the telomeres in the same nuclei by fluorescence in situ hybridization with a TTAGGG repeat specific RNA probe (FIG. 11B) revealed most telomeric loci coincided with an mTRF2 signal (FIG. 11C), indicative of a telomeric localization of the epitope-tagged protein. However, a minority of the mTRF2 signals was not obviously associated with telomeric DNA and some of the telomeric loci did not contain detectable mTRF2 (FIG. 11). Transfected mTRF2 was also demonstrable at the ends of mitotic chromosomes. All HeLa metaphase chromosomes were found to contain an mTRF2 signal at their termini (FIG. 11D) and no other location for the FLAG-tagged mTRF2 protein was noted. Similarly, FLAG-tagged mTRF2ΔN49 was found to localize to HeLa chromosome ends and the localization of epitope-tagged and GFP-tagged mTRF2 to telomeres in transfected NIH3T3 cells was observed. Thus, according to these indirect methods, TRF2 appears to be a integral component of the telomeric complex associated with telomeric DNA in interphase and mitosis. The telomeric localization of TUF2 was corroborated by detection of the endogenous TRF2 protein using a TRF2 specific antibody. TRF1 is a homodimer in solution and requires two Myb motifs to bind to telomeric DNA in vitro and in vivo [Bianchi et al., supra, (1997)]. Using the yeast 2-hybrid assay [Fields et al., Nature, 340:245–246 (1989)], the homodimerization domain of TRF1 was previously mapped to the region from position 66 to 263 [Bianchi et al., supra, (1997)] (see FIG. 12A). Since TRF2 displayed considerable sequence similarity to the dimerization domain of TRF1 (FIG. 9A), the dimerization domain of TRF2 was examined to see if it has the ability to interact with itself in the yeast 2-hybrid assay. Interaction of LexA and GAD fusion proteins bearing the TRF2 dimenzation domain resulted in readily detectable b-galactosidase activity in the same range as what is observed for TRF1—TRF1 interaction (FIG. 12A), suggesting that TRF2 has the ability to form homodimers with a similar architecture as TRF1. The similar migration rate of TRF1 and mTRF2ΔN-49 complexes in gel-shift assays (FIG. 10B) is consistent with both proteins binding to DNA as a dimer of approximately the same mass. Furthermore, addition of FLAG antibody to mTRF2ΔN-49 gelshifts resulted in two supershifted complexes (FIG. 10B), in agreement with the presence of two FLAG epitopes in each DNA bound TRF2 complex.

Figure 12A:
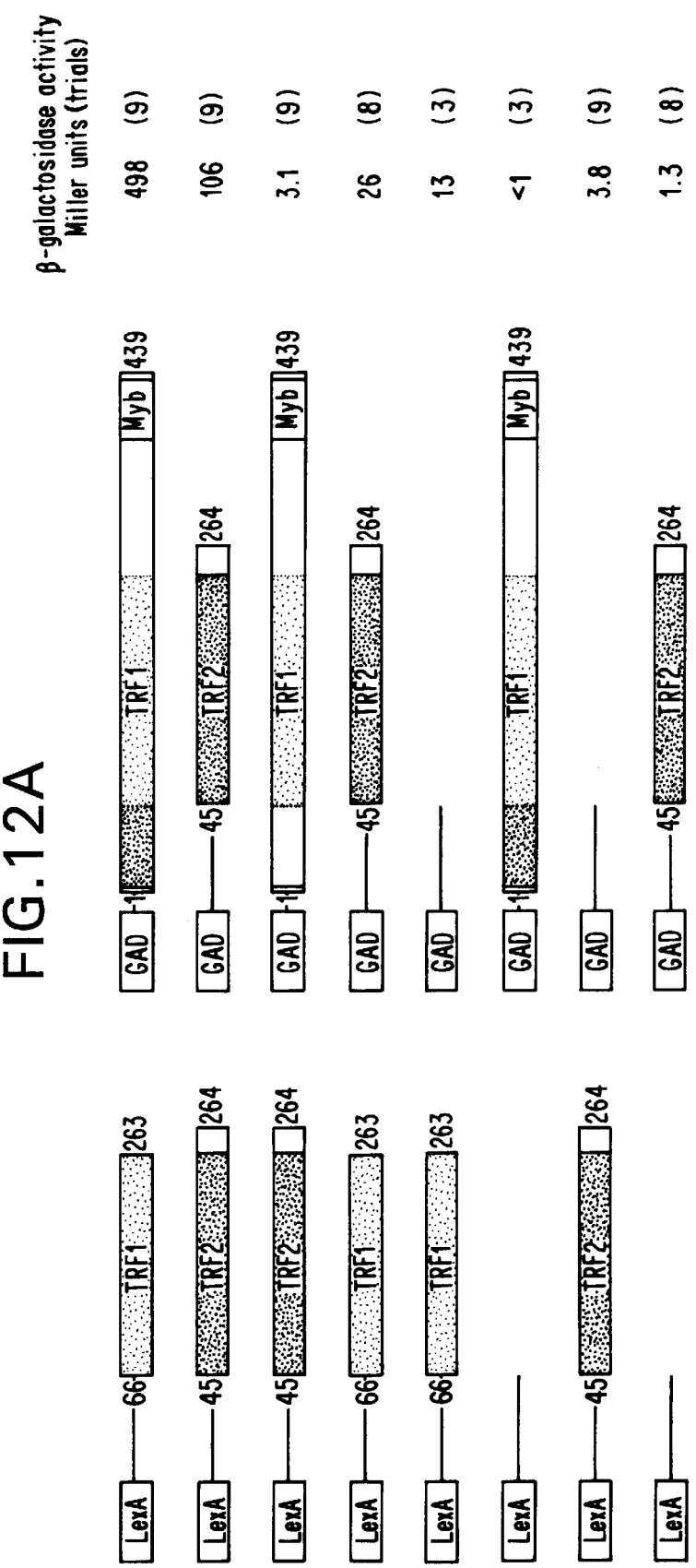
FIG. 12A shows the results from two hybrid assays [Fields et al., *Nature* 340:245–246 (1989)] for interactions between LexA and GAD fusion proteins containing the indicated portions of hTRF1 and hTRF2 constructed as described previously [Bianchi et al., 1997, supra]. β-galactosidase activity levels were measured as described previously [Bianchi et al., 1997, supra] for strains containing the indicated plasmids. Values represent an average of three to nine independent transformants.

Next the yeast 2-hybrid assay was used to determine whether the dimerization domains of TRF1 and TRF2 can interact. In a large number of trials, no convincing interactions between these proteins in two settings were detected (FIG. 12A). No activation occurred when the dimerization domain of TRF2 was probed for interactions with full length TRF1. In addition, no significant interactions were observed between fusion proteins containing the isolated TRF1 and TRF2 dimerization domains. The weak b-galactosidase activity detected with these proteins is probably due to the inherent slight transactivation activity of the TRF1 dimerization domain (FIG. 12A) which has been noted previously [Bianchi et al., supra, (1997)].

These data indicated that while TRF2 has the ability to interact with itself, the TRF1-TRF2 interaction was either absent or much weaker. Absence of heterodimer formation was further corroborated by co-immunoprecipitation of in vitro translation products (FIG. 12B). In these experiments, FLAG-hTRF1 (human TRF) could he immunoprecipitated together with GFP-hTRF1 and FLAG-mTRF2 (mouse TRF) was found to associate with an untagged version of mTRF2, consistent with homodimerization by both proteins. However, FLAG-mTRF1 (mouse TRF) failed to form a stable association with mTRF2 (FIG. 12B). The lack of heterodimerization is also consistent with the gel-shift assays on extracts from cells over-expressing mTRF2ΔN-49 (FIG. 10B). In these experiments, expression of an excess of mTRF2ΔN-49 did not reduce the presence of hTRF1 homodimer in the extract, indicating that mTRF2ΔN-49 did not form heterodimers with hTRF1. The unaltered level of the TRF1 gel-shift complex was most clearly demonstrated in reactions in which the mTRF2ΔN-49 complex was supershifted with the FLAG antibody (FIG. 10B, lane 4). In similar experiments executed with FLAG-tagged hTRF1, heterodimerization between the endogenous TRF1 and the transfected protein is consistently detected.

These results demonstrate that human telomeres contain two distinct distantly-related telomeric DNA binding proteins, TRF1 and TRF2. TRF1 and TRF2 have several features in common. They both carry a C-terminal Myb-type DNA binding domain and have the ability to form homodimers through interactions in an N-terminal dimerization domain. Both proteins show specificity for the duplex TTAGGG repeats typical of vertebrate telomeres and they have the same expression pattern. However, TRF1 and TRF2 are clearly distinguishable based on the difference in the amino acid composition of their N-terminus and their rates of evolution, suggesting that these two factors may have distinct functions, in the regulation of telomere regulation.

Unlike the situation in human cells, in the yeast S. cerevisiae, the duplex part of the telomere is bound to a single DNA binding protein, Rap1p. While Rap1p is structurally and functionally similar to TRF1 [Smith et al., Trends in Genetics, 13:21–26 (1997); van Steensel et al., Nature, 385:740–743 (1997); Kyrlon et al., Mol. Cell. Biol., 12:5159–5173 (1992); Konig et al., Cell, 85:125–136 (1996); Marcand et al., Science, 275:986–990 (1997)], these two proteins show little or no amino acid sequence similarity. Recent data suggest that Rap1p bound to telomeres exists in two alternative states, one associated with the Sir proteins and another complexed with Rif proteins (ref. [Marcand et al., Science, 275:986–990 (1997)]). The two forms of Rap1p are proposed to have different functions at telomeres. The presence of two distinct telomeric proteins on human telomeres could similarly reflect two different asks for duplex telomeric binding factors

EXAMPLE 8

TRF2 PROTECTS HUMAN TELOMERES FROM END TO END FUSIONS

Introduction

Based on genetic and cytological observations Muller and McClintock reasoned that telomeres protect chromosomes from end-to-end fusion [Muller, The Collecting Net-Woods Hole, 13:181–195 (1938); McClintock, Genetics, 26:234–282 (1941); McClintock, Proc. Natl. Acad. Sci. USA, 28:458–463 (1942)]. Telomeres are now understood to be terminal complexes of repetitive sequences and associated proteins that distinguish natural chromosome ends from damaged DNA. Despite their extensive characterization in yeasts, ciliates, and mammals, the molecular mechanism by which telomeres prevent end-to-end fusions has heretofore been unclear. This issue is studied herein in human cells by direct visualization of chromosome behavior after interference with the function of a telomeric protein.

Human chromosome ends carry 2–30 kb of double-stranded TTAGGG repeats, which are necessary and sufficient for telomere function in somatic cells [Farr et al., Proc. Natl. Acad. Sci. USA, 88:7006–7010 (1991); Hanish et al., Proc. Natl. Acad. Sci. USA, 91:8861–8865 (1994)]. In the germline and in immortalized cells, this sequence can be maintained by telomerase, a reverse transcriptase that adds TTAGGG repeats onto the 3' ends of chromosomes (see [Morin, Seminars in Cell Dev. Biol., 7:5–15 (1996)] for review). The termini of human telomeres carry long (~150 nt) protrusions of single-stranded TTAGGG repeats [Makarov et al., Cell, 88:657–666 (1997); McElligott and Wellinger, EMBO J, 16:3705–3714 (1997); Wright et al., Genes Dev., 11:2801 (1997)], which are an effective substrate for telomerase in vitro. According to one analysis [Makarov et al., Cell, 88:657–666 (1997)], G-strand overhangs appear to be present at most chromosome ends and are maintained in cells lacking telomerase, suggesting that a 5'-3' exonuclease acting on the C-rich telomeric strand may be responsible for their formation. However, other experiments suggest that long G-strand tails are only present on half of the chromosome ends, consistent with their being generated by incomplete lagging strand synthesis during DNA replication [Wright et al., Genes Dev., 11:2801 (1997)].

Telomeres in somatic human cells shorten by 50–200 bp per cell division [Cooke and Smith, Cold Spring Harbor Symp. Quant. Biol., LI:213–219 (1986); Harley et al., Nature, 345:458–460 (1990); Hastie et al., Nature, 346:866–868 (1990); reviewed in Harley et al., In Telomeres, Cold Spring Harbor Press, Cold Spring Harbor, N.Y. (1995)]. Programmed telomere shortening in normal human cells may function as a tumor suppresser mechanism that limits the growth potential of transformed cells [reviewed in de Lange, In Telomeres, Cold Spring Harbor Press, Cold Spring Harbor, N.Y. (1995)]. In agreement, telomere length is strongly correlated with the proliferative capacity of normal human cell; and the catalytic subunit of telomerase (hTRT/hEst2p) is upregulated in human tumors and immortalized cells [Allsopp et al., Proc. Natl. Acad. Sci. USA, 89:10114–10118 (1992); Meyerson et al., Cell, 90:785–795 (1997); Nakamura et al., Science, 277:955–959 (1997)].

Loss of telomere function in human cells results in the formation of dicentric chromosomes and other abnormalities created through end-to-end fusions [Counter et al., EMBO J., 11:1921–1929 (1992)]. Both in senescent cells and in tumor cells, dicentric chromosomes, rings, and sister-chromatid fusions are correlated with critically shortened telomeres [reviewed in de Lange, In Telomeres, Cold Spring Harbor Press, Cold Spring Harbor (1995)]. These observations, taken together with evidence for a protective role of telomeres from yeast, ciliates, flies, and maize, have led to the supposition that chromosome ends lacking telomeric DNA fail to recruit a terminal protein complex required for their protection. However, there has been no direct evidence for telomeric proteins that protect chromosome ends from end-to-end fusion and it has remained obscure how such factors might act.

Two human telomeric DNA binding proteins are identified herein. TRF1 was isolated as a double-stranded TTAGGG repeat binding protein from HeLa cells. This factor is a homodimeric protein with a C-terminal helix-turn helix motif similar to the Myb and homeodomain DNA binding folds [Bianchi et al., EMBO J., 16:1785–1794 (1997)] [reviewed in Smith and de Lange, Trends in Genetics, 13:21–26 (1997); and Konig and Rhodes, Trends Biochem. Sci., 22:43–47 (1997)]. TRF2 carries a similar C-terminal Myb motif but is different from TRF1 in that its N-terminus is very basic rather than acidic [Bilaud et al., Nature Genetics, 17:236–239 (1997); Broccoli et al., Nature Gen., 17:231–235 (1997)] FIG. 13A). Both proteins bind specifically to double-stranded TTAGGG repeats in vitro and are located at telomeres in vivo. The two TRFs are ubiquitously expressed and current evidence is consistent with most human telomeres containing both factors bound simultaneously throughout the cell cycle [Chong et al., Science, 270:1663–1667 (1995); Broccoli et al., Nature Gen., 17:231–235 (1997); Smith and de Lange, Trends in Genetics, 13:21–26 (1997); van Steensel and de Lange, Nature, 385:740–743; U.S. patent application Ser. No. 08/800,264 filed Feb. 13, 1997, hereby incorporated herein by reference it its entirety]. TRF1 has been shown to be a negative regulator of telomere length maintenance [van Steensel and de Lange, Nature, 385:740–473; U.S. patent application Ser. No. 08/800,264 filed Feb. 13, 1997]. Here a key role for TRF2 is demonstrated for a second function of telomeres, the protection of chromosome ends from end-to-end fusion.

Experimental Procedures

Expression Vectors.

The cDNA encoding full-length human TRF2 was placed under the tetracyclin-controlled promoter by cloning the EcoRI fragment of plasmid phTRF216-1 [Broccoli et al., 1997; Example 7] into vector pUHD10-3, resulting in plasmid pTethTRF2. To facilitate the creation of constructs encoding truncated proteins with an N-terminal FLAG-tag, expression vector pTetNFLAG was constructed by inserting a linker encoding a FLAG tag and an EcoRI site into the SacII and BamHI sites of pUHD10-3. Next, TRF2$^{\Delta B}$ (containing amino acids 45–500 of SEQ ID NO:27) and TRF2$^{\Delta B\Delta M}$ (containing amino acids 45–454 of SEQ ID NO:27) were each cloned into the EcoRI and BamHI sites of pTetNFLAG (in-frame with the FLAG-tag) by PCR cloning, using Pfu-polymerase, plasmid phTRF216-1 as template, with 5'TTGAATTCGAGGCACGGCTGGAAGAG3' (SEQ ID NO:51) as forward primer for both constructs, 5'CGG-GATCCTGTTTCAGTTCATGCCAA3' (SEQ ID NO:51) as backward primer for TRF2$^{45-500}$ and 5'CGGGATCCTCAT-TCTACAGTCCACTTCTGCT3' (SEQ ID NO:52) as backward primer for TRF2$^{45-454}$.

Induction of TRF2 Polypeptides in HTC75 Cells.

The empty vector pUHD 10-3 and the pUHD10-3-derived constructs for expression of the TRF2 alleles were each co-transfected with neomycin resistance plasmid pNY-HI into cell line HTC75 using the calcium phosphate co-precipitation. HTC75 is a hygromycin resistant HT1080-derived clonal cell line that stably expresses the tetracyclin-controlled transactivator (tTA) [Gossen and Bujard, Proc. Natl. Acad. Sci. USA, 89:5547–5551 (1992); van Steensel and de Lange, Nature, 385:740–743 (1997); U.S. patent application Ser. No. 08/800,264 filed Feb. 13, 1997]. Transfected cells were grown in the presence of doxycyclin (100 ng/ml) and G418 (600 µg/ml). For each construct approximately 25 G418-resistant cell lines were isolated by ring cloning and tested for expression of TRF2 polypeptides after 24 hours of induction. Expression of TRF2$^{\Delta B\Delta M}$ and TRF2$^{\Delta B}$ was tested by immunofluorescence microscopy and western blotting using anti-FLAG antibody M2 (Eastman Kodak); expression of wild-type TRF2 was tested by gel-shift assays using a TTAGGG repeat probe and by western blotting using affinity-purified serum #508 (see below). All clones were grown in DMEM supplemented with 10% bovine calf serum or bovine fetal serum and 150 µg G418 per ml. All clones were grown in parallel with or without doxycyclin (100 ng/ml).

Polyclonal Antibody Against TRF2.

A 28-mer peptide (pep28) encompassing amino acid residues 16–42 of human TRF2 (SEQ ID NO:27) with an additional N-terminal cysteine was synthesized (BioSynthesis, Lewisville, Tex.) and conjugated to maleimide-activated Keyhole Limpet Haemocyanin (KLH, Pierce, Rockford, Ill.). Serum from a rabbit immunized with the pep28-KLH conjugate was affinity-purified against pep28 cross-linked to SulfoLink coupling gel (Pierce) using standard procedures [Harlow and Lane, Antibodies, a laboratory manual, Cold Spring Harbor Press (1988)]. The resulting purified antibody #508 reacts specifically with TRF2 in western blotting and immunofluorescence labeling assays. The antibody does not cross-react with TRF1.

Whole-cell Extracts.

Cells grown in 10 cm dishes were washed with 5 ml cold phosphate buffered saline (PBS), harvested by scraping in 1 ml PBS per dish and centrifuged 2 minutes in an Eppendorf microfuge at setting 4,000 g. Subsequent steps were all carried out on ice or at 4° C. The cell pellets (~4 million cells) were resuspended in 200 µl buffer C (20 mM Hepes-KOH pH 7.9, 420 mM KCl 25% glycerol, 0.1 mM EDTA, 5 mM MgCl$_2$, 1 mM dithiothreitol, 0.5 mM phenylmethyl-sulfonyl fluoride, 0.2% Nonidet P-40, 1 µg leupeptin per ml, 1 μg pepstatin per ml, 1 μg aprotinin per ml), incubated for 30 minutes and centrifuged for 10 minutes in an Eppendorf microfuge at 14,000 g. The supernatant was dialyzed 2–5 hrs against 100 ml of buffer D (20 mM Hepes-KOH pH 7.9, 100 mM KCl, 20% glycerol, 0.2 mM EDTA, 0.2 mM EGTA, 0.5 mM dithiothreitol, 0.5 mM phenylmethylsulfonyl fluoride), frozen in liquid nitrogen and stored at −80° C. Protein content of the extracts was measured using the Bradford assay (BioRad, Hercules, Calif.) using bovine serum albumin as a standard.

Western Blotting.

Twenty μg of whole-cell extract proteins were separated on 10% SDS-polyacrylamide gels and transferred to nitrocellulose by electroblotting. Ponceau S staining confirmed equal loading of the samples. Blots were pre-incubated 30 minutes in 10% non-fat milk powder and 0.5% Tween-20 in PBS. All subsequent incubations and washing steps were carried out in 0.1% non-fat dry milk powder and 0.1% (w/v) Tween-20 in PBS. Blots were incubated for 12–16 hours at 4° C. with either anti-FLAG antibody M2 or anti-TRF2 antibody #508, followed by three 10 minute washing steps. Next, blots were incubated 45 minutes with horseradish peroxidase conjugated sheep-anti-mouse (Jackson Immnuno Research Labs) or donkey-anti-rabbit antibody (Amersham) and washed three times for 10 minutes. Bound antibody was detected using the ECL kit (Amersham).

Immunofluorescence Labeling and Microscopy.

The HeLaI.2.11 cell line, a subclone of HeLaI [Saltman et al., Chromosoma, 102:121–128 (1993)] bearing telomeres of >25 kb, was transfected by electroporation with pTethTRF2, pTetFLAGhTRF2$^{\Delta B}$, or pTetFLAGhTRF2$^{\Delta B \Delta M}$ together with the tTA-expression vector pUHD15-1 [Gossen and Bujard, Proc. Natl. Acad. Sci. USA, 89:5547–5551 (1992)]. Cells were grown for 24 hours on Alcian Blue coated coverslips in the absence of doxycyclin. Fixation and immunostaining were carried out as described [Chong et al., Science, 270:1663–1667 (1995); van Steensel and de Lange, Nature, 385:740–743 (1997); U.S. patent application Ser. No. 08/800,264 filed Feb. 13, 1997]. TRF2 was detected with polyclonal antibody #508 (see above) raised and affinity purified against an N-terminal peptide of TRF2. The FLAG epitope tag was detected with the M2 anti-FLAG monoclonal antibody (Eastman Kodak). TRF1 was detected with a mouse polyclonal serum (#2) directed against the full length protein or with antibody 371C2. Rabbit antibodies were detected with FITC- or Cy3-conjugated donkey-anti-rabbit antibodies (Jackson ImmunoResearch Labs). Mouse antibodies were detected with FITC-conjugated donkey-anti-mouse antibody (Jackson ImmunoResearch Labs). Control experiments indicated that secondary antibodies did not show any cross-reaction. To exclude that binding of anti-TRF1 (#371C2, [van Steensel and de Lange, Nature, 385:740–743 (1997); U.S. patent application Ser. No. 08/800,264 filed Feb. 13, 1997]) and anti-TRF2 (#508) antibodies to endogenous TRF proteins was prevented by anti-FLAG antibody M2 through steric hindrance, the cells were pre-inducated overnight with #371C2 or #508 before adding M2.

Micrographs were recorded on a Zeiss Axioplan microscope with a Kodak DCS200 digital camera. Images were noise-filtered, corrected for background and merged using Adobe Photoshop.

Cell Growth Curves and β-galactosidase Assay.

Cells were plated in duplicate at various densities (~0.1–4.0×10$^6$ cells/15 cm dish) the day before the experiment. On day 0, all plates were washed three times with medium containing G418 (150 μg/ml), with or without doxycyclin (100 ng/ml). On indicated days cells were harvested and counted, and cell pellets were frozen at −80° C. for isolation of genomic DNA. Whole-cell extracts were prepared from dishes grown in parallel. In most experiments, cells were split at day 4 (1:32–1:4) for day 6 and day 9 time points.

Cells induced for 9 days were stained for β-galactosidase using the method described in Dimri et al. [Proc. Natl. Acad. Sci. USA, 92:9363–9367 (1995)], but with phosphate buffer instead of citrate/phosphate buffer. Cells were washed in PBS, pH 7.2, fixed for 5 minutes in 2% formaldehyde/0.2% glutaraldehyde solution in PBS, washed again in PBS (pH 7.2) and stained with X-gal (1 mg/ml) in 150 mM NaCl, 2 MM MgCl$_2$, 5 mM K$_3$Fe(CN)$_6$, 5 mM K$_4$Fe(CN)$_6$, and 40 mM NaPi pH 6.0, pH 4.0 or pH 7.0, for 6 to 12 hours at 37° C.

Chromosome Analysis in Metaphase and Anaphase Cells.

Four to six days after induction (as indicated in the text) cells were incubated with 0.1 μg demecolcine per ml for 90 minutes, harvested by trypsinization, incubated for 7 minutes at 37° C. in 0.075 M KCl, and fixed in freshly prepared methanol: glacial acidic acid (3:1 vol/vol). Cells were stored at 4° C. and when needed dropped onto wet slides and air dried.

For DAPI staining of DNA, slides with metaphase spreads were incubated 10 minutes in 0.5 μg 4', 6-diamino-2-phenylindole (DAPI)(Sigma) per ml PBS, washed for 2 minutes in PBS, and mounted in 90% glycerol/10% PBS containing 1 mg p-phenylene diamine (Sigma)/ml.

For trypsin banding, metaphase spreads prepared as above were incubated in banding solution (2×trypsin-EDTA (Gibco), 1×Hanks Balanced Salt Solution(Gibco) in water) for 45 to 75 seconds at 37° C. and stained with filtered staining solution (16% Giemsa Blood Staining Solution (J. T.Baker), 4% Giemsa Solution (Fisher) in Tris-Maleic acid buffer pH 5.6) for 60–75 seconds at room temperature.

Anaphase cells were visualized by DAPI staining of cells grown on cover slips for the indicated number of days in the presence or absence of doxycyclin.

FISH.

In situ hybridization was executed according to Lansdorp et al. [Hum. Mol. Gen., 5:685–691 (1996)]. Hybridization was performed with 0.5 μg/ml FITC-conjugated($C_3TA_2$)$_3$ peptide nucleic acid (PNA) probe (Biotech GmbH), and after washing, the cells were embedded in 90% glycerol10% PBS containing 1 mg p-phenylene diamine (Sigma Chemical Company, Inc.) per ml, supplemented with 0.2 μg 4',6-diamino-2-phenylindole (DAPI) per ml.

Genomic Blotting and Bal31 Digestion.

Isolation of genomic DNA, genomic blotting and telomere-length estimation were carried out as described [van Steensel and de Lange, Nature, 385:740–743 (1997); U.S. patent application Ser. No. 08/800,264 filed Feb. 13, 1997]. For the Bal31 nuclease experiment, about 65 μg undigested genomic DNA was incubated at 30° C. with 13 units Bal31 nuclease (mixed, New England Biolabs, Beverly, Mass.) in 390 μl buffer containing 600 mM NaCl, 12 mM CaCl$_2$, 12 mM MgCl$_2$, 20 mM Tris-HCl, 1 mM EDTA, pH 8.0. At indicated time points, 30 μl samples were taken and inactivated by addition of 2 μl 0.5 M EGTA and incubation for 10 minutes at 65° C. Bal31 treated DNA samples were extracted with phenol/chloroform, precipitated with ethanol and digested with HinfI and RsaI. To ensure equal loading on agarose gels, all DNA samples were quantified after restriction enzyme digestion by fluorometry using Hoechst 33258 dye.

G-strand Overhang Assay.

The non-denaturing hybridization assay to detect G-strand overhangs was carried out essentially as described [Makarov et al., Cell, 88:657–666 (1997)]. [TTAGGG]$_4$ and [CCCTAA]$_4$ oligonucleotide probes were end-labelled using $\gamma$-$^{32}$P-ATP (3000 Ci/mmol, Amersham) and T4 polynucleotide kinase. Depending on the experiment, 2.5–5.0 μg HinfI/RsaI digested genomic DNA was ethanol-precipitated, resuspended in 21 μl hybridization buffer (50 mM Tris-HCl pH 8.0, 50 mM NaCl, 1 mM EDTA), added to 4 μl labelled probe (8 nM) and incubated 10–16 hrs at 50° C. in a Perkin-Elmer PCR-thermocycler. Hybridized samples were size-fractionated on 0.8% agarose gels in 1×TAE. The gels were dried on Whatman DE-81 filterpaper and exposed to autoradiography film or a Phosphorimager screen. As a control, 4 μg HinfI/RsaI digested DNA was treated for 30 minutes at 30° C. with 0, 10 or 40 Units Mung Bean nuclease (New England Biolabs) in MB buffer (50 mM sodium acetate, 30 mM NaCl, 1 mM ZnSO4, pH 5.0), inactivated by addition of 0.01% SDS, and ethanol-precipitated before carrying out the overhang assay. Inspection of the ethidium bromide stained gel confirmed that Mung Bean nuclease did not have any detectable endonuclease activity. Treatment with 40 U of Mung Bean nuclease completely abolished the overhang signal. Annealing with a [TTAGGG]$_4$ probe did not reveal a signal at the position of the telomerec. For quantitation of the G-strand overhangs, hybridization intensity was measured using ImageQuant software by integration of the signal of the entire lane between ~1.5 and 30 kb. DNA samples from cells grown with or without doxycyclin were always analyzed in parallel and run on the same gel.

TRAP Assay.

Reactions were performed with whole cell extracts as described elsewhere [Broccoli et al., Proc. Natl. Acad. Sci. USA, 92:9082–9086 (1995)]. Protein concentrations in the extracts were determined by Bradford assay (BioRad) and 0.5 μg protein was used per extract. RNase digestions were done in parallel to the untreated reaction by addition of 0.2 μg DNase free RNAse A to the telomerase extension reaction.

Results

Overexpression and Inhibition of TRF2.

Figure 13A:
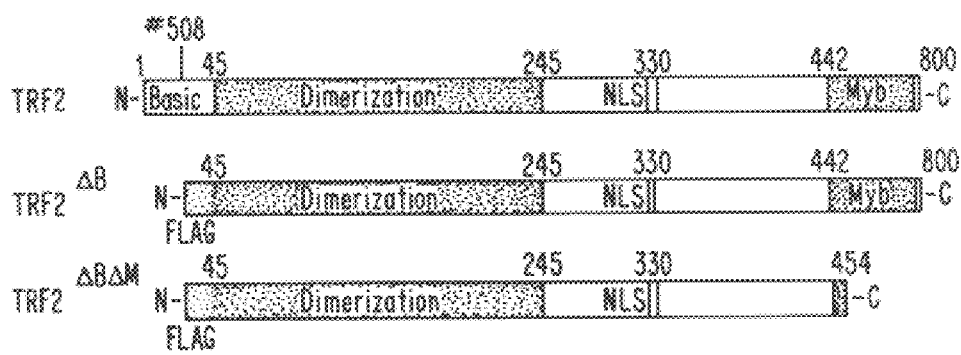
FIG. 13A depicts a schematic of full length human TRF2 [Broccoli et al., *Nature Gen.*, 17:231–235 (1997)] and the deletion mutants TRF2$^{\Delta B}$ and TRF2$^{\Delta B \Delta M}$. The approximate position of the peptide used to raise the polyclonal αTRF2 antibody #508 is indicated. The two TRF2 deletion mutants carry an N-terminal FLAG epitope.
Figure 13B:
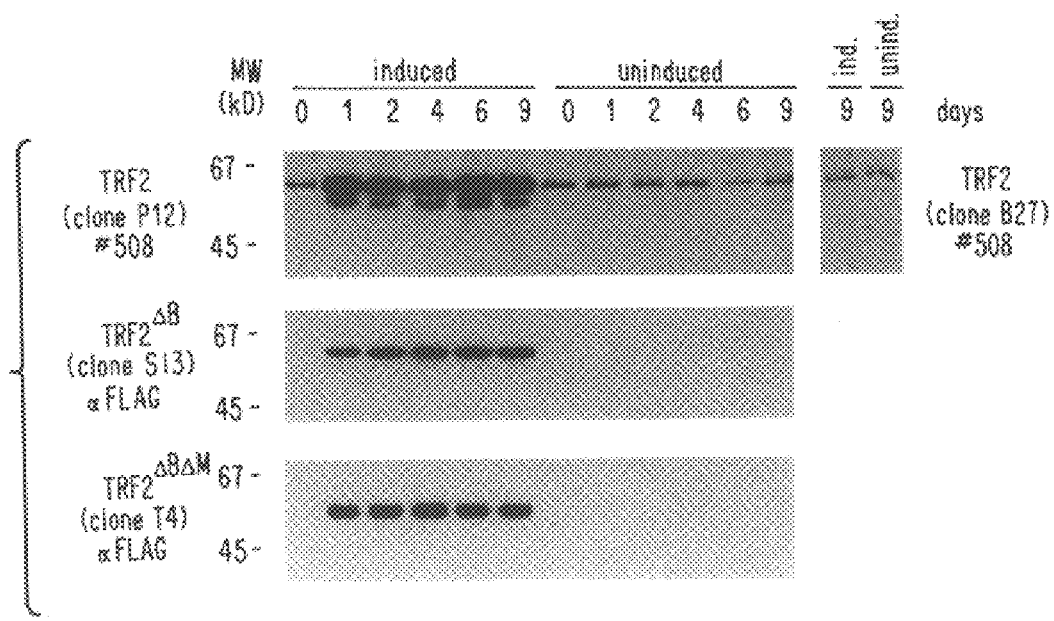
FIG. 13B shows a Western analysis for the inducible expression of the three forms of TRF2 shown in FIG. 13A. Whole cell extracts were prepared from clonal HTC75-derived cell lines expressing the full length TRF2 (clone P12), TRF2$^{\Delta B}$ (clone S13), TRF2$^{\Delta B \Delta M}$ (clone T4), and control cell line B27, which contains the empty vector. Extracts were prepared from cells grown in parallel in the presence (uninduced) or absence (induced) of doxycyclin for the indicated time. For each extract 20 µg of protein was fractioned, blotted and incubated with the primary antibodies indicated in the Figure.

To further examine the role of TRF2 at human telomeres an inducible expression system based on the cell line HTC75, a Tetracyclin-inducible derivative of the human fibrosarcoma cell line HT1008 was used. This expression system was previously employed for the functional analysis of TRF1 [van Steensel and de Lange, Nature, 385:740–743 (1997); U.S. patent application Ser. No. 08/800,264 filed Feb. 13, 1997]. Using this approach, a full length TRF2 protein was expressed. Two truncated alleles in a doxycyclin-controlled fashion were also expressed. One allele (TRF2$^{\Delta B}$) lacked the N-terminal basic domain and the second allele (TRF2$^{\Delta B\Delta M}$) also lacked the C-terminal Myb domain (FIG. 13A). The two truncated proteins were endowed with an N-terminal FLAG tag allowing their detection with a FLAG-specific monoclonal antibody. For detection of full length TRF2, a polyclonal antibody directed against amino acids 16–42 of SEQ ID NO:27 was raised and affinity purified (antibody #508, see FIG. 13B). Clonal HTC75 cells transfected with each of the three TRF2 constructs were derived and shown to express appropriately-sized TRF2 polypeptides in an inducible manner with expression reaching plateau levels 1–2 days post-induction (FIG. 13B). Expression of the endogenous TRF2 protein was not affected by doxycyclin (FIG. 13B). Overexpression of full length TRF2 was also demonstrated by a gel-shift assay for the detection of TTAGGG repeat binding activity.

Consistent with previous experiments using epitope-tagged protein [Broccoli et al., Nature Gen., 17:231–235 (1997)], endogenous TRF2 protein localized to telomeres throughout the cell cycle as evident from the punctate pattern in interphase anid the terminal localization of TRF2 signals in metaphase (FIGS. 14A and 14B). Furthermore, TRF2 co-localized with TRF1 in interphase nuclei (FIGS. 14C and 14D). Transient overexpression of TRF2 did not significantly affect the localization of TRF1 at telomeres, although a minor effect was noted in a few transfected cells with very high levels of TRF2 (FIGS. 14C and 14D). Similarly to full length TRF2, TRF2$^{\Delta B}$ accumulated at telomeres (FIG. 14E), consistent with previous evidence that the basic domain is not required for the localization of this protein to chromosome ends [Broccoli et al., Nature Gen., 17:231–235 (1997)]. Cells expressing high levels of TRF2$^{\Delta B}$ showed diminished levels of the endogenous full length TRF2 on telomeres, evidencing a weak dominant interfering activity for this allele (FIG. 14F). The effect of TRF2$^{\Delta B}$ on the binding of endogenous TRF1 to telomeres was much less conspicuous than the effect on TRF2 and loss of TRF1 signal was only obvious in transiently transfected cells expressing extremely high levels of TRF2$^{\Delta B}$ (FIGS. 14G and 14H). The fact that overexpression of TRF2$^{\Delta B}$ caused displacement of TRF2 but not TRF1 from telomeres indicates that the accumulation of the TRFs at telomeres involves more than their simple binding to TTAGGG repeats.

TRF1 binds to telomeric DNA as a homodimer, requiring two Myb domains for stable association with its target site in vitro and in vivo [Bianchi et al., EMBO J., 16:1785–1794 (1997)]. This architecture has allowed the design of a dominant negative allele of TRF1 containing the dimerization domain and the Nuclear Localization Sequence (NLS), but lacking the Myb DNA binding domain [van Steensel and de Lange, Nature, 385:740–743 (1997); U.S. patent application Ser. No. 08/800,264 filed Feb. 13, 1997]. Since TRF2 carried a similar dimerization domain [Broccoli et al., Nature Gen., 17:231–235 (1997)], it was asked whether expression of an allele of TRF2 that lacked the Myb motif also acted in a dominant negative fashion. Expression of this version of TRF2 (TRF2$^{\Delta B\Delta M}$, FIG. 13A) resulted in a diffuse nuclear staining without evidence for accumulation of this protein at telomeres as expected from the absence of its DNA binding domain (FIGS. 14I and 14K). The expression of TRF2$^{\Delta B\Delta M}$ clearly interfered with the accumulation of the endogenous TRF2 protein at telomeres (FIG. 14J). While TRF2 could be readily demonstrated at telomeres in untransfected control cells, no or little TRF2 protein was observed at telomeric sites in cells expressing the TRF2$^{\Delta B\Delta M}$, attesting to the dominant negative activity of this protein. Consistent with the earlier finding that the dimerization domains of TRF1 and TRF2 do not show strong interactions in vitro [Broccoli et al., Nature Gen., 17:231–235 (1997); Example 7], TRF2$^{\Delta B\Delta M}$ did not affect the accumulation of the endogenous TRF1 protein on telomeres (FIGS. 14K and 14L).

TRF2$^{\Delta B\Delta M}$ and TRF2$^{\Delta B}$ Induce a Growth Arrest in HTC75 Cells.

Figure 15C:
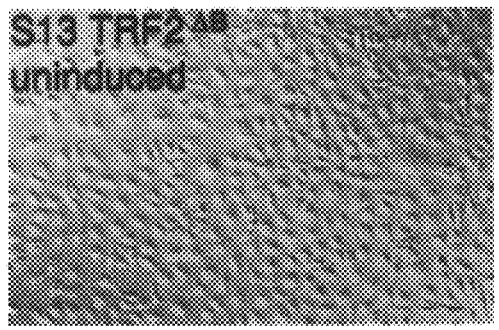
FIGS. 15C–H show the morphological changes of the indicated HTC75 clones expressing the indicated TRF2 alleles grown for 9 days in the presence or absence (uninduced and induced, respectively) of doxycyclin. Cells were stained for β-galactosidase activity at pH 6.0 and photographed using DIC optics.
Figure 15F:
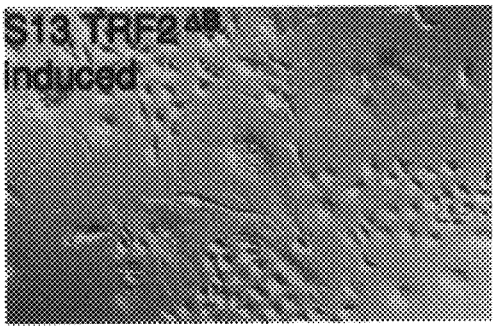
Figure 15D:
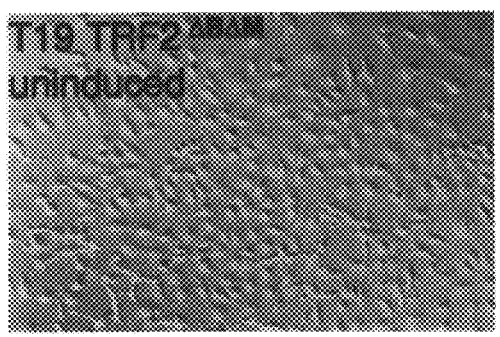
Figure 15G:
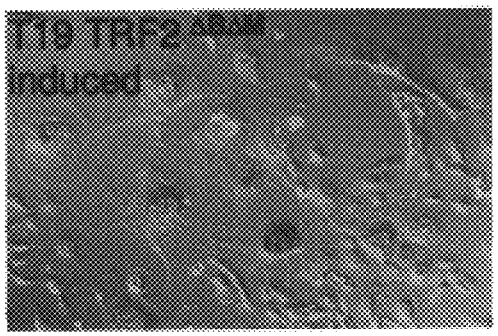
Figure 15E:
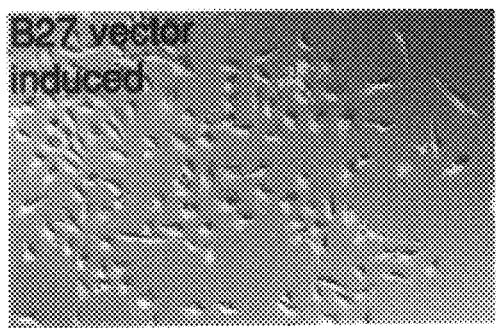
Figure 15H:
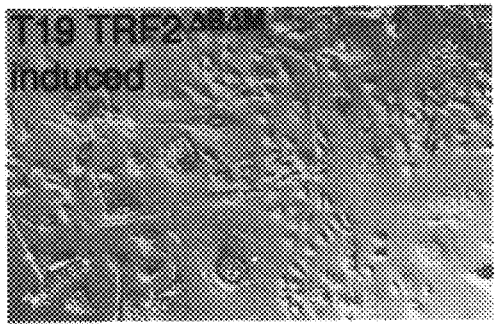

While overexpression of full length TRF2 had no significant effect on the short term growth of HTC75 cells, induction of TRF2$^{\Delta\Delta\Delta M}$ and TRF2$^{\Delta B}$ led to nearly complete inhibition of growth after approximately 4 days of culturing in the absence of doxycyclin (FIG. 15A). This growth arrest was accompanied by induction of a β-galactosidase activity detectable at pH 6 (FIGS. 15C–H), an indication that the cells were undergoing changes akin to senescence [Dimri et al., *Proc. Natl. Acad. Sci. USA*, 92:9363–9367 (1995)] although the staining of the arrested HTC75 cells was less intense than senescent primary human fibroblasts. In addition, the cells became enlarged, had a vacuolated cytoplasm, and often showed multiple small nuclei (FIGS. 15C–H), all morphological phenomena associated with senescence of human cells [Hayflick and Moorhead, *Exp. Cell Res.*, 25:585–621 (1961); Sherwood et al., *Proc. Natl. Acad. Sci. USA*, 85:9086–9090 (1988)]. Consistent with senescence, the arrest appeared irreversible since addition of doxycyclin to the media (to repress synthesis of the TRF2 mutant proteins) on day 12 did not alter the morphology or the proliferative arrest of the cells over a period of 9 days. A substantial proportion of the cells in each culture failed to show convincing morphological alteration and did not stain with β-galactosidase at pH 6.0 (FIGS. 15C–H). Most of these cells expressed very low levels of the TRF2 deletion derivatives. Collectively, the data suggested that TRF2$^{\Delta B}$ and TRF2$^{\Delta B\Delta M}$ induced a growth arrest with phenotypic characteristics of senescence.

TRF2$^{\Delta B\Delta M}$ Induces Chromosome End Fusions.

Figure 16A:
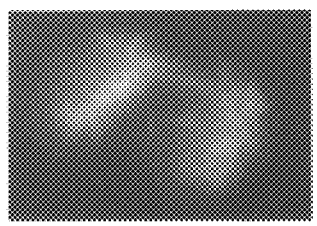
FIGS. 16A–C shows three anaphase cells displaying TRF2$^{\Delta B \Delta M}$-induced anaphase bridges and a lagging chromosome (cell on left). DNA was stained with DAPI.
Figure 16B:
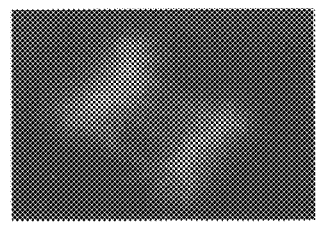
Figure 16C:
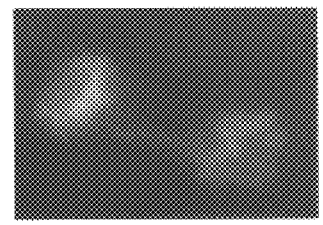
Figure 16D:
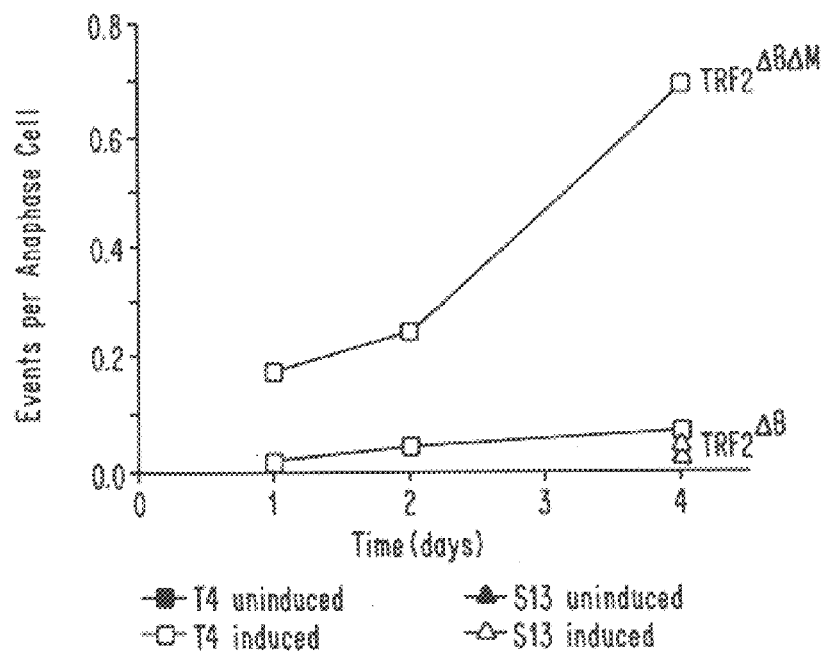
FIG. 16D shows the induction of anaphase bridged and lagging chromosomes (together referred to as "events" on the y-axis) in T4 cells expressing the TRF2$^{\Delta B \Delta M}$ and lack of induced fusions in S13 cells expressing TRF2$^{\Delta B}$. For each time point one hundred anaphase cells were scored for anaphase bridges and lagging chromosomes.

Microscopic analysis of DAPI-stained cells expressing TRF2$^{\Delta B\Delta M}$ revealed the frequent occurrence of anaphase bridges and lagging chromosomes (FIG. 16A). This phenotype was not observed after induction of control cells not expressing TRF2 proteins or in cells induced for full length TRF2 or TRF2$^{\Delta B}$ (FIG. 16B). (However cells expressing TRF2$^{\Delta B}$ often contained small DAPI-positive fragments that were detectable in anaphase).

The incidence of anaphase bridges and lagging chromosomes was quantitated in a total of 100 anaphase cells expressing TRF2$^{\Delta B\Delta M}$, uninduced control cells, and in a cell line expressing TRF2$^{\Delta B}$. At day 4 after induction of TRF2$^{\Delta B\Delta M}$, 40% of the cells had one or more aberrant chromosomes (a bridge or a lagging chromosome) and the culture showed on average 0.7 fusions per anaphase cell (FIG. 16B). By contrast, the level of anaphase bridges and lagging chromosomes was low (<0.1 per cell) in the uninduced control cells and in a cell line expressing TRF2$^{\Delta B}$ (FIG. 16B).

Figure 16E:
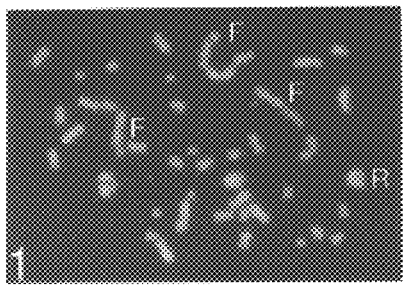
FIGS. 16E–G shows telomere fusions in metaphase chromosomes from T4 cells induced to express TRF2$^{\Delta B \Delta M}$ (FIG. 16E) Metaphase chromosomes showing end-to-end fusions stained with DAPI. Several fusion events (F) and a ring chromosome (R) are indicated.
Figure 16F:
Figure 16G:
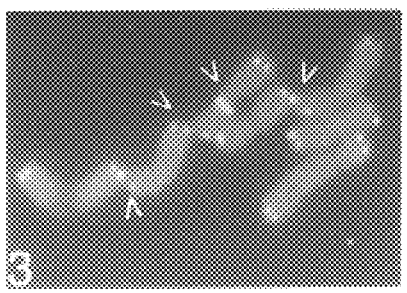

Chromosome end fusions induced by TRF2$^{\Delta B\Delta M}$ were also detected in metaphase spreads. Colcemid treated cells showed dicentrics fused at one or both chromatids, multiple fused chromosomes, and ring chromosomes (FIGS. 16E–G and Table 1). After induction for 6 days, 88% of the metaphases showed at least one fusion (Table 1). Several cells showed trains of 3 or 4 chromosomes (FIGS. 16E–G) and one cell showed as many as 30 individual fusion events. On average there were 2.4 fusion events per cell in cultures of the T4 clone when induced to express TRF2$^{\Delta B\Delta M}$ for 4 or 6 days. Uninduced T4 cells showed only 0.4 events per cell (Table 1). Similarly, a second cell line (T19) expressing TRF2$^{\Delta B\Delta M}$ showed an increase of the fusion frequency from 0.6 to 3.5 per cell upon induction of this dominant negative allele of TRF2. Cells with end-to-end fusions were rare in a control HTC75 cell line transfected with the vector (B27) or in cells expressing TRF2$^{\Delta B}$ (S13) (Table 1). In each case less then 0.3 fusions were observed per cell and fusions were only seen in 10–20% of the cells. Some of these fusion events may actually represent fortuitous juxtaposition of chromosome ends during spreading. Thus, expression of the dominant negative allele of TRF2 increases the frequency of telomere fusions by at least 10 fold. The relatively high frequency of telomere fusions in the cell lines T4 and T19 in the presence of doxycyclin may be due to leaky expression of the TRF2$^{\Delta B\Delta M}$ protein in a fraction of the cells.

TABLE 1

Induction of Chromosome End Fusions by Mutant TRF2 Proteins

| Cell line | Inducible Gene | In- duction | Growth Period (days) | Number of Cells Examined | Fraction with Fusions | Fusions per Cell |
|---|---|---|---|---|---|---|
| B27 | — | − | 4 | 50 | 22% | 0.2 |
| T4 | TRF2 (ΔBΔM) | − | 4 | 100 | 38% | 0.4 |
| T4 | TRF2 (ΔBΔM) | + | 4 | 100 | 77% | 2.4 |
| T4 | TRF2 (ΔBΔM) | + | 6 | 50 | 88% | 2.4 |
| T19 | TRF2 (ΔBΔM) | − | 4 | 50 | 52% | 0.6 |
| T19 | TRF2 (ΔBΔM) | + | 4 | 50 | 78% | 3.5 |
| S13 | TRF2(ΔB) | − | 4 | 50 | 10% | 0.1 |
| S13 | TRF2(ΔB) | + | 4 | 50 | 20% | 0.2 |

It should be stressed that the detection of chromosome end fusions in anaphase and metaphase cells likely represent an underestimate of the actual number of events. For instance, in metaphase cells we do not score for sister-chromatid fusions or fusions that have been followed by chromosome breakage and fusions are only detectable in anaphase cells when a bridge or lagging chromosome results. Thus, our quantitation of chromosome ends fusions probably reflects a minimal estimate of the actual fusion frequency in the cells.

Taken together the cytogenetic analysis indicated that the removal of TRF2 from telomeres leads to loss of telomeric protection detectable as end-to-end fusion in anaphase and metaphase chromosomes. It was unlikely that this phenotype was caused by the presence of excess TRF2 protein in the nucleoplasm because overexpression of full length TRF2 similarly resulted in the presence of TRF2 throughout the nucleus, yet induction of anaphase bridges was not noted in such cells.

Fused Chromosome Ends Contain Telomeric DNA.

Fusion of chromosome ends has been documented in cells containing DNA damage and in cells that have depleted their reservoir of telomeric DNA. In those cases, telomeric DNA is usually not detectable at the site of fusion [Blasco et al., *Cell.*, 91:25–34 (1997)]. Therefore it was determined whether the fusions in response to TRF2$^{\Delta B\Delta M}$ were similarly correlated with loss of telomeric DNA from individual chromosome ends. Using a fluoresceine-labelled peptide nucleic acid (PNA) [CCCTAA]$_3$ probe specific for telomeric DNA, in situ hybridizations were carried out on metaphase spreads from cells displaying the chromosome ends fusions. The results in FIGS. 16E–G showed that telomeric DNA was preserved at the site of chromosome end fusion. In the majority of cases, the signal at the fused ends was substantially stronger than that found at free telomeres, consistent with the telomeric stretches of both fused chromosome ends remaining intact.

TRF2$^{\Delta B\Delta M}$ Induces Molecular Joining of Telomeric DNA Sequences.

Figure 17A:
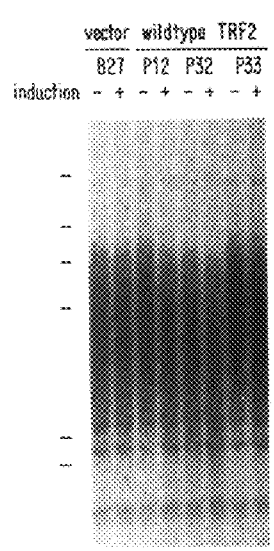
FIG. 17A shows the telomere structure in clonal HTC75 lines expressing wildtype TRF2 (P clones) and in a vector control cell line (clone B27) grown in the presence and absence of doxycyclin (− and + induction respectively) for eight population doublings.
Figure 17B:
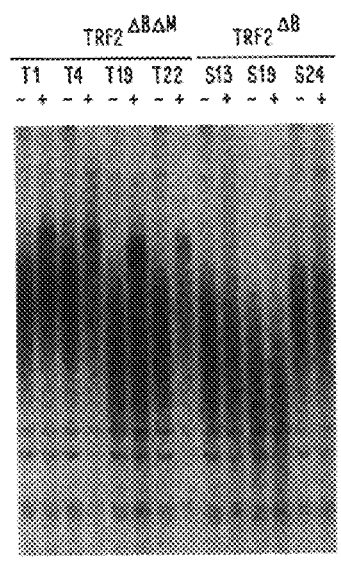
FIG. 17B shows the telomere structure in clonal lines expressing the indicated deletion of alleles of TRF2 grown with and without doxycyclin for 9 days (− and + induction respectively).
Figure 17C:
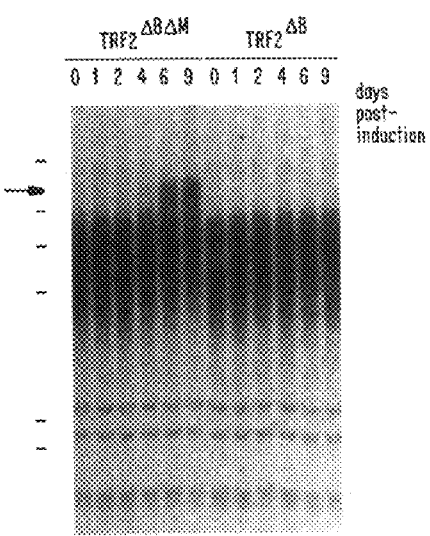
FIG. 17C depicts the time course of changes in telomere structure in T4 cells induced to express TRF2$^{\Delta B \Delta M}$ and in S24 cells induced to express TRF2$^{\Delta B}$.

In order to establish whether the joining of telomeres in TRF2$^{\Delta B\Delta M}$-expressing cells depended on a proteinaceous bridge, evidence for telomere fusion in naked genomic DNA was sought. Detection of telomeric restriction fragments in genomic DNA from vector control cells and cells expressing full length TRF2 or TRF2$^{\Delta B}$ showed no change in telomere structure over the course of the induction period (FIGS. 17A and B). By contrast, cells induced for TRF2$^{\Delta B\Delta M}$ revealed a dramatic alteration in the pattern of HinfI/RsaI fragments detectable with TTAGGG repeat probes (FIG. 17B). A new class of longer restriction fragments first became apparent at 4 days post-induction (FIG. 17C) and this set of new fragments increased in intensity, but not in length over the course of the 9 day experiment. The new class of TTAGGG repeat fragments was observed in four independent clonal TRF29$^{\Delta B\Delta M}$ cell lines and in each case they migrated at a MW exactly twice (ratio of 2.0±0.2 (n=4)) that of the length of the original population of telomeric fragments. Quantitation of genomic blots indicated that up to 22% (average value 13.8±6.1% (n=4)) of the TTAGGG repeat signal was found in the larger class of hybridizing material at day 9 post-induction.

Figure 17D:
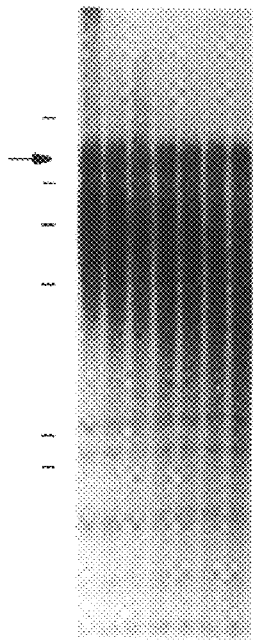
FIG. 17D shows the Bal31 exonuclease digestion of DNA from T4 cells induced to express TRF2$^{\Delta B \Delta M}$ for 9 days.
Figure 17E:
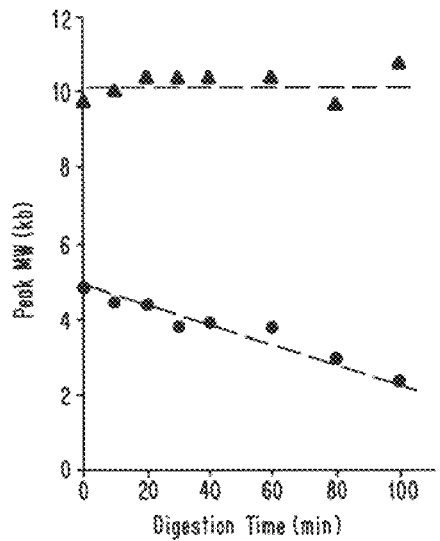
FIG. 17E shows the quantitation of Bal31 exonuclease experiment similar to that shown in FIG. 17D performed with DNA from T19 cells induced to express TRF2$^{\Delta B \Delta M}$ for 9 days.

The fact that the TRF2$^{\Delta B\Delta M}$-induced new TTAGGG repeat fragments were twice the size of the original telomeres suggested that these molecules might represent the chromosome end fusions that were first detected by cytogenetic analysis of metaphase and anaphase cells. Such structures would be expected to be resistant to exonuclease Bal31 treatment of intact genomic DNA, whereas this exonuclease should readily attack the new class of larger TTAGGG repeat fragments if they represented elongated telomeres. Bal31 digestion of genomic DNA from T4 cells expressing TRF2$^{\Delta B\Delta M}$ indeed showed the resistance of the longer TTAGGG repeat fragments to this exonuclease (FIG. 17D). Quantitation of a second data set obtained with TRF2$^{\Delta B\Delta M}$-expressing T19 cells (FIG. 17E) showed that while the original telomeric loci were gradually shortened by Bal31, the TRF2$^{\Delta B\Delta M}$-induced longer fragments were not affected by the enzyme. This result indicated that the new class of TTAGGG repeat fragments did not represent elongated telomeres. Therefore these longer species are derived from the fused chromosome ends. Since the detection of fused ends in naked DNA indicates that the telomeres are held together by nucleic acid interactions, these end-joining events are referred to as telomeric fusions.

Figure 17F:
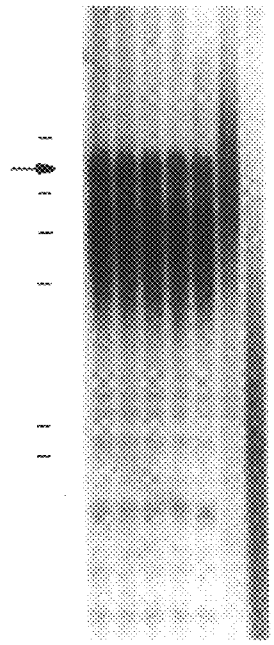
FIG. 17F shows the heat stability of the telomeric fusions. DNA derived from the same cells used in FIG. 17D was treated for 10 minutes at the indicated temperatures and immediately loaded on an agarose gel.

The telomere fusions might be mediated by (Hoogsteen) base-pairing between the G-strand overhangs at human telomeres. Such a configuration was previously shown to temporarily link the termini of yeast chromosomes which carry long G-tails in late S-phase. Since this type of association was shown to be labile at 72–78° C., it was determined as to whether the fused human telomeres could be similarly resolved by treatment at that temperature. As shown in FIG. 17F, the fused telomeres derived from TRF2$^{\Delta B\Delta M}$-expressing cells are resistant to a temperature of 85° C. and only melt out at higher temperatures. Such temperatures also denature bulk DNA. This observation argues against the presence of G—G basepairing in the 3' overhang as the main mechanism by which telomere fusions occur.

However, it is conceivable that the human G-tails form more stable G-G base paired structures than yeast telomere overhangs. However, the observation that the fused telomeric fragments are resistant to Bal31 nuclease constitutes further evidence against G-tail interactions in the fused telomeres. Since Bal31 readily cleaves single-stranded DNA, including very short regions of unpaired sequences such as those occurring due to pyrimidine dimers [Linn and Roberts, Nucleases, Cold Spring Harbor Laboratory, Cold Spring Harbor (1982)], this enzyme would be expected to digest single-stranded regions within G-G basepaired telomeric tails and resolve the joins. Therefore the telomere fusions appear to be the result of end-to-end ligations of one or both telomeric strands.

Telomeric Fusions Correlate with the Loss of G-strand Overhangs.

Figure 18C:
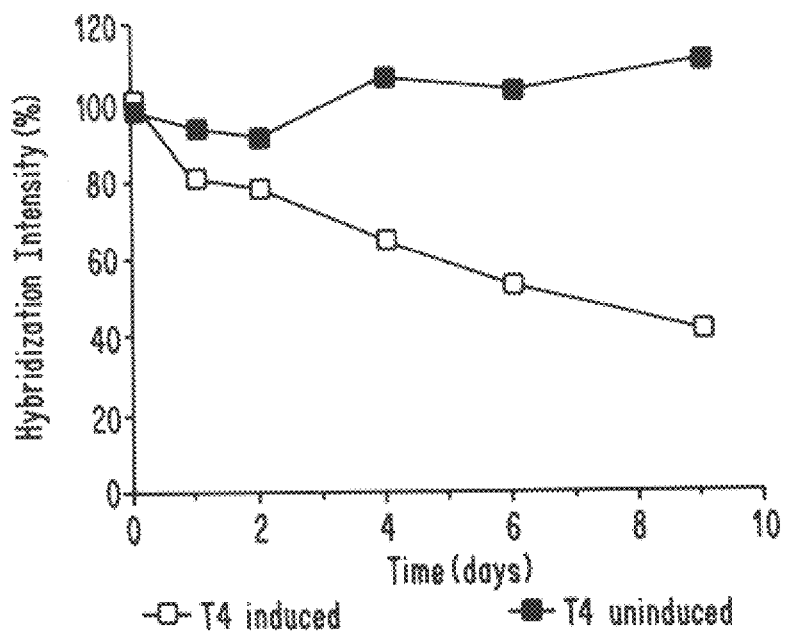
FIG. 18C shows the quantitation of the loss of G-strand overhangs upon induction of TRF2$^{\Delta B \Delta M}$ in two independents experiments performed with the T4 clone. The data were derived from two experiments similar to those shown in FIG. 18B and the average value was plotted.
Figure 18D:
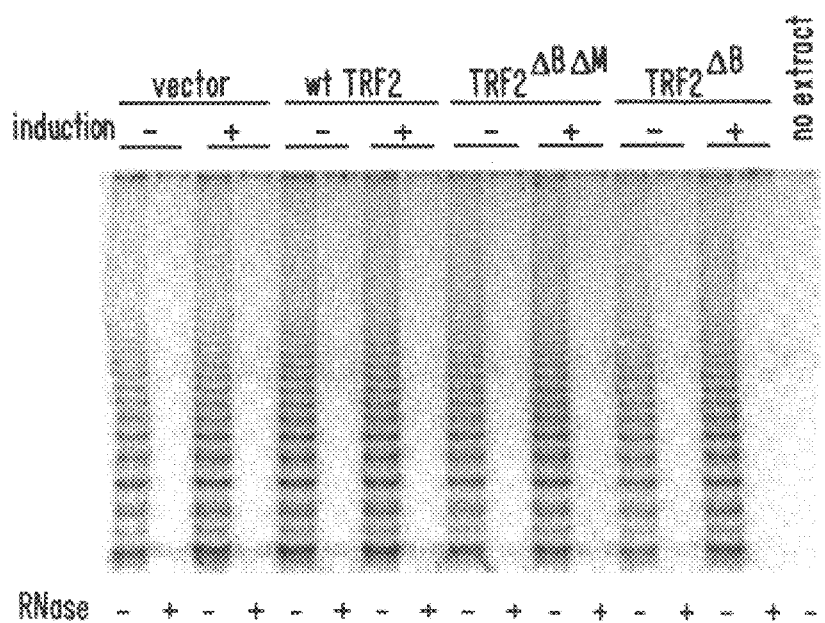
FIG. 18D shows the similar telomerase activity in four HTC75 clonal lines expressing the indicated TRF2 polypeptides grown for 9 days in the presence or absence of doxycyclin (− and + induction respectively). For each extract, identical amounts of protein (0.5 μg) were tested using the TRAP assay.

Ligation of telomere termini would be unexpected if, as proposed by Makarov et al. [Cell, 88:657–666 (1997)], all or most human telomeres contain long regions of single-stranded TTAGGG repeat DNA. It was therefore prudent to appraise the status of the telomere termini in cells displaying telomere fusions. Makarov et al.[Cell, 88:657–666 (1997)] have developed a method for the quantitative detection of single-stranded TTAGGG repeats at the ends of human chromosomes. In this technique, HinfI/RsaI digested non-denatured genomic DNA is annealed to labelled [CCCTAA]$_4$ oligonucleotide and the indirectly labelled telomeric fragments are detected by autoradiography of size fractionated DNA. This technique evaluates the relative amount of unpaired single-stranded TTAGGG repeats in genomic DNA but does not discriminate between loss of signal due to shortening of the G-tails, complete disappearance of G-tails, or reduced detection of G-tails due to G-G base pairing in the overhangs, Using the [CCCTAA]$_4$ probe on DNA derived from the control cell line B27, G-strand overhangs at the ends of wildtype telomeres were readily detected (FIG. 18). To validate the method, it was verified that the probe did not anneal to DNA that was pretreated with Mung Bean nuclease and that annealing of a [TTAGGG]$_4$ probe did not result in a telomeric pattern. When the amount of unpaired TTAGGG repeat DNA in cells grown in the presence and absence of doxycyclin was compared, no alteration in the signal wag noted in cells induced to express full length TRF2 or the TRF2$^{\Delta B}$ allele (FIG. 18A). Similarly, overexpression of TRF1 or a dominant negative allele of TRF1 [van Steensel and de Lange, Nature, 385:740–743 (1997); U.S. patent application Ser. No. 08/800,264 filed Feb. 13, 1997] did not affect the presence of unpaired TTAGGG repeats at telomere termini. By contrast, cells expressing TRF2$^{\Delta B\Delta M}$ displayed a consistent reduction in the amount of detectable G-tail sequences and no signal was present at the position of the larger terminal fragments representing the fused telomeres (FIGS. 18A and 18B). Quantitation of the data on four clonal cell lines showed that induction of TRF2$^{\Delta B\Delta M}$ for 6–9 days resulted in a 40–60% decline in the total single-stranded TTAGGG repeat signals at chromosome ends (FIG. 18C). These data indicated that TRF2$^{\Delta B\Delta M}$ expression resulted in the loss of detectable single-stranded TTAGGG repeats at chromosome ends.

TRF2 does not Affect Telomerase Expression.

The loss of G-tail sequences in TRF2$^{\Delta B\Delta M}$-expressing cells could be explained if TRF2 is a positive regulator of telomerase expression. Therefore the telomerase levels in extracts of cells induced for the three types of TRF2 protein used in this study were examined along with the matching uninduced controls using the PCR-based TRAP assay [Kim et al., Science, 266:2011–2015 (1994)]. The result revealed similar levels of robust telomerase activity in each cell type regardless of the presence of doxycyclin in the media (FIG. 18D), indicating that the telomerase activity is not affected by TRF2 in this setting and that the loss of G-tail DNA occurs through some other mechanism.

Telomere Protection by TRF2 and the Role of G-Tails.

A striking consequence of loss of TRF2 function is the formation of end-to-end fusions detectable in metaphase and anaphase chromosomes. In contrast with the first documented end-to-end fusions which involved broken chromosome ends in Drosophila and maize [Muller, The Collecting Net-Woods Hole, 13:181–195 (1938); McClintock, Genetics, 26:234–282 (1941); McClintock, Proc. Natl.

*Acad. Sci. USA*, 28:458–463 (1942)], the fusions induced by loss of TRF2 carry telomeric DNA. The presence of telomeric sequences at the fusions was demonstrated by in situ hybridization and the fused telomeric fragments were detectable in protein-free genomic DNA. Yet while the telomeric TTAGGG repeats persisted, the telomeres failed to protect the chromosome ends from fusion, indicating that the duplex stretch of TTAGGG repeats itself is insufficient for telomere protection in human cells. Therefore the protective function of telomeres is conferred by a nucleoprotein complex containing TRF2.

The data also reveal a crucial role for TRF2 in the maintenance of unpaired G-strand overhangs at telomere termini. Loss of TRF2 from telomeres caused by expression of the dominant negative TRF2$^{\Delta B \Delta M}$ allele resulted in a ~50% reduction in the single-stranded TTAGGG repeat signal. Inhibition of TRF2 appears to result in an actual loss of G-tail DNA sequences from human chromosome ends. Such G-tail loss could be the consequence of a failure to protect the overhangs from degradation or could result from a deficiency in creating new G-tails after DNA replication.

TRF2 is the first telomere associated protein implicated in the maintenance of the correct DNA configuration of the telomeric 3' overhang. It was previously shown that telomerase is not involved in the maintenance of G-tails in yeast and mammals [Dionne and Wellinger, *Proc. Natl. Acad. Sci. USA*, 93:13902–13907 (1996)] and none of the other telomeric proteins identified in eukaryotes are known to affect this aspect of telomere synthesis. Our data indicate that changes in telomerase expression are unlikely to be involved in this process.

Collectively, the data are consistent with a model in which TRF2 protects telomeres from fusion through the maintenance of their single-strand TTAGGG repeat overhangs. This view is consistent with the finding that G-strand overhangs are a universal feature of eukaryotic telomeres [reviewed in Wellinger and Sen, *Eur. J. Cancer*, 33:735–749 (1997)] and identification of G-strand binding proteins in several systems. Thus, one of the main objectives of the transactions at telomeres may be to create and maintain a protrusion of single-stranded telomeric repeats that can bind specific proteins. This terminal complex could constitute the unique aspect of telomeres that allows cells to distinguish natural chromosome ends from broken DNA.

The 3' extension of TTAGGG repeats at human chromosome ends are likely to serve as a binding site for single-strand specific telomeric proteins but the actual factors involved in this function are still elusive. A candidate activity that could cap the TTAGGG repeats has been identified in Xenopus extracts [Cardenas et al., *Genes Dev.*, 7:883–894 (1993)], G-strand overhangs are bound by terminus specific proteins in ciliates [Gottschling and Zakian, *Cell*, 47:195–205 (1986); Price, *Mol. Cell. Biol.*, 10:3241–3431 (1990)], and budding yeast telomeres are protected from degradation by Cdc 1 3p [Garvik, *Mol. Cell. Biol.*, 15:6128–6138 (1995)], a protein with G-tail binding activity in vitro [Lin and Zakian, *Proc. Natl. Acad. Sci. USA*, 93:13760–13765 (1996); Nugent et al., *Science*, 274:249–252 (1996)]. However, human homologs of these factors have not been identified yet. It should also be noted that G-rich telomeric repeats have the ability to form G-G (Hoogsteen) basepaired folded structures with several alternative conformations [reviewed by Henderson, In *Telomeres*, Cold Spring Harbor Press, Cold Spring Harbor (1995)] that could potentially contribute to the protection of chromosome ends.

The telomeric fusions are probably the consequence of processing of unmasked telomere termini by enzymes normally acting on broken DNA. A possible scenario is that loss of TRF2 from the chromosome ends leads to disappearance of the G-tail overhangs and activation of a DNA damage response by the denuded telomeres. A cell cycle arrest might ensue under these conditions and those cells that process the offending ends into fused telomeres may preferentially continue in the cell cycle leading to the observed metaphase abnormalities and anaphase bridges. The occurrence of fused telomeres in turn creates problems in mitosis due to the mechanical difficulties in segregating dicentric chromosomes which require either a break in the spindle or a break in a chromatid. Thus, the loss of telomeric protection may well lead to activation of checkpoints at several stages of the cell cycle.

Chromosome End Fusions in Cells with Critically Shortened Telomeres.

Telomere associations have been observed by cytogenetic inspection of chromosome behavior in a number of different settings, including senescent primary cells, cells transformed with viral agents, and in a large variety of tumor specimen [reviewed in de Lange, In Telomeres, Cold Spring Harbor Press, Cold Spring Harbor (1995)]. Although this was not always established in these studies, data accumulated over the past decade suggest that in most cases where telomere associations were observed, the telomeres may have been fairly short. Indeed in studies that measured telomere length directly, there is a correlation between shortened telomeres and their association in metaphase [Counter et al., *EMBO J.*, 11: 1921–1929 (1992); Saltman et al., *Chromosoma*, 102:121–128 (1993)]. Our observations on the behavior of chromosome ends after loss of the duplex telomeric DNA binding protein, TRF2, are consistent with a molecular mechanism underlying these telomere associations: When the telomeres reach a critical minimal length their ability to recruit sufficient TRF2 is diminished and end-to-end fusions result. The length setting in which this aspect of telomere function becomes compromised has not been fully established.

Telomeres and Cellular Senescence.

Expression of two mutant TRF2 polypeptides induced a growth arrest in the human fibrosarcoma cells used in this study. This arrest had several features consistent with the induction of senescence, including a specific cellular morphology, expression of a β-galactosidase activity correlated with senescence, and the irreversible nature of the arrest. This senescent-like phenotype in these transformed cells is likely to be directly related to the replicative senescence described in primary human cells. These results indicate that transformed human cells are rather sensitive to the status of their telomeres and that interference with telomere function can inhibit proliferation of malignant cells.

Two mechanisms for the induction of the observed growth arrest can be entertained at this stage. Since the growth arrest in HTC75 cells is accompanied by chromosomal abnormalities, one possibility is that the arrest is a response to DNA damage arising from the altered TRF2 activity at telomeres. The second possibility is that there exists a specific pathway allowing cells to evaluate the status of their telomeres. For instance, the presence of the basic N-terminus of TRF2 on telomeres may be required to suppress cellular senescence. Overexpression of a mutant protein lacking this domain would then be expected to induce arrest by displacing the endogenous TRF2. Similarly, the strong dominant negative activity of TRF2$^{\Delta B \Delta M}$ would result in telomeres lacking the basic N-terminal domain of TRF2 and cause an arrest signal. Such a mechanism would allow cells to monitor the length of their telomeres and initiate a growth arrest and senescence program in response to critical shortening of the telomeres.

Requirements for Telomere Formation in Human Cells.

Transfection of TTAGGG repeats into human cells leads to efficient de novo formation of fully functional telomeres [Farr et al., *Proc. Natl. Acad. Sci. USA*, 88:7006–7010 (1991)]. An excellent correlation between the binding specificity of TRF1 and the cis-acting requirements for de novo telomere formation in human cells has been determined [Hanish et al., *Proc. Natl. Acad. Sci. USA*, 91:8861–8865 (1994)], indicating that the acquisition of TRF1 might be an essential step in telomere healing. However, the subsequent cloning of TRF2 revealed that this protein has the same sequence preference as TRF1 [Broccoli et al., *Nature Gen.*, 17:231–235 (1997)], raising the possibility that TRF2, rather than TRF1 is involved in the conversion of the transfected DNA into a functional telomere. The finding that TRF2 is important for the protection of chromosome ends now indicates an alternative scenario for de novo telomere formation in human cells. Acquisition of TRF2 may be one of the early steps as the transfected telomere seed enters the nucleus. According to the current data, TRF2 has the ability to protect the TTAGGG repeats from ligation to other DNA. As a result, the TRF2-bound end of the transfected linear plasmid may be prevented from undergoing the recombination reaction that normally leads to chromosome-internal integration of transfected DNA. Recombination of the other (non-telomeric) end of the transfected DNA with a resident chromosomal locus will then lead to the observed chromosome fragmentation. Telomerase subsequently elongates the telomere seed to form a fully functional telomere.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various publications are cited herein, the disclosures of which are incorporated by reference in their entireties.

What is claimed is:

1. A vertebrate telomere repeat binding factor 2 (TRF2) obtained by expressing a nucleic acid operatively linked to an expression control sequence in a cell; wherein said nucleic acid encodes a TRF2 comprising the amino acid sequence of SEQ ID NO:27, or an amino acid sequence that is at least 80% identical to that of SEQ ID:27; wherein said cell has been transformed or transfected by said nucleic acid; and wherein said TRF2 has the following characteristics:
 a) a basic N-terminal domain;
 b) a dimerization domain; and
 a Myb domain; wherein when the basic N-terminal domain is removed, the TRF detectable binds to the telomere repeat sequence $(TTAGGG)_{12}$.

2. An isolated vertebrate telomere repeat binding factor (TRF) comprising an amino acid sequence that is at least 80% identical to that of SEQ ID NO:27, and comprising the following characteristics:
 a) a basic N-terminal domain;
 b) a dimerization domain; and
 c) a Myb domain, wherein when the basic N-terminal domain is removed, the TRF detectably binds to the telomere repeat sequence $(TTAGGG)_{12}$.

3. The isolated TRF of claim 2 that is a mammalian protein.

4. The isolated TRF of claim 2 that is a chimeric and/or fusion protein.

5. The isolated TRF of claim 3 that is a human protein comprising the amino acid sequence of SEQ ID NO:27, or SEQ ID NO:27 with a conservative amino acid substitution.

6. The isolated TRF of claim 3 that is a murine protein comprising the amino acid sequence of SEQ ID NO:29, or SEQ ID NO:29 with a conservative amino acid substitution.

7. An isolated protein comprising the basic N-terminal domain of a vertebrate telomere repeat binding factor 2 (TRF2) that has the amino acid sequence of SEQ ID NO:37, or an amino acid sequence that is at least 80% identical to that of SEQ ID NO:37; and wherein said TRF2 comprises the following characteristics:
 a) a basic N-terminal domain;
 b) a dimerization domain; and
 c) a Myb domain; wherein when the basic N-terminal domain is removed, the TRF2 detectably binds to the telomere repeat sequence $(TTAGGG)_{12}$.

8. The isolated protein of claim 7 that is a chimeric and/or fusion protein.

9. An isolated protein comprising a dimerization domain of a vertebrate telomere repeat binding factor 2 (TRF2) that comprises the amino acid sequence of SEQ ID NO:45, or an amino acid sequence that is at least 80% identical to that of SEQ ID NO:45; and wherein said TRF2 comprises the following characteristics:
 a) a basic N-terminal domain;
 b) a dimerization domain; and
 c) a Myb domain; wherein when the basic N-terminal domain is removed, the TRF2 detectably binds to the telomere repeat sequence $(TTAGGG)_{12}$.

10. The isolated protein of claim 9 that is a chimeric and/or fusion protein.

11. An isolated protein that is a truncated vertebrate telomere repeat binding factor 2 (TRF2) that has the amino acid sequence of SEQ ID NO:31 or an amino acid sequence that is at least 80% identical to that of SEQ ID NO:31; wherein said truncated vertebrate TRF2 comprises the following characteristics:
 a) a dimerization domain; and
 b) a Myb domain; wherein said truncated vertebrate TRF2 detectably binds to the telomere repeat sequence $(TTAGGG)_{12}$.

12. The isolated protein of claim 11 that is a chimeric and/or fusion protein.

13. An antibody that recognizes a basic N-terminal domain of a vertebrate telomere repeat binding factor 2 (TRF2) that has the amino acid sequence of SEQ ID NO:37, or an amino acid sequence that is at least 80% identical to that of SEQ ID NO:37; and wherein said TRF2 comprises the following characteristics:
 a) a basic N-terminal domain;
 b) a dimerization domain; and
 c) a Myb domain; wherein when the basic N-terminal domain is removed, the TRF2 detectably binds to the telomere repeat sequence $(TTAGGG)_{12}$.

14. The antibody of claim 13 which is a polyclonal antibody.

15. The antibody of claim 13 which is a monoclonal antibody.

16. An immortal cell line that produced a monoclonal antibody according to claim 15.

17. The antibody of claim 13 which is a chimeric antibody.

18. An antibody raised against a vertebrate telomere repeat binding factor2 (TRF2) comprising an amino acid sequence that is at least 80% identical to that of SEQ ID NO:27; wherein said TRF comprises the following characteristics:
 a) a basic N-terminal domain;
 b) a dimerization domain; and
 c) a Myb domain; wherein when the basic N-terminal domain is removed, the TRF detectably binds to the telomere repeat sequence $(TTAGGG)_{12}$.

19. The antibody of claim 18 which is a polyclonal antibody.

20. The antibody of claim 18 which is a monoclonal antibody.

21. An immortal cell line that produced a monoclonal antibody according to claim 20.

22. The antibody of claim 18 which is a chimeric antibody.

23. An antibody raised against a vertebrate telomere repeat binding factor 2 (TRF2) dimerization domain consisting essentially of an amino acid sequence that is at least 80% identical to that of SEQ ID NO:45; wherein said TRF comprises the following characteristics:

a) a basic N-terminal domain;

b) a dimerization domain; and c) a Myb domain; wherein when the basic N-terminal domain is removed, the TRF detectably binds to the telomere repeat sequence $(TTAGGG)_{12}$.

24. The antibody of claim 23 which is a polyclonal antibody.

25. The antibody of claim 23 which is a monoclonal antibody.

26. An immortal cell line that produced a monoclonal antibody according to claim 25.

27. The antibody of claim 23 which is a chimeric antibody.

28. An isolated fragment of a vertebrate telomere repeat binding factor 2 (TRF2) consisting of 30 to 90 amino acids; wherein said fragment comprises the basic N-terminal domain of the TRF2; wherein said TRF2 comprises an amino acid sequence that is at least 80% identical to that of SEQ ID NO:27, and wherein said TRF2 further comprises the following characteristics:

a) a basic N-terminal domain;

b) a dimerization domain; and c) a Myb domain; wherein when the basic N-terminal domain is removed, the TRF detectably binds to the telomere repeat sequence $(TTAGGG)_{12}$.

29. A chimeric and/or fusion peptide or protein that comprises the peptide of claim 28.

30. An isolated fragment of a vertebrate telomere repeat binding factor 2 (TRF2); wherein said fragment consists of essentially of the dimerization domain of the TRF2 which consists of an amino acid sequence that is at least 80% identical to that of SEQ ID NO:45; wherein said TRF2 comprises the following characteristics:

a) a basic N-terminal domain;

b) a dimerization domain; and c) a Myb domain; wherein when the basic N-terminal domain is removed, the TRF2 detectably binds to the telomere repeat sequence $(TTAGGG)_{12}$.

31. A chimeric and/or fusion peptide or protein that comprises the fragment of claim 30.

32. The fragment of claim 30 wherein the dimerization domain of the TRF2 is selected from the group consisting of SEQ ID NO:45, SEQ ID NO:45 with a conservative amino acid substitution, SEQ ID NO:47, and SEQ ID NO:47 with a conservative amino acid substitution.

33. The isolated fragment of claim 28 wherein said fragment consists of the amino acid sequence selected from the group consisting of SEQ ID NO:37, SEQ ID NO:37 with a conservative amino acid substitution, SEQ ID NO:39, and SEQ ID NO:39 with a conservative amino acid substitution.

34. The antibody of claim 13 that comprises the amino acid sequence of SEQ ID NO:37 with a conservative amino acid substitution.

35. The truncated TRF2 of claim 11 that comprises the amino acid sequence of SEQ ID NO:31 with a conservative amino acid substitution.

36. The isolated protein of claim 9 that comprises the amino acid sequence of SEQ ID NO:45 with a conservative amino acid substitution.

37. The isolated protein of claim 7 that comprises the amino acid sequence of SEQ ID NO:37 with a conservative amino acid substitution.

38. The TRF2 of claim 1 comprising the amino acid sequence of SEQ ID NO:27 with a conservative amino acid substitution.

\* \* \* \* \*

UNITED STATES PATENT AND TRADEMARK OFFICE
CERTIFICATE OF CORRECTION

PATENT NO.   : 6,297,356 B1
DATED        : October 2, 2001
INVENTOR(S)  : Titia de Lange; Domique Broccoli and Agata Smogorzenska It is certified that error appears in the above-identified patent and that said Letters Patent is hereby corrected as shown below:

<u>Title page,</u>
Item [73], please change the Assignee from "The Rockfeller University" to read -- The Rockefeller University --.

Signed and Sealed this

Second Day of April, 2002

Attest:

JAMES E. ROGAN
*Director of the United States Patent and Trademark Office*

*Attesting Officer*